United States Patent
Wang et al.

(10) Patent No.: US 11,555,070 B2
(45) Date of Patent: Jan. 17, 2023

(54) ANTI-CLAUDIN 18.2 ANTIBODIES AND USES THEREOF

(71) Applicant: Phanes Therapeutics, Inc., San Diego, CA (US)

(72) Inventors: Minghan Wang, San Diego, CA (US); Hui Zou, Dallas, TX (US); Haiqun Jia, San Diego, CA (US)

(73) Assignee: Phanes Therapeutics, Inc., San Diego, CA (US)

( * ) Notice: Subject to any disclaimer, the term of this patent is extended or adjusted under 35 U.S.C. 154(b) by 199 days.

(21) Appl. No.: 15/733,553

(22) PCT Filed: Mar. 6, 2019

(86) PCT No.: PCT/US2019/020872
§ 371 (c)(1),
(2) Date: Aug. 26, 2020

(87) PCT Pub. No.: WO2019/173420
PCT Pub. Date: Sep. 12, 2019

(65) Prior Publication Data
US 2020/0399364 A1 Dec. 24, 2020

Related U.S. Application Data

(60) Provisional application No. 62/640,288, filed on Mar. 8, 2018, provisional application No. 62/714,254, filed on Aug. 3, 2018.

(51) Int. Cl.
*C07K 16/28* (2006.01)
*G01N 33/574* (2006.01)

(52) U.S. Cl.
CPC ....... *C07K 16/28* (2013.01); *G01N 33/57492* (2013.01); *C07K 2317/24* (2013.01); *C07K 2317/31* (2013.01); *C07K 2317/73* (2013.01); *C07K 2317/732* (2013.01)

(58) Field of Classification Search
CPC .............. C07K 16/28; C07K 2317/24; C07K 2317/31; C07K 2317/73; C07K 2317/732; G01N 33/57492
See application file for complete search history.

(56) References Cited

U.S. PATENT DOCUMENTS

| | | | | |
|---|---|---|---|---|
| 10,137,195 B2 * | 11/2018 | Sahin | ............... | A61K 39/39558 |
| 2015/0132253 A1 | 5/2015 | Sahin | | |
| 2016/0272711 A1 | 9/2016 | Sahin | | |
| 2016/0339101 A1 | 11/2016 | Sahin | | |

FOREIGN PATENT DOCUMENTS

| | | |
|---|---|---|
| WO | 2007059997 | 5/2007 |
| WO | 2008145338 | 12/2008 |
| WO | 2011113546 | 9/2011 |
| WO | 2013167153 | 11/2013 |
| WO | 2013167259 | 11/2013 |
| WO | 2013174404 | 11/2013 |
| WO | 2013174509 | 11/2013 |
| WO | 2014075697 | 5/2014 |
| WO | 2014075788 | 5/2014 |
| WO | 2014127785 | 8/2014 |
| WO | 2014127906 | 8/2014 |
| WO | 2014146672 | 9/2014 |
| WO | 2014146778 | 9/2014 |
| WO | 2015113576 | 8/2015 |
| WO | 2016165765 | 10/2016 |
| WO | 2016166122 | 10/2016 |
| WO | 2016166124 | 10/2016 |
| WO | 2016180468 | 11/2016 |
| WO | 2016180782 | 11/2016 |
| WO | 2018006882 | 1/2018 |

OTHER PUBLICATIONS

Gunzel et al., "Claudins and the Modulation of Tight Junction Permeability", Physiol Rev. 2013; 93:525-569.
Hayashi et al., "Deficiency of Claudin-18 Causes Paracellular H+ Leakage, Up-regulation of Interleukin-1 B, and Atrophic Gastritis in Mice", Gastroenterology 2012; 142:292-304.
Keira et al., "An immunohistochemical marker panel including claudin-18, maspin, and p53 improves diagnostic accuracy of bile duct neoplasms in surgical and presurgical biopsy specimens", Virchows Arch. 2015; 466:265-277.
Niimi et al., "claudin-18, a Novel Downstream Target Gene for the T/EBP/NKX2.1 Homeodomain Transcription Factor, Encodes Lung- and Stomach-Specific Isoforms through Alternative Splicing", Mol Cell Biol. 2001; 21:7380-7390.
Sahin et al., "Claudin-18 Splice Variant 2 Is a Pan-Cancer Target Suitable for Therapeutic Antibody Development", Hu Cancer Biol. 2008; 14:7624-7634.
Shinozaki et al., "Claudin-18 in biliary neoplasms. Its Significance in the classification of intrahepatic cholangiocarcinoma", Virchows Arch. 2011; 459:73-80.
Singh et al., "Claudin Family of Proteins and Cancer: An Overview", J Oncology 2010; 2010: Article ID 541957 (12 pages).
Tanaka et al., "Claudin-18 Is an Early-Stage Marker of Pancreatic Carcinogenesis", J Histochem Cytochem. 2011; 59:942-952.
Al-Batran Salah-Eddin: "An international, multicenter, randomized, phase II trial of epirubicin, oxaliplatin, and capecitabine (EOX) with or without IMAB362, a first-in-class anti-CLDN18.2 antibody, as first-line therapy in patients with advanced CLDN18.2+ gastric and gastroesophageal junction (GEJ) adenocarcinoma", 2016 ASCO Annual Meeting, vol. 34, Jun. 3, 2016 (Jun. 3, 2016), pp. 1-2, XP055360373, DOI: 10.1200/JC0.2016.34.18 suppl.LBA4001.
Heinz C et al: "Preclinical evaluation of the anti-CLDN18.2 antibody, IMAB362, in pancreatic carcinoma", Annals of Oncology, vol. 28, Sep. 1, 2017 (Sep. 1, 2017), pp. v125-v126, XP055852329, GB, ISSN: 1569-8041, DOI: 10.1093/annonc/mdx367, Retrieved from the Internet: URL:https://www.annalsofoncology.org/action/showPdf?pii=S0923-7534(20)37796-6.

(Continued)

*Primary Examiner* — Ruixiang Li
(74) *Attorney, Agent, or Firm* — Ice Miller LLP

(57) ABSTRACT

Anti-CLDN18.2 antibodies and antigen-binding fragments thereof are described. Also described are nucleic acids encoding the antibodies, compositions comprising the antibodies, and methods of producing the antibodies and using the antibodies for treating or preventing diseases such as cancer and/or an inflammatory disease.

16 Claims, 21 Drawing Sheets

Specification includes a Sequence Listing.

(56) References Cited

OTHER PUBLICATIONS

Julia Holland: "Development of a Highly Potent Bispecific Antibody Format Targeting the Novel Tumor-Specific Antigen CLDN18.2", Dec. 16, 2014 (Dec. 16, 2014), XP055630966, Retrieved from the Internet: URL:https://d-nb.info/1064720994/34 [retrieved on Oct. 10, 2019].

International Preliminary Report on Patentability for PCT/US2019/020872, dated Sep. 8, 2020, 6 pages.

International Search Report and Written Opinion for PCT/US2019/020872, dated May 31, 2019, 9 pages.

Jiang et al., "Claudin 18.2-Specific Chimeric Antigen Receptor Engineered T Cells for the Treatment of Gastric Cancer", Journal of the National Cancer Institute, (20180906), vol. 111, No. 4, pp. 409-418, XP055642983.

Singh et al., "Anti-claudin 18.2 antibody as new targeted therapy for advanced gastric cance", Journal of Hematology & Oncology, (20170512), vol. 10, No. 105, pp. 1-5, XP055630965.

Woll et al., "Claudin 18.2 is a target for IMAB362 antibodyin pancreatic neoplasms", International Journal of Cancer, (20130916), vol. 134, No. 3, pp. 731-739, XP055084209.

Sadilkova et al., "SOT102, a novel CLDN18.2-targeting antibody-drug conjugate with strong therapeutic potential in solid tumors expressing low target levels," American Association for Cancer Research Meeting, Poster No. 1204, Apr. 9-14, 2021.

Zhong et al., "Development of a Humanized VHH Based Recombinant Antibody Targeting Claudin 18.2 Positive Cancers," Frontiers in Immunology, vol. 13, article 885424 (Jun. 28, 2022).

Cao et al., "Claudin18.2 is a novel molecular biomarker for tumor-targeted immunotherapy," Biomarker Research; vol. 10, Issue 38 (2022).

Teng et al., "The Preclinical Characterization of TST001, A Novel Humanized Anti-Claudin18.2 mAb with Enhanced Binding Affinity and Anti-Tumor Activity," Abstract 2148-AACR, American Association for Cancer Research Virtual Meeting, Poster No. 5183, Jun. 22-24, 2020.

Zhang et al., "Evaluation and reflection on claudin 18.2 targeting therapy in advanced gastric cancer," Chinese Journal of Cancer Research, vol. 32, Issue 2, p. 263-270 (2020).

Zhu et al., "Targeting CLDN18.2 by CD3 Bispecific and ADC Modalities for the Treatments of Gastric and Pancreatic Cancer," Scientific Reports, 9(1):8420 (2019).

* cited by examiner

SEQUENCE LISTING

<160> NUMBER OF SEQ ID NOS: 165

<210> SEQ ID NO 1
<211> LENGTH: 118
<212> TYPE: PRT
<213> ORGANISM: Artificial Sequence
<220> FEATURE:
<223> OTHER INFORMATION: 2-C3 Heavy Chain Variable Region

<400> SEQUENCE: 1

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Trp Val
        35                  40                  45

```
Ala Thr Ile Ser Gly Gly Ser Tyr Thr Tyr Tyr Leu Asp Ser Val
         50                  55                  60
Lys Gly Arg Phe Thr Ile Ser Arg Asp Ile Ala Lys Asn Thr Leu Tyr
 65                  70                  75                  80
Leu Gln Met Ser Ser Leu Lys Ser Glu Asp Thr Ala Met Tyr Phe Cys
                 85                  90                  95
Ala Arg Gln Ser Arg Gly Asn Ala Met Asp Tyr Trp Gly Gln Gly Thr
                100                 105                 110
Ser Val Thr Val Ser Ser
            115
```

<210> SEQ ID NO 2
<211> LENGTH: 113
<212> TYPE: PRT
<213> ORGANISM: Artificial Sequence
<220> FEATURE:
<223> OTHER INFORMATION: 2-C3 Light Chain Variable Region

<400> SEQUENCE: 2

```
Asp Ile Val Met Thr Gln Ser Pro Ser Ser Leu Thr Val Thr Ala Gly
 1               5                  10                  15
Glu Lys Val Thr Met Ser Cys Lys Ser Ser Gln Ser Leu Leu Asn Ser
                 20                  25                  30
Gly Asn Gln Lys Asn Tyr Leu Thr Trp Tyr Gln Gln Lys Pro Gly Gln
             35                  40                  45
Pro Pro Lys Leu Leu Ile Tyr Trp Ala Ser Thr Arg Glu Ser Gly Val
 50                  55                  60
Pro Asp Arg Phe Thr Gly Ser Gly Ser Gly Thr Asp Phe Thr Leu Thr
 65                  70                  75                  80
Ile Ser Ser Val Gln Ala Glu Asp Leu Ala Val Tyr Tyr Cys Gln Asn
                 85                  90                  95
Asp Tyr Ser Tyr Pro Leu Thr Phe Gly Ala Gly Thr Lys Leu Glu Leu
                100                 105                 110
Lys
```

<210> SEQ ID NO 3
<211> LENGTH: 117
<212> TYPE: PRT
<213> ORGANISM: Artificial Sequence
<220> FEATURE:
<223> OTHER INFORMATION: 2-P8 Heavy Chain Variable Region

<400> SEQUENCE: 3

```
Glu Val Gln Leu Gln Gln Ser Gly Pro Glu Leu Val Lys Pro Gly Ala
 1               5                  10                  15
Ser Val Lys Met Ser Cys Lys Ala Ser Gly Tyr Ser Phe Thr Gly Tyr
                 20                  25                  30
Asn Met His Trp Val Lys Gln Ser His Gly Lys Ser Leu Glu Trp Ile
             35                  40                  45
Gly Tyr Ile Asp Pro Tyr Asn Gly Val Thr Asn Tyr Asn Gln Lys Phe
 50                  55                  60
Lys Gly Lys Ala Thr Leu Thr Val Asp Lys Ser Ser Ser Thr Ala Tyr
 65                  70                  75                  80
Val Gln Leu Asn Ser Leu Thr Ser Glu Asp Ser Ala Val Tyr Tyr Cys
                 85                  90                  95
```

```
Ala Arg Trp Gly Gly Asn Tyr Val Asp Tyr Trp Gly Gln Gly Thr Thr
            100                 105                 110

Leu Lys Val Ser Ser
        115

<210> SEQ ID NO 4
<211> LENGTH: 107
<212> TYPE: PRT
<213> ORGANISM: Artificial Sequence
<220> FEATURE:
<223> OTHER INFORMATION: 2-P8 Light Chain Variable Region

<400> SEQUENCE: 4

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Arg Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Phe Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Leu
                85                  90                  95

Thr Phe Gly Ala Gly Thr Lys Leu Glu Leu Lys
            100                 105

<210> SEQ ID NO 5
<211> LENGTH: 118
<212> TYPE: PRT
<213> ORGANISM: Artificial Sequence
<220> FEATURE:
<223> OTHER INFORMATION: 3-E21 Heavy Chain Variable Region

<400> SEQUENCE: 5

Glu Val Gln Leu Val Glu Ser Gly Gly Ala Leu Val Lys Pro Gly Gly
1               5                   10                  15

Ser Leu Lys Leu Ser Cys Ala Ala Ser Gly Phe Thr Phe Ser Lys Tyr
            20                  25                  30

Ala Met Ser Trp Val Arg Gln Thr Pro Glu Lys Arg Leu Glu Trp Val
        35                  40                  45

Ala Phe Ile Ser Asn Gly Gly Ser Tyr Thr Tyr Cys Leu Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Leu Tyr Tyr Cys
                85                  90                  95

Ala Arg His Asp Lys Gly Asn Ala Leu Asp Tyr Trp Gly Gln Gly Asn
            100                 105                 110

Ser Val Thr Val Ser Ser
        115

<210> SEQ ID NO 6
<211> LENGTH: 113
<212> TYPE: PRT
<213> ORGANISM: Artificial Sequence
<220> FEATURE:
<223> OTHER INFORMATION: 3-E21 Light Chain Variable Region
```

<400> SEQUENCE: 6

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ser Val Tyr Tyr Cys Gln Asn
                85                  90                  95

Asp Tyr Phe Tyr Pro Leu Thr Phe Gly Ala Gly Thr Lys Leu Glu Leu
            100                 105                 110

Lys

<210> SEQ ID NO 7
<211> LENGTH: 119
<212> TYPE: PRT
<213> ORGANISM: Artificial Sequence
<220> FEATURE:
<223> OTHER INFORMATION: 3-P21 Heavy Chain Variable Region

<400> SEQUENCE: 7

Glu Ile Gln Leu Gln Gln Ser Gly Ala Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Asn Met Lys Trp Val Lys Gln Ser His Gly Lys Ser Leu Glu Trp Ile
        35                  40                  45

Gly Asn Ile Asn Pro Tyr Phe Gly Ser Thr Asn Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Gly Ala Tyr Tyr Gly Asn Ala Met Asp Tyr Trp Gly Gln Gly
            100                 105                 110

Thr Ser Val Thr Val Ser Ser
        115

<210> SEQ ID NO 8
<211> LENGTH: 113
<212> TYPE: PRT
<213> ORGANISM: Artificial Sequence
<220> FEATURE:
<223> OTHER INFORMATION: 3-P21 Light Chain Variable Region

<400> SEQUENCE: 8

Asp Ile Val Met Thr Gln Ser Pro Ser Ser Leu Thr Val Thr Ala Gly
1               5                   10                  15

Gly Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
            50                  55                  60

Pro Asp Arg Phe Ser Gly Ser Gly Ser Gly Thr Asp Phe Thr Leu Thr
 65                  70                  75                  80

Ile Ser Ser Val Gln Ala Glu Asp Leu Ala Val Tyr Tyr Cys Gln Asn
                    85                  90                  95

Asp Tyr Phe Tyr Pro Leu Thr Phe Gly Ala Gly Thr Lys Leu Glu Leu
                100                 105                 110

Lys

<210> SEQ ID NO 9
<211> LENGTH: 118
<212> TYPE: PRT
<213> ORGANISM: Artificial Sequence
<220> FEATURE:
<223> OTHER INFORMATION: 5-E22 Heavy Chain Variable Region

<400> SEQUENCE: 9

Lys Val Gln Leu Gln Gln Ser Gly Pro Asp Leu Val Glu Pro Gly Ala
 1               5                  10                  15

Ser Val Lys Ile Ser Cys Lys Ala Ser Gly Tyr Thr Ile Thr Asp Asn
                20                  25                  30

Tyr Met His Trp Val Lys Gln Lys Pro Gly Gln Gly Leu Glu Trp Ile
            35                  40                  45

Gly Glu Ile Tyr Pro Gly Ser Gly Asn Thr Tyr Tyr Asn Glu Arg Phe
        50                  55                  60

Lys Gly Lys Ala Thr Leu Thr Ala Asp Lys Ser Ser Ser Thr Ala Tyr
 65                  70                  75                  80

Met Gln Leu Ser Ser Leu Thr Ser Glu Asp Ser Ala Val Tyr Phe Cys
                85                  90                  95

Ala Arg Gly Phe Pro Tyr Tyr Ala Met Asp Tyr Trp Gly Pro Gly Thr
                100                 105                 110

Ser Val Thr Val Ser Ser
        115

<210> SEQ ID NO 10
<211> LENGTH: 107
<212> TYPE: PRT
<213> ORGANISM: Artificial Sequence
<220> FEATURE:
<223> OTHER INFORMATION: 5-E22 Light Chain Variable Region

<400> SEQUENCE: 10

Asp Ile Gln Met Asn Gln Ser Pro Ser Ser Leu Ser Ala Ser Leu Gly
 1               5                  10                  15

Asp Thr Ile Thr Ile Thr Cys His Ala Arg Gln Asn Ile Asn Val Trp
                20                  25                  30

Leu Ser Trp Tyr Gln Gln Lys Ser Gly Asn Ile Pro Lys Leu Leu Ile
            35                  40                  45

Tyr Lys Ala Ser Asn Leu His Thr Gly Val Pro Ser Arg Phe Ser Gly
        50                  55                  60

Ser Gly Ser Gly Thr Arg Phe Thr Leu Thr Ile Ser Ser Leu Gln Pro
 65                  70                  75                  80

Glu Asp Met Ala Thr Tyr Tyr Cys Gln Gln Gly Gln Asn Tyr Pro Leu
                85                  90                  95

Thr Phe Gly Gly Gly Thr Lys Leu Glu Ile Lys
                100                 105

-continued

```
<210> SEQ ID NO 11
<211> LENGTH: 119
<212> TYPE: PRT
<213> ORGANISM: Artificial Sequence
<220> FEATURE:
<223> OTHER INFORMATION: 6-J11 Heavy Chain Variable Region

<400> SEQUENCE: 11
```

Asp Val Gln Leu Val Glu Ser Gly Gly Leu Val Gln Pro Gly Gly
1               5                   10                  15

Ser Arg Lys Leu Ser Cys Ala Ala Ser Gly Phe Ile Phe Ser Ser Phe
            20                  25                  30

Gly Met His Trp Val Arg Gln Ala Pro Glu Lys Gly Leu Glu Trp Val
        35                  40                  45

Ala Tyr Ile Ser Ser Gly Arg Ser Thr Met Tyr Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Gly Gly Phe Tyr Gly Asn Ser Leu Asp Tyr Trp Gly Gln Gly
            100                 105                 110

Thr Ser Val Thr Val Ser Ser
        115

```
<210> SEQ ID NO 12
<211> LENGTH: 113
<212> TYPE: PRT
<213> ORGANISM: Artificial Sequence
<220> FEATURE:
<223> OTHER INFORMATION: 6-J11 Light Chain Variable Region

<400> SEQUENCE: 12
```

Asp Ile Val Met Thr Gln Ser Pro Ser Ser Leu Thr Val Thr Ala Gly
1               5                   10                  15

Glu Lys Val Thr Met Ser Cys Lys Ser Ser Leu Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Met Gln Ala Glu Asp Leu Ala Val Tyr Ser Cys Gln Asn
                85                  90                  95

Ala Tyr Ser Tyr Pro Leu Thr Phe Gly Ala Gly Thr Lys Leu Glu Leu
            100                 105                 110

Lys

```
<210> SEQ ID NO 13
<211> LENGTH: 119
<212> TYPE: PRT
<213> ORGANISM: Artificial Sequence
<220> FEATURE:
<223> OTHER INFORMATION: 8-G12 Heavy Chain Variable Region

<400> SEQUENCE: 13
```

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Asp Tyr
            20                  25                  30

Trp Met Asn Trp Val Lys Gln Arg Pro Gly Lys Gly Leu Glu Trp Ile
        35                  40                  45

Gly Gln Ile Tyr Pro Tyr Gly Asp Thr Lys Tyr Asn Glu Asn Phe
50                  55                  60

Lys Gly Thr Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Trp Gly Tyr Tyr Gly Asn Ala Met Asp Tyr Trp Gly Gln Gly
            100                 105                 110

Thr Ser Val Thr Val Ser Ser
        115

<210> SEQ ID NO 14
<211> LENGTH: 113
<212> TYPE: PRT
<213> ORGANISM: Artificial Sequence
<220> FEATURE:
<223> OTHER INFORMATION: 8-G12 Light Chain Variable Region

<400> SEQUENCE: 14

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Thr Glu Asp Leu Ala Ile Tyr Tyr Cys Gln Asn
                85                  90                  95

Ala Tyr Ile Tyr Pro Leu Thr Phe Gly Ala Gly Thr Lys Leu Glu Leu
            100                 105                 110

Lys

<210> SEQ ID NO 15
<211> LENGTH: 118
<212> TYPE: PRT
<213> ORGANISM: Artificial Sequence
<220> FEATURE:
<223> OTHER INFORMATION: 10-J10 Heavy Chain Variable Region

<400> SEQUENCE: 15

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Arg Tyr
            20                  25                  30

Arg Met Asn Trp Val Lys Gln Arg Pro Gly Gln Gly Leu Glu Trp Ile
        35                  40                  45

Gly Asn Ile Asp Pro Ser Asp Ser Glu Thr His Tyr Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Phe Tyr Cys
            85                  90                  95

Ala Arg Leu Asn Tyr Gly Asn Cys Phe Asp Tyr Trp Gly Gln Gly Thr
            100                 105                 110

Thr Leu Thr Val Ser Ser
        115

<210> SEQ ID NO 16
<211> LENGTH: 113
<212> TYPE: PRT
<213> ORGANISM: Artificial Sequence
<220> FEATURE:
<223> OTHER INFORMATION: 10-J10 Light Chain Variable Region

<400> SEQUENCE: 16

Asp Ile Val Met Thr Gln Ser Pro Ser Ser Leu Thr Val Thr Ala Gly
1               5                   10                  15

Glu Lys Val Thr Met Ser Cys Lys Ser Ser Gln Thr Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Phe Tyr Cys Gln Asn
            85                  90                  95

Asp Tyr Phe Tyr Pro Phe Thr Phe Gly Ser Gly Thr Lys Leu Glu Ile
            100                 105                 110

Lys

<210> SEQ ID NO 17
<211> LENGTH: 118
<212> TYPE: PRT
<213> ORGANISM: Artificial Sequence
<220> FEATURE:
<223> OTHER INFORMATION: 10-K2 Heavy Chain Variable Region

<400> SEQUENCE: 17

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Ala Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Ser Asp Gly Thr Arg Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
            85                  90                  95

Thr Arg Ile Tyr Tyr Gly Asn Ala Met Asp Tyr Trp Gly Gln Gly Thr
            100                 105                 110

Ser Val Thr Val Ser Ser
        115

<210> SEQ ID NO 18

-continued

```
<211> LENGTH: 113
<212> TYPE: PRT
<213> ORGANISM: Artificial Sequence
<220> FEATURE:
<223> OTHER INFORMATION: 10-K2 Light Chain Variable Region

<400> SEQUENCE: 18

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Phe Thr Phe Gly Ser Gly Thr Lys Leu Glu Ile
            100                 105                 110

Lys

<210> SEQ ID NO 19
<211> LENGTH: 118
<212> TYPE: PRT
<213> ORGANISM: Artificial Sequence
<220> FEATURE:
<223> OTHER INFORMATION: 15-D6 Heavy Chain Variable Region

<400> SEQUENCE: 19

Gln Val Gln Leu Gln Gln Pro Gly Ala Asp Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
        35                  40                  45

Gly Asn Ile Tyr Pro Gly Arg Ser Ser Thr Asn Tyr Asn Glu Lys Phe
    50                  55                  60

Lys Ser Lys Ala Thr Leu Thr Val Asp Thr Ser Ser Ser Thr Ala Tyr
65                  70                  75                  80

Met Gln Leu Ser Ser Leu Ala Ser Asp Ser Ala Val Tyr Tyr Cys
                85                  90                  95

Ser Arg Leu Ser Arg Gly Asn Ala Met Asp Tyr Trp Gly Gln Gly Thr
            100                 105                 110

Ser Val Thr Val Ser Ser
        115

<210> SEQ ID NO 20
<211> LENGTH: 113
<212> TYPE: PRT
<213> ORGANISM: Artificial Sequence
<220> FEATURE:
<223> OTHER INFORMATION: 15-D6 Light Chain Variable Region

<400> SEQUENCE: 20

Asp Ile Val Met Thr Gln Ser Pro Ser Ser Leu Thr Val Thr Ala Gly
1               5                   10                  15
```

-continued

Glu Lys Val Thr Met Ser Cys Arg Ser Ser Gln Ser Leu Leu Asn Ser
            20                  25                  30

Gly Asn Gln Lys Ser Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Cys Gln Asn
                85                  90                  95

Asp Tyr Tyr Tyr Pro Phe Thr Phe Gly Ser Gly Thr Lys Leu Glu Ile
            100                 105                 110

Lys

<210> SEQ ID NO 21
<211> LENGTH: 8
<212> TYPE: PRT
<213> ORGANISM: Artificial Sequence
<220> FEATURE:
<223> OTHER INFORMATION: 2-C3 HC CDR1

<400> SEQUENCE: 21

Gly Phe Thr Phe Ser Ser Tyr Gly
1               5

<210> SEQ ID NO 22
<211> LENGTH: 8
<212> TYPE: PRT
<213> ORGANISM: Artificial Sequence
<220> FEATURE:
<223> OTHER INFORMATION: 2-C3 HC CDR2

<400> SEQUENCE: 22

Ile Ser Gly Gly Gly Ser Tyr Thr
1               5

<210> SEQ ID NO 23
<211> LENGTH: 11
<212> TYPE: PRT
<213> ORGANISM: Artificial Sequence
<220> FEATURE:
<223> OTHER INFORMATION: 2-C3 HC CDR3

<400> SEQUENCE: 23

Ala Arg Gln Ser Arg Gly Asn Ala Met Asp Tyr
1               5                   10

<210> SEQ ID NO 24
<211> LENGTH: 8
<212> TYPE: PRT
<213> ORGANISM: Artificial Sequence
<220> FEATURE:
<223> OTHER INFORMATION: 2-P8 HC CDR1

<400> SEQUENCE: 24

Gly Tyr Ser Phe Thr Gly Tyr Asn
1               5

<210> SEQ ID NO 25
<211> LENGTH: 8
<212> TYPE: PRT
<213> ORGANISM: Artificial Sequence
<220> FEATURE:

<223> OTHER INFORMATION: 2-P8 HC CDR2

<400> SEQUENCE: 25

Ile Asp Pro Tyr Asn Gly Val Thr
1               5

<210> SEQ ID NO 26
<211> LENGTH: 10
<212> TYPE: PRT
<213> ORGANISM: Artificial Sequence
<220> FEATURE:
<223> OTHER INFORMATION: 2-P8 HC CDR3

<400> SEQUENCE: 26

Ala Arg Trp Gly Gly Asn Tyr Val Asp Tyr
1               5                   10

<210> SEQ ID NO 27
<211> LENGTH: 8
<212> TYPE: PRT
<213> ORGANISM: Artificial Sequence
<220> FEATURE:
<223> OTHER INFORMATION: 3-E21 HC CDR1

<400> SEQUENCE: 27

Gly Phe Thr Phe Ser Lys Tyr Ala
1               5

<210> SEQ ID NO 28
<211> LENGTH: 8
<212> TYPE: PRT
<213> ORGANISM: Artificial Sequence
<220> FEATURE:
<223> OTHER INFORMATION: 3-E21 HC CDR2

<400> SEQUENCE: 28

Ile Ser Asn Gly Gly Ser Tyr Thr
1               5

<210> SEQ ID NO 29
<211> LENGTH: 11
<212> TYPE: PRT
<213> ORGANISM: Artificial Sequence
<220> FEATURE:
<223> OTHER INFORMATION: 3-E21 HC CDR3

<400> SEQUENCE: 29

Ala Arg His Asp Lys Gly Asn Ala Leu Asp Tyr
1               5                   10

<210> SEQ ID NO 30
<211> LENGTH: 8
<212> TYPE: PRT
<213> ORGANISM: Artificial Sequence
<220> FEATURE:
<223> OTHER INFORMATION: 3-P21 HC CDR1

<400> SEQUENCE: 30

Gly Tyr Ser Phe Thr Gly Tyr Asn
1               5

<210> SEQ ID NO 31
<211> LENGTH: 8
<212> TYPE: PRT
<213> ORGANISM: Artificial Sequence
<220> FEATURE:
<223> OTHER INFORMATION: 3-P21 HC CDR2

```
<400> SEQUENCE: 31

Ile Asn Pro Tyr Phe Gly Ser Thr
1               5

<210> SEQ ID NO 32
<211> LENGTH: 12
<212> TYPE: PRT
<213> ORGANISM: Artificial Sequence
<220> FEATURE:
<223> OTHER INFORMATION: 3-P21 HC CDR3

<400> SEQUENCE: 32

Ala Arg Gly Ala Tyr Tyr Gly Asn Ala Met Asp Tyr
1               5                   10

<210> SEQ ID NO 33
<211> LENGTH: 8
<212> TYPE: PRT
<213> ORGANISM: Artificial Sequence
<220> FEATURE:
<223> OTHER INFORMATION: 5-E22 HC CDR1

<400> SEQUENCE: 33

Gly Tyr Thr Ile Thr Asp Asn Tyr
1               5

<210> SEQ ID NO 34
<211> LENGTH: 8
<212> TYPE: PRT
<213> ORGANISM: Artificial Sequence
<220> FEATURE:
<223> OTHER INFORMATION: 5-E22 HC CDR2

<400> SEQUENCE: 34

Ile Tyr Pro Gly Ser Gly Asn Thr
1               5

<210> SEQ ID NO 35
<211> LENGTH: 11
<212> TYPE: PRT
<213> ORGANISM: Artificial Sequence
<220> FEATURE:
<223> OTHER INFORMATION: 5-E22 HC CDR3

<400> SEQUENCE: 35

Ala Arg Gly Phe Pro Tyr Tyr Ala Met Asp Tyr
1               5                   10

<210> SEQ ID NO 36
<211> LENGTH: 8
<212> TYPE: PRT
<213> ORGANISM: Artificial Sequence
<220> FEATURE:
<223> OTHER INFORMATION: 6-J11 HC CDR1

<400> SEQUENCE: 36

Gly Phe Ile Phe Ser Ser Phe Gly
1               5

<210> SEQ ID NO 37
<211> LENGTH: 8
<212> TYPE: PRT
<213> ORGANISM: Artificial Sequence
<220> FEATURE:
<223> OTHER INFORMATION: 6-J11 HC CDR2
```

```
<400> SEQUENCE: 37

Ile Ser Ser Gly Arg Ser Thr Met
1               5

<210> SEQ ID NO 38
<211> LENGTH: 12
<212> TYPE: PRT
<213> ORGANISM: Artificial Sequence
<220> FEATURE:
<223> OTHER INFORMATION: 6-J11 HC CDR3

<400> SEQUENCE: 38

Ala Arg Gly Gly Phe Tyr Gly Asn Ser Leu Asp Tyr
1               5                   10

<210> SEQ ID NO 39
<211> LENGTH: 8
<212> TYPE: PRT
<213> ORGANISM: Artificial Sequence
<220> FEATURE:
<223> OTHER INFORMATION: 8-G12 HC CDR1

<400> SEQUENCE: 39

Gly Tyr Ala Phe Ser Asp Tyr Trp
1               5

<210> SEQ ID NO 40
<211> LENGTH: 8
<212> TYPE: PRT
<213> ORGANISM: Artificial Sequence
<220> FEATURE:
<223> OTHER INFORMATION: 8-G12 HC CDR2

<400> SEQUENCE: 40

Ile Tyr Pro Gly Tyr Gly Asp Thr
1               5

<210> SEQ ID NO 41
<211> LENGTH: 12
<212> TYPE: PRT
<213> ORGANISM: Artificial Sequence
<220> FEATURE:
<223> OTHER INFORMATION: 8-G12 HC CDR3

<400> SEQUENCE: 41

Ala Arg Trp Gly Tyr Tyr Gly Asn Ala Met Asp Tyr
1               5                   10

<210> SEQ ID NO 42
<211> LENGTH: 8
<212> TYPE: PRT
<213> ORGANISM: Artificial Sequence
<220> FEATURE:
<223> OTHER INFORMATION: 10-J10 HC CDR1

<400> SEQUENCE: 42

Gly Tyr Thr Phe Thr Arg Tyr Arg
1               5

<210> SEQ ID NO 43
<211> LENGTH: 8
<212> TYPE: PRT
<213> ORGANISM: Artificial Sequence
<220> FEATURE:
<223> OTHER INFORMATION: 10-J10 HC CDR2
```

```
<400> SEQUENCE: 43

Ile Asp Pro Ser Asp Ser Glu Thr
1               5

<210> SEQ ID NO 44
<211> LENGTH: 11
<212> TYPE: PRT
<213> ORGANISM: Artificial Sequence
<220> FEATURE:
<223> OTHER INFORMATION: 10-J10 HC CDR3

<400> SEQUENCE: 44

Ala Arg Leu Asn Tyr Gly Asn Cys Phe Asp Tyr
1               5                   10

<210> SEQ ID NO 45
<211> LENGTH: 8
<212> TYPE: PRT
<213> ORGANISM: Artificial Sequence
<220> FEATURE:
<223> OTHER INFORMATION: 10-K2 HC CDR1

<400> SEQUENCE: 45

Gly Tyr Ala Phe Thr Ser Tyr Val
1               5

<210> SEQ ID NO 46
<211> LENGTH: 8
<212> TYPE: PRT
<213> ORGANISM: Artificial Sequence
<220> FEATURE:
<223> OTHER INFORMATION: 10-K2 HC CDR2

<400> SEQUENCE: 46

Ile Asn Pro Tyr Ser Asp Gly Thr
1               5

<210> SEQ ID NO 47
<211> LENGTH: 11
<212> TYPE: PRT
<213> ORGANISM: Artificial Sequence
<220> FEATURE:
<223> OTHER INFORMATION: 10-K2 HC CDR3

<400> SEQUENCE: 47

Thr Arg Ile Tyr Tyr Gly Asn Ala Met Asp Tyr
1               5                   10

<210> SEQ ID NO 48
<211> LENGTH: 8
<212> TYPE: PRT
<213> ORGANISM: Artificial Sequence
<220> FEATURE:
<223> OTHER INFORMATION: 15-D6 HC CDR1

<400> SEQUENCE: 48

Gly Tyr Thr Phe Thr Ser Tyr Trp
1               5

<210> SEQ ID NO 49
<211> LENGTH: 8
<212> TYPE: PRT
<213> ORGANISM: Artificial Sequence
<220> FEATURE:
<223> OTHER INFORMATION: 15-D6 HC CDR2
```

```
<400> SEQUENCE: 49

Ile Tyr Pro Gly Arg Ser Ser Thr
1               5

<210> SEQ ID NO 50
<211> LENGTH: 11
<212> TYPE: PRT
<213> ORGANISM: Artificial Sequence
<220> FEATURE:
<223> OTHER INFORMATION: 15-D6 HC CDR3

<400> SEQUENCE: 50

Ser Arg Leu Ser Arg Gly Asn Ala Met Asp Tyr
1               5                   10

<210> SEQ ID NO 51
<211> LENGTH: 12
<212> TYPE: PRT
<213> ORGANISM: Artificial Sequence
<220> FEATURE:
<223> OTHER INFORMATION: 2-C3 LC CDR1

<400> SEQUENCE: 51

Gln Ser Leu Leu Asn Ser Gly Asn Gln Lys Asn Tyr
1               5                   10

<210> SEQ ID NO 52
<211> LENGTH: 3
<212> TYPE: PRT
<213> ORGANISM: Artificial Sequence
<220> FEATURE:
<223> OTHER INFORMATION: 2-C3 LC CDR2

<400> SEQUENCE: 52

Trp Ala Ser
1

<210> SEQ ID NO 53
<211> LENGTH: 9
<212> TYPE: PRT
<213> ORGANISM: Artificial Sequence
<220> FEATURE:
<223> OTHER INFORMATION: 2-C3 LC CDR3

<400> SEQUENCE: 53

Gln Asn Asp Tyr Ser Tyr Pro Leu Thr
1               5

<210> SEQ ID NO 54
<211> LENGTH: 6
<212> TYPE: PRT
<213> ORGANISM: Artificial Sequence
<220> FEATURE:
<223> OTHER INFORMATION: 2-P8 LC CDR1

<400> SEQUENCE: 54

Gln Asp Ile Asn Arg Tyr
1               5

<210> SEQ ID NO 55
<211> LENGTH: 3
<212> TYPE: PRT
<213> ORGANISM: Artificial Sequence
<220> FEATURE:
<223> OTHER INFORMATION: 2-P8 LC CDR2
```

```
<400> SEQUENCE: 55

Arg Ala Asn
1

<210> SEQ ID NO 56
<211> LENGTH: 9
<212> TYPE: PRT
<213> ORGANISM: Artificial Sequence
<220> FEATURE:
<223> OTHER INFORMATION: 2-P8 LC CDR3

<400> SEQUENCE: 56

Leu Gln Tyr Asp Glu Phe Pro Leu Thr
1               5

<210> SEQ ID NO 57
<211> LENGTH: 12
<212> TYPE: PRT
<213> ORGANISM: Artificial Sequence
<220> FEATURE:
<223> OTHER INFORMATION: 3-E21 LC CDR1

<400> SEQUENCE: 57

Gln Ser Leu Leu Asn Ser Gly Asn Gln Lys Asn Tyr
1               5                   10

<210> SEQ ID NO 58
<211> LENGTH: 3
<212> TYPE: PRT
<213> ORGANISM: Artificial Sequence
<220> FEATURE:
<223> OTHER INFORMATION: 3-E21 LC CDR2

<400> SEQUENCE: 58

Trp Ala Ser
1

<210> SEQ ID NO 59
<211> LENGTH: 9
<212> TYPE: PRT
<213> ORGANISM: Artificial Sequence
<220> FEATURE:
<223> OTHER INFORMATION: 3-E21 LC CDR3

<400> SEQUENCE: 59

Gln Asn Asp Tyr Phe Tyr Pro Leu Thr
1               5

<210> SEQ ID NO 60
<211> LENGTH: 12
<212> TYPE: PRT
<213> ORGANISM: Artificial Sequence
<220> FEATURE:
<223> OTHER INFORMATION: 3-P21 LC CDR1

<400> SEQUENCE: 60

Gln Ser Leu Leu Asn Ser Gly Asn Gln Lys Asn Tyr
1               5                   10

<210> SEQ ID NO 61
<211> LENGTH: 3
<212> TYPE: PRT
<213> ORGANISM: Artificial Sequence
<220> FEATURE:
<223> OTHER INFORMATION: 3-P21 LC CDR2
```

```
<400> SEQUENCE: 61

Trp Ala Ser
1

<210> SEQ ID NO 62
<211> LENGTH: 9
<212> TYPE: PRT
<213> ORGANISM: Artificial Sequence
<220> FEATURE:
<223> OTHER INFORMATION: 3-P21 LC CDR3

<400> SEQUENCE: 62

Gln Asn Asp Tyr Phe Tyr Pro Leu Thr
1               5

<210> SEQ ID NO 63
<211> LENGTH: 6
<212> TYPE: PRT
<213> ORGANISM: Artificial Sequence
<220> FEATURE:
<223> OTHER INFORMATION: 5-E22 LC CDR1

<400> SEQUENCE: 63

Gln Asn Ile Asn Val Trp
1               5

<210> SEQ ID NO 64
<211> LENGTH: 3
<212> TYPE: PRT
<213> ORGANISM: Artificial Sequence
<220> FEATURE:
<223> OTHER INFORMATION: 5-E22 LC CDR2

<400> SEQUENCE: 64

Lys Ala Ser
1

<210> SEQ ID NO 65
<211> LENGTH: 9
<212> TYPE: PRT
<213> ORGANISM: Artificial Sequence
<220> FEATURE:
<223> OTHER INFORMATION: 5-E22 LC CDR3

<400> SEQUENCE: 65

Gln Gln Gly Gln Asn Tyr Pro Leu Thr
1               5

<210> SEQ ID NO 66
<211> LENGTH: 12
<212> TYPE: PRT
<213> ORGANISM: Artificial Sequence
<220> FEATURE:
<223> OTHER INFORMATION: 6-J11 LC CDR1

<400> SEQUENCE: 66

Leu Ser Leu Leu Asn Ser Gly Asn Gln Lys Asn Tyr
1               5                   10

<210> SEQ ID NO 67
<211> LENGTH: 3
<212> TYPE: PRT
<213> ORGANISM: Artificial Sequence
<220> FEATURE:
<223> OTHER INFORMATION: 6-J11 LC CDR2
```

```
<400> SEQUENCE: 67

Trp Ala Ser
1

<210> SEQ ID NO 68
<211> LENGTH: 9
<212> TYPE: PRT
<213> ORGANISM: Artificial Sequence
<220> FEATURE:
<223> OTHER INFORMATION: 6-J11 LC CDR3

<400> SEQUENCE: 68

Gln Asn Ala Tyr Ser Tyr Pro Leu Thr
1               5

<210> SEQ ID NO 69
<211> LENGTH: 12
<212> TYPE: PRT
<213> ORGANISM: Artificial Sequence
<220> FEATURE:
<223> OTHER INFORMATION: 8-G12 LC CDR1

<400> SEQUENCE: 69

Gln Ser Leu Leu Asn Ser Gly Asn Gln Lys Asn Tyr
1               5                   10

<210> SEQ ID NO 70
<211> LENGTH: 3
<212> TYPE: PRT
<213> ORGANISM: Artificial Sequence
<220> FEATURE:
<223> OTHER INFORMATION: 8-G12 LC CDR2

<400> SEQUENCE: 70

Trp Ala Ser
1

<210> SEQ ID NO 71
<211> LENGTH: 9
<212> TYPE: PRT
<213> ORGANISM: Artificial Sequence
<220> FEATURE:
<223> OTHER INFORMATION: 8-G12 LC CDR3

<400> SEQUENCE: 71

Gln Asn Ala Tyr Ile Tyr Pro Leu Thr
1               5

<210> SEQ ID NO 72
<211> LENGTH: 12
<212> TYPE: PRT
<213> ORGANISM: Artificial Sequence
<220> FEATURE:
<223> OTHER INFORMATION: 10-J10 LC CDR1

<400> SEQUENCE: 72

Gln Thr Leu Leu Asn Ser Gly Asn Gln Lys Asn Tyr
1               5                   10

<210> SEQ ID NO 73
<211> LENGTH: 3
<212> TYPE: PRT
<213> ORGANISM: Artificial Sequence
<220> FEATURE:
<223> OTHER INFORMATION: 10-J10 LC CDR2
```

<400> SEQUENCE: 73

Trp Ala Ser
1

<210> SEQ ID NO 74
<211> LENGTH: 9
<212> TYPE: PRT
<213> ORGANISM: Artificial Sequence
<220> FEATURE:
<223> OTHER INFORMATION: 10-J10 LC CDR3

<400> SEQUENCE: 74

Gln Asn Asp Tyr Phe Tyr Pro Phe Thr
1               5

<210> SEQ ID NO 75
<211> LENGTH: 12
<212> TYPE: PRT
<213> ORGANISM: Artificial Sequence
<220> FEATURE:
<223> OTHER INFORMATION: 10-K2 LC CDR1

<400> SEQUENCE: 75

Gln Ser Leu Leu Asn Ser Gly Asn Gln Lys Asn Tyr
1               5                   10

<210> SEQ ID NO 76
<211> LENGTH: 3
<212> TYPE: PRT
<213> ORGANISM: Artificial Sequence
<220> FEATURE:
<223> OTHER INFORMATION: 10-K2 LC CDR2

<400> SEQUENCE: 76

Trp Ala Ser
1

<210> SEQ ID NO 77
<211> LENGTH: 9
<212> TYPE: PRT
<213> ORGANISM: Artificial Sequence
<220> FEATURE:
<223> OTHER INFORMATION: 10-K2 LC CDR3

<400> SEQUENCE: 77

Gln Asn Asp Tyr Ser Tyr Pro Phe Thr
1               5

<210> SEQ ID NO 78
<211> LENGTH: 12
<212> TYPE: PRT
<213> ORGANISM: Artificial Sequence
<220> FEATURE:
<223> OTHER INFORMATION: 15-D6 LC CDR1

<400> SEQUENCE: 78

Gln Ser Leu Leu Asn Ser Gly Asn Gln Lys Ser Tyr
1               5                   10

<210> SEQ ID NO 79
<211> LENGTH: 3
<212> TYPE: PRT
<213> ORGANISM: Artificial Sequence
<220> FEATURE:
<223> OTHER INFORMATION: 15-D6 LC CDR2

```
<400> SEQUENCE: 79

Trp Ala Ser
1

<210> SEQ ID NO 80
<211> LENGTH: 9
<212> TYPE: PRT
<213> ORGANISM: Artificial Sequence
<220> FEATURE:
<223> OTHER INFORMATION: 15-D6 LC CDR3

<400> SEQUENCE: 80

Gln Asn Asp Tyr Tyr Tyr Pro Phe Thr
1               5

<210> SEQ ID NO 81
<211> LENGTH: 10
<212> TYPE: PRT
<213> ORGANISM: Artificial Sequence
<220> FEATURE:
<223> OTHER INFORMATION: 2-C3 HC CDR1

<400> SEQUENCE: 81

Gly Phe Thr Phe Ser Ser Tyr Gly Met Ser
1               5                   10

<210> SEQ ID NO 82
<211> LENGTH: 17
<212> TYPE: PRT
<213> ORGANISM: Artificial Sequence
<220> FEATURE:
<223> OTHER INFORMATION: 2-C3 HC CDR2

<400> SEQUENCE: 82

Thr Ile Ser Gly Gly Gly Ser Tyr Thr Tyr Tyr Leu Asp Ser Val Lys
1               5                   10                  15

Gly

<210> SEQ ID NO 83
<211> LENGTH: 11
<212> TYPE: PRT
<213> ORGANISM: Artificial Sequence
<220> FEATURE:
<223> OTHER INFORMATION: 2-C3 HC CDR3

<400> SEQUENCE: 83

Ala Arg Gln Ser Arg Gly Asn Ala Met Asp Tyr
1               5                   10

<210> SEQ ID NO 84
<211> LENGTH: 10
<212> TYPE: PRT
<213> ORGANISM: Artificial Sequence
<220> FEATURE:
<223> OTHER INFORMATION: 2-P8 HC CDR1

<400> SEQUENCE: 84

Gly Tyr Ser Phe Thr Gly Tyr Asn Met His
1               5                   10

<210> SEQ ID NO 85
<211> LENGTH: 17
<212> TYPE: PRT
<213> ORGANISM: Artificial Sequence
<220> FEATURE:
```

<223> OTHER INFORMATION: 2-P8 HC CDR2

<400> SEQUENCE: 85

Tyr Ile Asp Pro Tyr Asn Gly Val Thr Asn Tyr Asn Gln Lys Phe Lys
1               5                   10                  15
Gly

<210> SEQ ID NO 86
<211> LENGTH: 10
<212> TYPE: PRT
<213> ORGANISM: Artificial Sequence
<220> FEATURE:
<223> OTHER INFORMATION: 2-P8 HC CDR3

<400> SEQUENCE: 86

Ala Arg Trp Gly Gly Asn Tyr Val Asp Tyr
1               5                   10

<210> SEQ ID NO 87
<211> LENGTH: 10
<212> TYPE: PRT
<213> ORGANISM: Artificial Sequence
<220> FEATURE:
<223> OTHER INFORMATION: 3-E21 HC CDR1

<400> SEQUENCE: 87

Gly Phe Thr Phe Ser Lys Tyr Ala Met Ser
1               5                   10

<210> SEQ ID NO 88
<211> LENGTH: 17
<212> TYPE: PRT
<213> ORGANISM: Artificial Sequence
<220> FEATURE:
<223> OTHER INFORMATION: 3-E21 HC CDR2

<400> SEQUENCE: 88

Phe Ile Ser Asn Gly Gly Ser Tyr Thr Tyr Cys Leu Asp Ser Val Lys
1               5                   10                  15
Gly

<210> SEQ ID NO 89
<211> LENGTH: 11
<212> TYPE: PRT
<213> ORGANISM: Artificial Sequence
<220> FEATURE:
<223> OTHER INFORMATION: 3-E21 HC CDR3

<400> SEQUENCE: 89

Ala Arg His Asp Lys Gly Asn Ala Leu Asp Tyr
1               5                   10

<210> SEQ ID NO 90
<211> LENGTH: 10
<212> TYPE: PRT
<213> ORGANISM: Artificial Sequence
<220> FEATURE:
<223> OTHER INFORMATION: 3-P21 HC CDR1

<400> SEQUENCE: 90

Gly Tyr Ser Phe Thr Gly Tyr Asn Met Lys
1               5                   10

<210> SEQ ID NO 91
<211> LENGTH: 17

```
<212> TYPE: PRT
<213> ORGANISM: Artificial Sequence
<220> FEATURE:
<223> OTHER INFORMATION: 3-P21 HC CDR2

<400> SEQUENCE: 91

Asn Ile Asn Pro Tyr Phe Gly Ser Thr Asn Tyr Asn Gln Lys Phe Lys
1               5                   10                  15
Gly

<210> SEQ ID NO 92
<211> LENGTH: 12
<212> TYPE: PRT
<213> ORGANISM: Artificial Sequence
<220> FEATURE:
<223> OTHER INFORMATION: 3-P21 HC CDR3

<400> SEQUENCE: 92

Ala Arg Gly Ala Tyr Tyr Gly Asn Ala Met Asp Tyr
1               5                   10

<210> SEQ ID NO 93
<211> LENGTH: 10
<212> TYPE: PRT
<213> ORGANISM: Artificial Sequence
<220> FEATURE:
<223> OTHER INFORMATION: 5-E22 HC CDR1

<400> SEQUENCE: 93

Gly Tyr Thr Ile Thr Asp Asn Tyr Met His
1               5                   10

<210> SEQ ID NO 94
<211> LENGTH: 17
<212> TYPE: PRT
<213> ORGANISM: Artificial Sequence
<220> FEATURE:
<223> OTHER INFORMATION: 5-E22 HC CDR2

<400> SEQUENCE: 94

Glu Ile Tyr Pro Gly Ser Gly Asn Thr Tyr Tyr Asn Glu Arg Phe Lys
1               5                   10                  15
Gly

<210> SEQ ID NO 95
<211> LENGTH: 11
<212> TYPE: PRT
<213> ORGANISM: Artificial Sequence
<220> FEATURE:
<223> OTHER INFORMATION: 5-E22 HC CDR3

<400> SEQUENCE: 95

Ala Arg Gly Phe Pro Tyr Tyr Ala Met Asp Tyr
1               5                   10

<210> SEQ ID NO 96
<211> LENGTH: 10
<212> TYPE: PRT
<213> ORGANISM: Artificial Sequence
<220> FEATURE:
<223> OTHER INFORMATION: 6-J11 HC CDR1

<400> SEQUENCE: 96

Gly Phe Ile Phe Ser Ser Phe Gly Met His
1               5                   10
```

```
<210> SEQ ID NO 97
<211> LENGTH: 17
<212> TYPE: PRT
<213> ORGANISM: Artificial Sequence
<220> FEATURE:
<223> OTHER INFORMATION: 6-J11 HC CDR2

<400> SEQUENCE: 97

Tyr Ile Ser Ser Gly Arg Ser Thr Met Tyr Tyr Ala Asp Thr Val Lys
1               5                   10                  15

Gly

<210> SEQ ID NO 98
<211> LENGTH: 12
<212> TYPE: PRT
<213> ORGANISM: Artificial Sequence
<220> FEATURE:
<223> OTHER INFORMATION: 6-J11 HC CDR3

<400> SEQUENCE: 98

Ala Arg Gly Gly Phe Tyr Gly Asn Ser Leu Asp Tyr
1               5                   10

<210> SEQ ID NO 99
<211> LENGTH: 10
<212> TYPE: PRT
<213> ORGANISM: Artificial Sequence
<220> FEATURE:
<223> OTHER INFORMATION: 8-G12 HC CDR1

<400> SEQUENCE: 99

Gly Tyr Ala Phe Ser Asp Tyr Trp Met Asn
1               5                   10

<210> SEQ ID NO 100
<211> LENGTH: 17
<212> TYPE: PRT
<213> ORGANISM: Artificial Sequence
<220> FEATURE:
<223> OTHER INFORMATION: 8-G12 HC CDR2

<400> SEQUENCE: 100

Gln Ile Tyr Pro Gly Tyr Gly Asp Thr Lys Tyr Asn Glu Asn Phe Lys
1               5                   10                  15

Gly

<210> SEQ ID NO 101
<211> LENGTH: 12
<212> TYPE: PRT
<213> ORGANISM: Artificial Sequence
<220> FEATURE:
<223> OTHER INFORMATION: 8-G12 HC CDR3

<400> SEQUENCE: 101

Ala Arg Trp Gly Tyr Tyr Gly Asn Ala Met Asp Tyr
1               5                   10

<210> SEQ ID NO 102
<211> LENGTH: 10
<212> TYPE: PRT
<213> ORGANISM: Artificial Sequence
<220> FEATURE:
<223> OTHER INFORMATION: 10-J10 HC CDR1
```

```
<400> SEQUENCE: 102

Gly Tyr Thr Phe Thr Arg Tyr Arg Met Asn
1               5                   10

<210> SEQ ID NO 103
<211> LENGTH: 17
<212> TYPE: PRT
<213> ORGANISM: Artificial Sequence
<220> FEATURE:
<223> OTHER INFORMATION: 10-J10 HC CDR2

<400> SEQUENCE: 103

Asn Ile Asp Pro Ser Asp Ser Glu Thr His Tyr Asn Gln Lys Phe Lys
1               5                   10                  15

Asp

<210> SEQ ID NO 104
<211> LENGTH: 11
<212> TYPE: PRT
<213> ORGANISM: Artificial Sequence
<220> FEATURE:
<223> OTHER INFORMATION: 10-J10 HC CDR3

<400> SEQUENCE: 104

Ala Arg Leu Asn Tyr Gly Asn Cys Phe Asp Tyr
1               5                   10

<210> SEQ ID NO 105
<211> LENGTH: 10
<212> TYPE: PRT
<213> ORGANISM: Artificial Sequence
<220> FEATURE:
<223> OTHER INFORMATION: 10-K2 HC CDR1

<400> SEQUENCE: 105

Gly Tyr Ala Phe Thr Ser Tyr Val Met His
1               5                   10

<210> SEQ ID NO 106
<211> LENGTH: 17
<212> TYPE: PRT
<213> ORGANISM: Artificial Sequence
<220> FEATURE:
<223> OTHER INFORMATION: 10-K2 HC CDR2

<400> SEQUENCE: 106

Tyr Ile Asn Pro Tyr Ser Asp Gly Thr Arg Tyr Asn Glu Lys Phe Lys
1               5                   10                  15

Gly

<210> SEQ ID NO 107
<211> LENGTH: 11
<212> TYPE: PRT
<213> ORGANISM: Artificial Sequence
<220> FEATURE:
<223> OTHER INFORMATION: 10-K2 HC CDR3

<400> SEQUENCE: 107

Thr Arg Ile Tyr Tyr Gly Asn Ala Met Asp Tyr
1               5                   10

<210> SEQ ID NO 108
<211> LENGTH: 10
<212> TYPE: PRT
```

```
<213> ORGANISM: Artificial Sequence
<220> FEATURE:
<223> OTHER INFORMATION: 15-D6 HC CDR1

<400> SEQUENCE: 108

Gly Tyr Thr Phe Thr Ser Tyr Trp Ile Asn
1               5                   10

<210> SEQ ID NO 109
<211> LENGTH: 17
<212> TYPE: PRT
<213> ORGANISM: Artificial Sequence
<220> FEATURE:
<223> OTHER INFORMATION: 15-D6 HC CDR2

<400> SEQUENCE: 109

Asn Ile Tyr Pro Gly Arg Ser Ser Thr Asn Tyr Asn Glu Lys Phe Lys
1               5                   10                  15

Ser

<210> SEQ ID NO 110
<211> LENGTH: 11
<212> TYPE: PRT
<213> ORGANISM: Artificial Sequence
<220> FEATURE:
<223> OTHER INFORMATION: 15-D6 HC CDR3

<400> SEQUENCE: 110

Ser Arg Leu Ser Arg Gly Asn Ala Met Asp Tyr
1               5                   10

<210> SEQ ID NO 111
<211> LENGTH: 17
<212> TYPE: PRT
<213> ORGANISM: Artificial Sequence
<220> FEATURE:
<223> OTHER INFORMATION: 2-C3 LC CDR1

<400> SEQUENCE: 111

Lys Ser Ser Gln Ser Leu Leu Asn Ser Gly Asn Gln Lys Asn Tyr Leu
1               5                   10                  15

Thr

<210> SEQ ID NO 112
<211> LENGTH: 7
<212> TYPE: PRT
<213> ORGANISM: Artificial Sequence
<220> FEATURE:
<223> OTHER INFORMATION: 2-C3 LC CDR2

<400> SEQUENCE: 112

Trp Ala Ser Thr Arg Glu Ser
1               5

<210> SEQ ID NO 113
<211> LENGTH: 9
<212> TYPE: PRT
<213> ORGANISM: Artificial Sequence
<220> FEATURE:
<223> OTHER INFORMATION: 2-C3 LC CDR3

<400> SEQUENCE: 113

Gln Asn Asp Tyr Ser Tyr Pro Leu Thr
1               5
```

```
<210> SEQ ID NO 114
<211> LENGTH: 11
<212> TYPE: PRT
<213> ORGANISM: Artificial Sequence
<220> FEATURE:
<223> OTHER INFORMATION: 2-P8 LC CDR1

<400> SEQUENCE: 114

Lys Ala Ser Gln Asp Ile Asn Arg Tyr Leu Ser
1               5                   10

<210> SEQ ID NO 115
<211> LENGTH: 7
<212> TYPE: PRT
<213> ORGANISM: Artificial Sequence
<220> FEATURE:
<223> OTHER INFORMATION: 2-P8 LC CDR2

<400> SEQUENCE: 115

Arg Ala Asn Arg Leu Val Asp
1               5

<210> SEQ ID NO 116
<211> LENGTH: 9
<212> TYPE: PRT
<213> ORGANISM: Artificial Sequence
<220> FEATURE:
<223> OTHER INFORMATION: 2-P8 LC CDR3

<400> SEQUENCE: 116

Leu Gln Tyr Asp Glu Phe Pro Leu Thr
1               5

<210> SEQ ID NO 117
<211> LENGTH: 17
<212> TYPE: PRT
<213> ORGANISM: Artificial Sequence
<220> FEATURE:
<223> OTHER INFORMATION: 3-E21 LC CDR1

<400> SEQUENCE: 117

Lys Ser Ser Gln Ser Leu Leu Asn Ser Gly Asn Gln Lys Asn Tyr Leu
1               5                   10                  15

Thr

<210> SEQ ID NO 118
<211> LENGTH: 7
<212> TYPE: PRT
<213> ORGANISM: Artificial Sequence
<220> FEATURE:
<223> OTHER INFORMATION: 3-E21 LC CDR2

<400> SEQUENCE: 118

Trp Ala Ser Thr Arg Glu Ser
1               5

<210> SEQ ID NO 119
<211> LENGTH: 9
<212> TYPE: PRT
<213> ORGANISM: Artificial Sequence
<220> FEATURE:
<223> OTHER INFORMATION: 3-E21 LC CDR3

<400> SEQUENCE: 119

Gln Asn Asp Tyr Phe Tyr Pro Leu Thr
1               5
```

```
<210> SEQ ID NO 120
<211> LENGTH: 17
<212> TYPE: PRT
<213> ORGANISM: Artificial Sequence
<220> FEATURE:
<223> OTHER INFORMATION: 3-P21 LC CDR1

<400> SEQUENCE: 120

Lys Ser Ser Gln Ser Leu Leu Asn Ser Gly Asn Gln Lys Asn Tyr Leu
1               5                   10                  15

Thr

<210> SEQ ID NO 121
<211> LENGTH: 7
<212> TYPE: PRT
<213> ORGANISM: Artificial Sequence
<220> FEATURE:
<223> OTHER INFORMATION: 3-P21 LC CDR2

<400> SEQUENCE: 121

Trp Ala Ser Thr Arg Glu Ser
1               5

<210> SEQ ID NO 122
<211> LENGTH: 9
<212> TYPE: PRT
<213> ORGANISM: Artificial Sequence
<220> FEATURE:
<223> OTHER INFORMATION: 3-P21 LC CDR3

<400> SEQUENCE: 122

Gln Asn Asp Tyr Phe Tyr Pro Leu Thr
1               5

<210> SEQ ID NO 123
<211> LENGTH: 11
<212> TYPE: PRT
<213> ORGANISM: Artificial Sequence
<220> FEATURE:
<223> OTHER INFORMATION: 5-E22 LC CDR1

<400> SEQUENCE: 123

His Ala Arg Gln Asn Ile Asn Val Trp Leu Ser
1               5                   10

<210> SEQ ID NO 124
<211> LENGTH: 7
<212> TYPE: PRT
<213> ORGANISM: Artificial Sequence
<220> FEATURE:
<223> OTHER INFORMATION: 5-E22 LC CDR2

<400> SEQUENCE: 124

Lys Ala Ser Asn Leu His Thr
1               5

<210> SEQ ID NO 125
<211> LENGTH: 9
<212> TYPE: PRT
<213> ORGANISM: Artificial Sequence
<220> FEATURE:
<223> OTHER INFORMATION: 5-E22 LC CDR3

<400> SEQUENCE: 125

Gln Gln Gly Gln Asn Tyr Pro Leu Thr
1               5
```

```
<210> SEQ ID NO 126
<211> LENGTH: 17
<212> TYPE: PRT
<213> ORGANISM: Artificial Sequence
<220> FEATURE:
<223> OTHER INFORMATION: 6-J11 LC CDR1

<400> SEQUENCE: 126

Lys Ser Ser Leu Ser Leu Leu Asn Ser Gly Asn Gln Lys Asn Tyr Leu
1               5                   10                  15

Thr

<210> SEQ ID NO 127
<211> LENGTH: 7
<212> TYPE: PRT
<213> ORGANISM: Artificial Sequence
<220> FEATURE:
<223> OTHER INFORMATION: 6-J11 LC CDR2

<400> SEQUENCE: 127

Trp Ala Ser Thr Arg Glu Ser
1               5

<210> SEQ ID NO 128
<211> LENGTH: 9
<212> TYPE: PRT
<213> ORGANISM: Artificial Sequence
<220> FEATURE:
<223> OTHER INFORMATION: 6-J11 LC CDR3

<400> SEQUENCE: 128

Gln Asn Ala Tyr Ser Tyr Pro Leu Thr
1               5

<210> SEQ ID NO 129
<211> LENGTH: 17
<212> TYPE: PRT
<213> ORGANISM: Artificial Sequence
<220> FEATURE:
<223> OTHER INFORMATION: 8-G12 LC CDR1

<400> SEQUENCE: 129

Lys Ser Ser Gln Ser Leu Leu Asn Ser Gly Asn Gln Lys Asn Tyr Leu
1               5                   10                  15

Thr

<210> SEQ ID NO 130
<211> LENGTH: 7
<212> TYPE: PRT
<213> ORGANISM: Artificial Sequence
<220> FEATURE:
<223> OTHER INFORMATION: 8-G12 LC CDR2

<400> SEQUENCE: 130

Trp Ala Ser Thr Arg Glu Ser
1               5

<210> SEQ ID NO 131
<211> LENGTH: 9
<212> TYPE: PRT
<213> ORGANISM: Artificial Sequence
<220> FEATURE:
<223> OTHER INFORMATION: 8-G12 LC CDR3
```

<400> SEQUENCE: 131

Gln Asn Ala Tyr Ile Tyr Pro Leu Thr
1               5

<210> SEQ ID NO 132
<211> LENGTH: 17
<212> TYPE: PRT
<213> ORGANISM: Artificial Sequence
<220> FEATURE:
<223> OTHER INFORMATION: 10-J10 LC CDR1

<400> SEQUENCE: 132

Lys Ser Ser Gln Thr Leu Leu Asn Ser Gly Asn Gln Lys Asn Tyr Leu
1               5                   10                  15
Thr

<210> SEQ ID NO 133
<211> LENGTH: 7
<212> TYPE: PRT
<213> ORGANISM: Artificial Sequence
<220> FEATURE:
<223> OTHER INFORMATION: 10-J10 LC CDR2

<400> SEQUENCE: 133

Trp Ala Ser Thr Arg Glu Ser
1               5

<210> SEQ ID NO 134
<211> LENGTH: 9
<212> TYPE: PRT
<213> ORGANISM: Artificial Sequence
<220> FEATURE:
<223> OTHER INFORMATION: 10-J10 LC CDR3

<400> SEQUENCE: 134

Gln Asn Asp Tyr Phe Tyr Pro Phe Thr
1               5

<210> SEQ ID NO 135
<211> LENGTH: 17
<212> TYPE: PRT
<213> ORGANISM: Artificial Sequence
<220> FEATURE:
<223> OTHER INFORMATION: 10-K2 LC CDR1

<400> SEQUENCE: 135

Lys Ser Ser Gln Ser Leu Leu Asn Ser Gly Asn Gln Lys Asn Tyr Leu
1               5                   10                  15
Thr

<210> SEQ ID NO 136
<211> LENGTH: 7
<212> TYPE: PRT
<213> ORGANISM: Artificial Sequence
<220> FEATURE:
<223> OTHER INFORMATION: 10-K2 LC CDR2

<400> SEQUENCE: 136

Trp Ala Ser Thr Arg Glu Ser
1               5

<210> SEQ ID NO 137
<211> LENGTH: 9
<212> TYPE: PRT

```
<213> ORGANISM: Artificial Sequence
<220> FEATURE:
<223> OTHER INFORMATION: 10-K2 LC CDR3

<400> SEQUENCE: 137

Gln Asn Asp Tyr Ser Tyr Pro Phe Thr
1               5

<210> SEQ ID NO 138
<211> LENGTH: 17
<212> TYPE: PRT
<213> ORGANISM: Artificial Sequence
<220> FEATURE:
<223> OTHER INFORMATION: 15-D6 LC CDR1

<400> SEQUENCE: 138

Arg Ser Ser Gln Ser Leu Leu Asn Ser Gly Asn Gln Lys Ser Tyr Leu
1               5                   10                  15

Thr

<210> SEQ ID NO 139
<211> LENGTH: 7
<212> TYPE: PRT
<213> ORGANISM: Artificial Sequence
<220> FEATURE:
<223> OTHER INFORMATION: 15-D6 LC CDR2

<400> SEQUENCE: 139

Trp Ala Ser Thr Arg Glu Ser
1               5

<210> SEQ ID NO 140
<211> LENGTH: 9
<212> TYPE: PRT
<213> ORGANISM: Artificial Sequence
<220> FEATURE:
<223> OTHER INFORMATION: 15-D6 LC CDR3

<400> SEQUENCE: 140

Gln Asn Asp Tyr Tyr Tyr Pro Phe Thr
1               5

<210> SEQ ID NO 141
<211> LENGTH: 261
<212> TYPE: PRT
<213> ORGANISM: Homo sapiens

<400> SEQUENCE: 141

Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
                20                  25                  30

Gln Asp Leu Tyr Asn Asn Pro Val Thr Ala Val Phe Asn Tyr Gln Gly
            35                  40                  45

Leu Trp Arg Ser Cys Val Arg Glu Ser Ser Gly Phe Thr Glu Cys Arg
        50                  55                  60

Gly Tyr Phe Thr Leu Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
                100                 105                 110
```

```
Ala Lys Ala Asn Met Thr Leu Thr Ser Gly Ile Met Phe Ile Val Ser
            115                 120                 125

Gly Leu Cys Ala Ile Ala Gly Val Ser Val Phe Ala Asn Met Leu Val
        130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
        195                 200                 205

Val Ser Tyr His Ala Ser Gly His Ser Val Ala Tyr Lys Pro Gly Gly
    210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
            260

<210> SEQ ID NO 142
<211> LENGTH: 118
<212> TYPE: PRT
<213> ORGANISM: Artificial Sequence
<220> FEATURE:
<223> OTHER INFORMATION: 2-C3-H1 Heavy Chain Variable Region

<400> SEQUENCE: 142

Gln Val Thr Leu Arg Glu Ser Gly Pro Ala Leu Val Lys Pro Thr Gln
1               5                   10                  15

Thr Leu Thr Leu Thr Cys Thr Ala Ser Gly Phe Thr Phe Ser Ser Tyr
            20                  25                  30

Gly Met Ser Trp Val Arg Gln Pro Pro Gly Lys Ala Leu Glu Trp Val
        35                  40                  45

Ala Thr Ile Ser Gly Gly Gly Ser Tyr Thr Tyr Tyr Asn Pro Ser Leu
    50                  55                  60

Lys Asp Arg Phe Thr Ile Ser Arg Asp Ile Ser Ala Asn Gln Leu Val
65                  70                  75                  80

Leu Lys Val Thr Asn Met Asp Pro Ala Asp Thr Ala Thr Tyr Phe Cys
                85                  90                  95

Ala Arg Gln Ser Arg Gly Asn Ala Met Asp Tyr Trp Gly Gln Gly Thr
            100                 105                 110

Thr Val Thr Val Ser Ser
        115

<210> SEQ ID NO 143
<211> LENGTH: 118
<212> TYPE: PRT
<213> ORGANISM: Artificial Sequence
<220> FEATURE:
<223> OTHER INFORMATION: 2-C3-H2 Heavy Chain Variable Region

<400> SEQUENCE: 143

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Thr Phe Ser Ser Tyr
            20                  25                  30
```

Gly Met Ser Trp Ile Arg Gln Pro Gly Lys Ala Leu Glu Trp Leu
            35                  40                  45

Ala Thr Ile Ser Gly Gly Gly Ser Tyr Thr Tyr Tyr Leu Asp Ser Leu
         50                  55                  60

Lys Asp Arg Phe Thr Ile Ser Arg Asp Ile Ser Lys Asn Gln Val Val
 65                  70                  75                  80

Leu Thr Val Thr Asn Met Asp Pro Ala Asp Thr Ala Thr Tyr Phe Cys
                 85                  90                  95

Ala Arg Gln Ser Arg Gly Asn Ala Met Asp Tyr Trp Gly Gln Gly Thr
                100                 105                 110

Thr Val Thr Val Ser Ser
            115

<210> SEQ ID NO 144
<211> LENGTH: 113
<212> TYPE: PRT
<213> ORGANISM: Artificial Sequence
<220> FEATURE:
<223> OTHER INFORMATION: 2-C3-L1 Light Chain Variable Region

<400> SEQUENCE: 144

Asp Ile Gln Met Thr Gln Ser Pro Ser Thr Leu Ser Ala Ser Val Gly
  1               5                  10                  15

Asp Arg Val Thr Ile Thr Cys Lys Ser Ser Gln Ser Leu Leu Asn Ser
             20                  25                  30

Gly Asn Gln Lys Asn Tyr Leu Thr Trp Tyr Gln Gln Lys Pro Gly Lys
         35                  40                  45

Ala Pro Lys Leu Leu Ile Tyr Trp Ala Ser Thr Arg Glu Ser Gly Val
     50                  55                  60

Pro Ser Arg Phe Ser Gly Ser Gly Ser Gly Thr Ala Phe Thr Leu Thr
 65                  70                  75                  80

Ile Ser Ser Leu Gln Pro Asp Asp Phe Ala Thr Tyr Tyr Cys Gln Asn
                 85                  90                  95

Asp Tyr Ser Tyr Pro Leu Thr Phe Gly Gly Gly Thr Lys Val Glu Ile
                100                 105                 110

Lys

<210> SEQ ID NO 145
<211> LENGTH: 113
<212> TYPE: PRT
<213> ORGANISM: Artificial Sequence
<220> FEATURE:
<223> OTHER INFORMATION: 2-C3-L2 Light Chain Variable Region

<400> SEQUENCE: 145

Asp Ile Gln Met Thr Gln Ser Pro Ser Thr Leu Ser Ala Ser Val Gly
  1               5                  10                  15

Asp Arg Val Thr Ile Thr Cys Lys Ser Ser Gln Ser Leu Leu Asn Ser
             20                  25                  30

Gly Asn Gln Lys Asn Tyr Leu Thr Trp Tyr Gln Gln Lys Pro Gly Lys
         35                  40                  45

Ala Pro Lys Leu Leu Ile Tyr Trp Ala Ser Thr Arg Glu Ser Gly Val
     50                  55                  60

Pro Ser Arg Phe Ser Gly Ser Gly Ser Gly Thr Glu Phe Thr Leu Thr
 65                  70                  75                  80

Ile Ser Ser Leu Gln Pro Asp Asp Phe Ala Thr Tyr Tyr Cys Gln Asn
                 85                  90                  95

Asp Tyr Ser Tyr Pro Leu Thr Phe Gly Gly Thr Lys Val Glu Ile
            100                 105                 110

Lys

<210> SEQ ID NO 146
<211> LENGTH: 118
<212> TYPE: PRT
<213> ORGANISM: Artificial Sequence
<220> FEATURE:
<223> OTHER INFORMATION: 5-E22-H1 Heavy Chain Variable Region

<400> SEQUENCE: 146

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Ile Thr Asp Asn
            20                  25                  30

Tyr Met His Trp Val Arg Gln Ala Pro Gly Gln Gly Leu Glu Trp Ile
        35                  40                  45

Gly Glu Ile Tyr Pro Gly Ser Gly Asn Thr Tyr Phe Asn Glu Lys Phe
    50                  55                  60

Lys Asn Arg Ala Thr Leu Thr Ala Asp Lys Ser Thr Thr Thr Ala Tyr
65                  70                  75                  80

Met Glu Leu Lys Ser Leu Gln Phe Asp Asp Thr Ala Val Tyr Phe Cys
                85                  90                  95

Ala Arg Gly Phe Pro Tyr Tyr Ala Met Asp Tyr Trp Gly Gln Gly Thr
            100                 105                 110

Thr Val Thr Val Ser Ser
        115

<210> SEQ ID NO 147
<211> LENGTH: 118
<212> TYPE: PRT
<213> ORGANISM: Artificial Sequence
<220> FEATURE:
<223> OTHER INFORMATION: 5-E22-H3 Heavy Chain Variable Region

<400> SEQUENCE: 147

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Ile Thr Asp Asn
            20                  25                  30

Tyr Met His Trp Val Arg Gln Ala Pro Gly Gln Gly Leu Glu Trp Ile
        35                  40                  45

Gly Glu Ile Tyr Pro Gly Ser Gly Asn Thr Tyr Tyr Ala Glu Lys Phe
    50                  55                  60

Lys Asn Arg Ala Thr Leu Thr Ala Asp Lys Ser Ile Ser Thr Ala Tyr
65                  70                  75                  80

Met Glu Leu Ser Arg Leu Arg Ser Asp Asp Thr Ala Val Tyr Phe Cys
                85                  90                  95

Ala Arg Gly Phe Pro Tyr Tyr Ala Met Asp Tyr Trp Gly Gln Gly Thr
            100                 105                 110

Leu Val Thr Val Ser Ser
        115

<210> SEQ ID NO 148
<211> LENGTH: 107
<212> TYPE: PRT
<213> ORGANISM: Artificial Sequence
<220> FEATURE:
<223> OTHER INFORMATION: 5-E22-L1 Light Chain Variable Region

<400> SEQUENCE: 148

Glu Ile Val Met Thr Gln Ser Pro Ala Thr Leu Ser Leu Ser Pro Gly
1               5                   10                  15

Glu Arg Ala Thr Leu Ser Cys His Ala Arg Gln Asn Ile Asn Val Trp
            20                  25                  30

Leu Ser Trp Tyr Gln Gln Lys Pro Gly Gln Ala Pro Arg Leu Leu Ile
        35                  40                  45

Tyr Lys Ala Ser Asn Leu His Thr Gly Val Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Gly Gln Asn Tyr Pro Leu
                85                  90                  95

Thr Phe Gly Gly Gly Thr Lys Val Glu Ile Lys
            100                 105

<210> SEQ ID NO 149
<211> LENGTH: 107
<212> TYPE: PRT
<213> ORGANISM: Artificial Sequence
<220> FEATURE:
<223> OTHER INFORMATION: 5-E22-L2 Light Chain Variable Region

<400> SEQUENCE: 149

Glu Ile Val Leu Thr Gln Ser Pro Ala Thr Leu Ser Leu Ser Pro Gly
1               5                   10                  15

Glu Arg Ala Thr Leu Ser Cys His Ala Arg Gln Asn Ile Asn Val Trp
            20                  25                  30

Leu Ser Trp Tyr Gln Gln Lys Pro Gly Gln Ala Pro Arg Leu Leu Ile
        35                  40                  45

Tyr Lys Ala Ser Asn Leu His Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Gly Gln Asn Tyr Pro Leu
                85                  90                  95

Thr Phe Gly Gly Gly Thr Lys Val Glu Ile Lys
            100                 105

<210> SEQ ID NO 150
<211> LENGTH: 107
<212> TYPE: PRT
<213> ORGANISM: Artificial Sequence
<220> FEATURE:
<223> OTHER INFORMATION: 5-E22-L3 Light Chain Variable Region

<400> SEQUENCE: 150

Asp Ile Val Met Thr Gln Ser Pro Leu Ser Leu Pro Val Thr Pro Gly
1               5                   10                  15

Glu Pro Ala Ser Ile Ser Cys His Ala Arg Gln Asn Ile Asn Val Trp
            20                  25                  30

Leu Ser Trp Tyr Leu Gln Lys Pro Gly Gln Ser Pro Gln Leu Leu Ile
        35                  40                  45

Tyr Lys Ala Ser Asn Leu His Thr Gly Val Pro Asp Arg Phe Ser Gly
    50                  55                  60

```
Ser Gly Ser Gly Thr Asp Phe Thr Leu Lys Ile Ser Arg Val Glu Ala
 65                  70                  75                  80

Glu Asp Val Gly Val Tyr Tyr Cys Gln Gln Gly Gln Asn Tyr Pro Leu
                 85                  90                  95

Thr Phe Gly Gln Gly Thr Lys Val Glu Ile Lys
            100                 105

<210> SEQ ID NO 151
<211> LENGTH: 119
<212> TYPE: PRT
<213> ORGANISM: Artificial Sequence
<220> FEATURE:
<223> OTHER INFORMATION: 6-J11-H1 Heavy Chain Variable Region

<400> SEQUENCE: 151

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Ser Phe
            20                  25                  30

Gly Met His Trp Val Arg Gln Ala Pro Gly Lys Gly Leu Glu Trp Val
        35                  40                  45

Ala Tyr Ile Ser Ser Gly Arg Ser Thr Met Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Thr Ala Glu Asp Thr Ala Val Tyr Tyr Cys
                 85                  90                  95

Ala Arg Gly Gly Phe Tyr Gly Asn Ser Leu Asp Tyr Trp Gly Gln Gly
            100                 105                 110

Thr Leu Val Thr Val Ser Ser
        115

<210> SEQ ID NO 152
<211> LENGTH: 119
<212> TYPE: PRT
<213> ORGANISM: Artificial Sequence
<220> FEATURE:
<223> OTHER INFORMATION: 6-J11-H2 Heavy Chain Variable Region

<400> SEQUENCE: 152

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Ser Phe
            20                  25                  30

Gly Met His Trp Val Arg Gln Ala Pro Gly Lys Gly Leu Glu Trp Val
        35                  40                  45

Ala Tyr Ile Ser Ser Gly Arg Ser Thr Met Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ser Glu Asp Thr Ala Val Tyr Tyr Cys
                 85                  90                  95

Ala Arg Gly Gly Phe Tyr Gly Asn Ser Leu Asp Tyr Trp Gly Gln Gly
            100                 105                 110

Thr Leu Val Thr Val Ser Ser
        115

<210> SEQ ID NO 153
```

```
<211> LENGTH: 113
<212> TYPE: PRT
<213> ORGANISM: Artificial Sequence
<220> FEATURE:
<223> OTHER INFORMATION: 6-J11-L1 Light Chain Variable Region

<400> SEQUENCE: 153

Asp Ile Gln Met Thr Gln Ser Pro Ser Ser Leu Ser Ala Ser Val Gly
1               5                   10                  15

Asp Arg Val Thr Ile Thr Cys Lys Ser Ser Leu Ser Leu Leu Asn Ser
            20                  25                  30

Gly Asn Gln Lys Asn Tyr Leu Thr Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Ser Cys Gln Asn
                85                  90                  95

Ala Tyr Ser Tyr Pro Leu Thr Phe Gly Gln Gly Thr Lys Val Glu Ile
            100                 105                 110

Lys

<210> SEQ ID NO 154
<211> LENGTH: 118
<212> TYPE: PRT
<213> ORGANISM: Artificial Sequence
<220> FEATURE:
<223> OTHER INFORMATION: 3-E21-H1 Heavy Chain Variable Region

<400> SEQUENCE: 154

Gln Val Gln Leu Gln Glu Ser Gly Pro Gly Leu Val Arg Pro Ser Gln
1               5                   10                  15

Thr Leu Ser Leu Thr Cys Thr Ala Ser Gly Phe Thr Phe Ser Lys Tyr
            20                  25                  30

Ala Met Asn Trp Val Arg Gln Pro Pro Gly Arg Gly Leu Glu Trp Val
        35                  40                  45

Ala Phe Ile Ser Asn Gly Gly Ser Tyr Thr Glu Tyr Asn Pro Ser Val
    50                  55                  60

Lys Gly Arg Phe Thr Ile Leu Arg Asp Asn Ser Lys Asn Gln Leu Ser
65                  70                  75                  80

Leu Arg Leu Ser Ser Val Thr Ala Ala Asp Thr Ala Val Tyr Tyr Cys
                85                  90                  95

Ala Arg His Asp Lys Gly Asn Ala Leu Asp Tyr Trp Gly Gln Gly Ser
            100                 105                 110

Leu Val Thr Val Ser Ser
        115

<210> SEQ ID NO 155
<211> LENGTH: 118
<212> TYPE: PRT
<213> ORGANISM: Artificial Sequence
<220> FEATURE:
<223> OTHER INFORMATION: 3-E21-H2 Heavy Chain Variable Region

<400> SEQUENCE: 155

Gln Val Gln Leu Gln Glu Ser Gly Pro Gly Leu Val Arg Pro Ser Gln
1               5                   10                  15
```

-continued

Thr Leu Ser Leu Thr Cys Thr Ala Ser Gly Phe Thr Phe Ser Lys Tyr
            20                  25                  30

Ala Met Ser Trp Val Arg Gln Pro Gly Arg Gly Leu Glu Trp Val
            35                  40                  45

Ala Phe Ile Ser Asn Gly Gly Ser Tyr Thr Glu Tyr Asn Pro Ser Val
50                      55                  60

Lys Gly Arg Phe Thr Ile Leu Arg Asp Asn Ser Lys Asn Gln Leu Ser
65                      70                  75                  80

Leu Lys Leu Ser Ser Val Thr Ala Ala Asp Thr Ala Val Tyr Tyr Cys
                85                  90                  95

Ala Arg His Asp Lys Gly Asn Ala Leu Asp Tyr Trp Gly Gln Gly Ser
            100                 105                 110

Leu Val Thr Val Ser Ser
            115

<210> SEQ ID NO 156
<211> LENGTH: 118
<212> TYPE: PRT
<213> ORGANISM: Artificial Sequence
<220> FEATURE:
<223> OTHER INFORMATION: 3-E21-H3 Heavy Chain Variable Region

<400> SEQUENCE: 156

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Ala Met Ser Trp Val Arg Gln Ala Pro Gly Lys Gly Leu Glu Trp Val
            35                  40                  45

Ala Ala Ile Ser Asn Gly Gly Ser Tyr Thr Tyr Tyr Ala Asp Ser Val
50                      55                  60

Lys Gly Arg Phe Thr Ile Ser Arg Asp Asn Ser Lys Asn Thr Leu Tyr
65                      70                  75                  80

Leu Gln Met Asn Ser Leu Arg Ala Glu Asp Thr Ala Val Tyr Tyr Cys
                85                  90                  95

Ala Arg His Asp Lys Gly Asn Ala Leu Asp Tyr Trp Gly Gln Gly Thr
            100                 105                 110

Leu Val Thr Val Ser Ser
            115

<210> SEQ ID NO 157
<211> LENGTH: 113
<212> TYPE: PRT
<213> ORGANISM: Artificial Sequence
<220> FEATURE:
<223> OTHER INFORMATION: 3-E21-L1 Light Chain Variable Region

<400> SEQUENCE: 157

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Asn Tyr Leu Thr Trp Tyr Gln Gln Lys Pro Gly Lys
            35                  40                  45

Ala Pro Lys Leu Leu Ile Tyr Trp Ala Ser Asn Leu Gln Thr Gly Val
50                      55                  60

Pro Ser Arg Phe Ser Gly Ser Gly Ser Gly Thr Asp Phe Thr Phe Thr
65                  70                  75                  80

Ile Ser Ser Leu Gln Pro Glu Asp Ile Ala Thr Tyr Tyr Cys Gln Asn
                85                  90                  95

Asp Tyr Phe Tyr Pro Leu Thr Phe Gly Gln Gly Thr Lys Val Glu Ile
            100                 105                 110

Lys

<210> SEQ ID NO 158
<211> LENGTH: 113
<212> TYPE: PRT
<213> ORGANISM: Artificial Sequence
<220> FEATURE:
<223> OTHER INFORMATION: 3-E21-L2 Light Chain Variable Region

<400> SEQUENCE: 158

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
                20                  25                  30

Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Phe Tyr Pro Leu Thr Phe Gly Gln Gly Thr Arg Leu Glu Ile
            100                 105                 110

Lys

<210> SEQ ID NO 159
<211> LENGTH: 119
<212> TYPE: PRT
<213> ORGANISM: Artificial Sequence
<220> FEATURE:
<223> OTHER INFORMATION: 3-P21-H1 Heavy Chain Variable Region

<400> SEQUENCE: 159

Glu Ile Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
                20                  25                  30

Asn Ile His Trp Val Arg Gln Ala Pro Gly Lys Gly Leu Glu Trp Ile
            35                  40                  45

Gly Tyr Ile Asn Pro Tyr Phe Gly Ser Thr Asp Tyr Ala Asp Ser Val
50                  55                  60

Lys Gly Arg Ala Thr Leu Ser Val Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ala Tyr Tyr Gly Asn Ala Met Asp Tyr Trp Gly Gln Gly
            100                 105                 110

Thr Leu Val Thr Val Ser Ser
            115

```
<210> SEQ ID NO 160
<211> LENGTH: 119
<212> TYPE: PRT
<213> ORGANISM: Artificial Sequence
<220> FEATURE:
<223> OTHER INFORMATION: 3-P21-H2 Heavy Chain Variable Region

<400> SEQUENCE: 160

Glu Ile Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Asn Met Lys Trp Val Arg Gln Ala Pro Gly Lys Gly Leu Glu Trp Ile
        35                  40                  45

Gly Asn Ile Asn Pro Tyr Phe Gly Ser Thr Asn Tyr Ala Asp Ser Val
    50                  55                  60

Lys Gly Arg Ala Thr Leu Ser Val Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ala Tyr Tyr Gly Asn Ala Met Asp Tyr Trp Gly Gln Gly
            100                 105                 110

Thr Leu Val Thr Val Ser Ser
        115

<210> SEQ ID NO 161
<211> LENGTH: 119
<212> TYPE: PRT
<213> ORGANISM: Artificial Sequence
<220> FEATURE:
<223> OTHER INFORMATION: 3-P21-H3 Heavy Chain Variable Region

<400> SEQUENCE: 161

Glu Ile Gln Leu Val Gln Ser Gly Ala Glu Val Lys Lys Pro Gly Glu
1               5                   10                  15

Ser Leu Lys Ile Ser Cys Lys Ala Ser Gly Tyr Ser Phe Thr Gly Tyr
            20                  25                  30

Asn Ile Gly Trp Val Arg Gln Met Pro Gly Lys Gly Leu Glu Trp Ile
        35                  40                  45

Gly Ile Ile Asn Pro Tyr Phe Gly Ser Thr Arg Tyr Ser Pro Ser Phe
    50                  55                  60

Gln Gly Gln Ala Thr Leu Ser Val Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Ala Tyr Tyr Gly Asn Ala Met Asp Tyr Trp Gly Gln Gly
            100                 105                 110

Thr Leu Val Thr Val Ser Ser
        115

<210> SEQ ID NO 162
<211> LENGTH: 119
<212> TYPE: PRT
<213> ORGANISM: Artificial Sequence
<220> FEATURE:
<223> OTHER INFORMATION: 3-P21-H4 Heavy Chain Variable Region
```

<400> SEQUENCE: 162

Glu Ile Gln Leu Val Gln Ser Gly Ala Glu Val Lys Lys Pro Gly Glu
1               5                   10                  15

Ser Leu Lys Ile Ser Cys Lys Ala Ser Gly Tyr Ser Phe Thr Gly Tyr
            20                  25                  30

Asn Met Lys Trp Val Arg Gln Met Pro Gly Lys Gly Leu Glu Trp Ile
        35                  40                  45

Gly Ile Ile Asn Pro Tyr Phe Gly Ser Thr Asn Tyr Ser Pro Ser Phe
    50                  55                  60

Gln Gly Gln Ala Thr Leu Ser Val Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Ala Tyr Tyr Gly Asn Ala Met Asp Tyr Trp Gly Gln Gly
            100                 105                 110

Thr Leu Val Thr Val Ser Ser
        115

<210> SEQ ID NO 163
<211> LENGTH: 113
<212> TYPE: PRT
<213> ORGANISM: Artificial Sequence
<220> FEATURE:
<223> OTHER INFORMATION: 3-P21-L1 Light Chain Variable Region

<400> SEQUENCE: 163

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Leu Asn Ser
            20                  25                  30

Gly Asn Gln Lys Asn Tyr Val Thr Trp Tyr Gln Gln Lys Pro Gly Lys
        35                  40                  45

Ala Pro Lys Leu Leu Ile Tyr Trp Ala Ser Phe Leu Tyr Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Asn
                85                  90                  95

Asp Tyr Phe Tyr Pro Leu Thr Phe Gly Gln Gly Thr Lys Val Glu Ile
            100                 105                 110

Lys

<210> SEQ ID NO 164
<211> LENGTH: 113
<212> TYPE: PRT
<213> ORGANISM: Artificial Sequence
<220> FEATURE:
<223> OTHER INFORMATION: 3-P21-L2 Light Chain Variable Region

<400> SEQUENCE: 164

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Leu Asn Ser
            20                  25                  30

Gly Asn Gln Lys Asn Tyr Val Thr Trp Tyr Gln Gln Lys Pro Gly Lys
        35                  40                  45

-continued

```
Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Asn
                85                  90                  95

Asp Tyr Phe Tyr Pro Leu Thr Phe Gly Gln Gly Thr Lys Val Glu Ile
            100                 105                 110

Lys

<210> SEQ ID NO 165
<211> LENGTH: 113
<212> TYPE: PRT
<213> ORGANISM: Artificial Sequence
<220> FEATURE:
<223> OTHER INFORMATION: 3-P21-L3 Light Chain Variable Region

<400> SEQUENCE: 165

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Phe Tyr Pro Leu Thr Phe Gly Gln Gly Thr Lys Val Glu Ile
            100                 105                 110

Lys
```

ANTI-CLAUDIN 18.2 ANTIBODIES AND USES THEREOF

CROSS REFERENCE TO RELATED APPLICATIONS

This application is a Section 371 of International Application No. PCT/US2019/020872, filed Mar. 6, 2019, which published in the English language on Sep. 12, 2019 under International Publication No. WO 2019/173420 A1, which claims priority to U.S. Provisional Application No. 62/640,288, filed Mar. 8, 2018, and U.S. Provisional Application No. 62/714,254, filed Aug. 3, 2018. Each disclosure is incorporated herein by reference in its entirety.

FIELD OF THE INVENTION

This invention relates to monoclonal anti-claudin 18.2 (CLDN18.2) antibodies, nucleic acids and expression vectors encoding the antibodies, recombinant cells containing the vectors, and compositions comprising the antibodies. Methods of making the antibodies, and methods of using the antibodies to treat diseases including cancer and inflammatory diseases and/or associated complications are also provided.

REFERENCE TO SEQUENCE LISTING SUBMITTED ELECTRONICALLY

This application contains a sequence listing, which is submitted electronically via EFS-Web as an ASCII formatted sequence listing with a file name "065799_9US2_Sequence_Listing" and a creation date of Aug. 7, 2020 and having a size of 74 kb. The sequence listing submitted via EFS-Web is part of the specification and is herein incorporated by reference in its entirety.

BACKGROUND OF THE INVENTION

Claudin 18.2 (CLDN18.2), also known as claudin-18a2.1, belongs to the claudin (CLDN) family transmembrane proteins of at least 27 isoforms in humans. Claudins are the major structural components of tight junction between epithelial cells and function as ion pores to regulate the paracellular permeability of cations and anions (Sahin et al., Physiol Rev. 2013; 93:525-569). The expression of CLDN18 is normally limited to lung and stomach tissues. CLDN18 has two splicing variants. CLDN18.1 is the lung-specific variant whereas CLDN18.2 is the stomach-specific variant. The splicing variants differ at their N-terminal 69 amino acid residues due to alternative splicing of the first exon (Niimi et al., Mol Cell Biol. 2001; 21:7380-7390). Studies with CLDN18.2 knockout mice suggest that CLDN18.2 plays a critical role in preventing gastric acid leakage into the stomach lumen (Hayash et al., Gastroenterology 2012; 142:292-304).

Dysregulated expression of claudins are detected in many cancers and may contribute to tumorigenesis and cancer invasiveness (Singh et al., J Oncology 2010; 2010: 541957). The expression of CLDN18.2 is elevated in pancreatic ductal adenocarcinomas (PDAC) (Tanaka et al., J Histochem Cytochem. 2011; 59:942-952), esophageal tumors, non-small cell lung cancers (NSCLC), ovarian cancers (Sahin et al., Hu Cancer Biol. 2008; 14:7624-7634), bile duct adenocarcinomas (Keira et al., Virchows Arch. 2015; 466:265-277), and cholangiocarcinomas (Shinozaki et al., Virchows Arch. 2011; 459:73-80). CLDN18.2 is an ideal target for precision-guided, anti-cancer biologics to CLDN18.2-positive tumors, as CLDN18.2 is not expressed in any normal tissue other than the differentiated gastric epithelial cells, which are unreachable by large molecule compounds administrated intravenously.

BRIEF SUMMARY OF THE INVENTION

In one general aspect, the invention relates to isolated monoclonal antibodies or antigen-binding fragments thereof that specifically bind claudin 18.2 (CLDN18.2).

Provided are isolated monoclonal antibodies or antigen-binding fragments thereof comprising a heavy chain complementarity determining region 1 (HCDR1), HCDR2, HCDR3, a light chain complementarity determining region 1 (LCDR1), LCDR2, and LCDR3, having the polypeptide sequences of:

(1) SEQ ID NOs: 33, 34, 35, 63, 64 and 65, respectively;
(2) SEQ ID NOs: 21, 22, 23, 51, 52 and 53, respectively;
(3) SEQ ID NOs: 24, 25, 26, 54, 55 and 56, respectively;
(4) SEQ ID NOs: 27, 28, 29, 57, 58 and 59, respectively;
(5) SEQ ID NOs: 30, 31, 32, 60, 61 and 62, respectively;
(6) SEQ ID NOs: 36, 37, 38, 66, 67 and 68, respectively;
(7) SEQ ID NOs: 39, 40, 41, 69, 70 and 71, respectively;
(8) SEQ ID NOs: 42, 43, 44, 72, 73 and 74, respectively;
(9) SEQ ID NOs: 45, 46, 47, 75, 76 and 77, respectively; or
(10) SEQ ID NOs: 48, 49, 50, 78, 79 and 80, respectively;

wherein the antibody or antigen-binding fragment thereof specifically binds CLDN18.2, preferably human CLDN18.2.

Provided are isolated monoclonal antibodies or antigen-binding fragments thereof comprising a heavy chain complementarity determining region 1 (HCDR1), HCDR2, HCDR3, a light chain complementarity determining region 1 (LCDR1), LCDR2, and LCDR3, having the polypeptide sequences of:

(1) SEQ ID NOs: 93, 94, 95, 123, 124 and 125, respectively;
(2) SEQ ID NOs: 81, 82, 83, 111, 112 and 113, respectively;
(3) SEQ ID NOs: 84, 85, 86, 114, 115 and 116, respectively;
(4) SEQ ID NOs: 87, 88, 89, 117, 118 and 119, respectively;
(5) SEQ ID NOs: 90, 91, 92, 120, 121 and 122, respectively;
(6) SEQ ID NOs: 96, 97, 98, 126, 127 and 128, respectively;
(7) SEQ ID NOs: 99, 100, 101, 129, 130 and 131, respectively;
(8) SEQ ID NOs: 102, 103, 104, 132, 133 and 134, respectively;
(9) SEQ ID NOs: 105, 106, 107, 135, 136 and 137, respectively; or
(10) SEQ ID NOs: 108, 109, 110, 138, 139 and 140, respectively;

wherein the antibody or antigen-binding fragment thereof specifically binds CLDN18.2, preferably human CLDN18.2.

In certain embodiments, the isolated monoclonal antibody or antigen-binding fragment thereof comprises a heavy chain variable region having a polypeptide sequence at least 95%, at least 96%, at least 97%, at least 98%, or at least 99% identical to SEQ ID NO: 9, 1, 3, 5, 7, 11, 13, 15, 17 or 19, or a light chain variable region having a polypeptide sequence at least 95%, at least 96%, at least 97%, at least 98%, or at least 99% identical to SEQ ID NO: 10, 2, 4, 6, 8, 12, 14, 16, 18 or 20.

In certain embodiments, the isolated monoclonal antibody or antigen-binding fragment thereof comprises:
  (a) a heavy chain variable region having the polypeptide sequence of SEQ ID NO:9, and a light chain variable region having the polypeptide sequence of SEQ ID NO:10;
  (b) a heavy chain variable region having the polypeptide sequence of SEQ ID NO:1, and a light chain variable region having the polypeptide sequence of SEQ ID NO:2;
  (c) a heavy chain variable region having the polypeptide sequence of SEQ ID NO:3, and a light chain variable region having the polypeptide sequence of SEQ ID NO:4;
  (d) a heavy chain variable region having the polypeptide sequence of SEQ ID NO:5, and a light chain variable region having the polypeptide sequence of SEQ ID NO:6;
  (e) a heavy chain variable region having the polypeptide sequence of SEQ ID NO:7, and a light chain variable region having the polypeptide sequence of SEQ ID NO:8;
  (f) a heavy chain variable region having the polypeptide sequence of SEQ ID NO:11, and a light chain variable region having the polypeptide sequence of SEQ ID NO:12;
  (g) a heavy chain variable region having the polypeptide sequence of SEQ ID NO:13, and a light chain variable region having the polypeptide sequence of SEQ ID NO:14;
  (h) a heavy chain variable region having the polypeptide sequence of SEQ ID NO:15, and a light chain variable region having the polypeptide sequence of SEQ ID NO:16;
  (i) a heavy chain variable region having the polypeptide sequence of SEQ ID NO:17, and a light chain variable region having the polypeptide sequence of SEQ ID NO:18; or
  (j) a heavy chain variable region having the polypeptide sequence of SEQ ID NO:19, and a light chain variable region having the polypeptide sequence of SEQ ID NO:20.

In certain embodiments, the isolated monoclonal antibody or antigen-binding fragment thereof binds to CLDN18.2 and is capable of inducing effector-mediated tumor cell lysis through antibody-dependent cellular cytotoxicity (ADCC), antibody-dependent phagocytosis (ADPC), and/or complement-dependent cytotoxicity (CDC), and/or mediating the recruitment of conjugated drugs, and/or forming a bispecific antibody with another monoclonal antibody or antigen-binding fragment thereof with cancer-killing effect.

In certain embodiments, the isolated monoclonal antibody or antigen-binding fragment thereof is chimeric.

In certain embodiments, the isolated monoclonal antibody or antigen-binding fragment thereof is human or humanized.

In certain embodiments, the humanized monoclonal antibody or antigen-binding fragment thereof comprises:
  a. a heavy chain variable region having the polypeptide sequence of SEQ ID NO:142, and a light chain variable region having the polypeptide sequence of SEQ ID NO:144;
  b. a heavy chain variable region having the polypeptide sequence of SEQ ID NO:142, and a light chain variable region having the polypeptide sequence of SEQ ID NO:145;
  c. a heavy chain variable region having the polypeptide sequence of SEQ ID NO:143, and a light chain variable region having the polypeptide sequence of SEQ ID NO:144;
  d. a heavy chain variable region having the polypeptide sequence of SEQ ID NO:143, and a light chain variable region having the polypeptide sequence of SEQ ID NO:145;
  e. a heavy chain variable region having the polypeptide sequence of SEQ ID NO:146, and a light chain variable region having the polypeptide sequence of SEQ ID NO:148;
  f. a heavy chain variable region having the polypeptide sequence of SEQ ID NO:146, and a light chain variable region having the polypeptide sequence of SEQ ID NO:149;
  g. a heavy chain variable region having the polypeptide sequence of SEQ ID NO:146, and a light chain variable region having the polypeptide sequence of SEQ ID NO:150;
  h. a heavy chain variable region having the polypeptide sequence of SEQ ID NO:147, and a light chain variable region having the polypeptide sequence of SEQ ID NO:148;
  i. a heavy chain variable region having the polypeptide sequence of SEQ ID NO:147, and a light chain variable region having the polypeptide sequence of SEQ ID NO:149;
  j. a heavy chain variable region having the polypeptide sequence of SEQ ID NO:147, and a light chain variable region having the polypeptide sequence of SEQ ID NO:150;
  k. a heavy chain variable region having the polypeptide sequence of SEQ ID NO:151, and a light chain variable region having the polypeptide sequence of SEQ ID NO:153;
  l. a heavy chain variable region having the polypeptide sequence of SEQ ID NO:152, and a light chain variable region having the polypeptide sequence of SEQ ID NO:153;
  m. a heavy chain variable region having the polypeptide sequence of SEQ ID NO:154, and a light chain variable region having the polypeptide sequence of SEQ ID NO:157;
  n. a heavy chain variable region having the polypeptide sequence of SEQ ID NO:155, and a light chain variable region having the polypeptide sequence of SEQ ID NO:157;
  o. a heavy chain variable region having the polypeptide sequence of SEQ ID NO:156, and a light chain variable region having the polypeptide sequence of SEQ ID NO:158;
  p. a heavy chain variable region having the polypeptide sequence of SEQ ID NO:159, and a light chain variable region having the polypeptide sequence of SEQ ID NO:163;
  q. a heavy chain variable region having the polypeptide sequence of SEQ ID NO:159, and a light chain variable region having the polypeptide sequence of SEQ ID NO:164;
  r. a heavy chain variable region having the polypeptide sequence of SEQ ID NO:160, and a light chain variable region having the polypeptide sequence of SEQ ID NO:163;

s. a heavy chain variable region having the polypeptide sequence of SEQ ID NO:160, and a light chain variable region having the polypeptide sequence of SEQ ID NO:164;

t. a heavy chain variable region having the polypeptide sequence of SEQ ID NO:161, and a light chain variable region having the polypeptide sequence of SEQ ID NO:165; or u. a heavy chain variable region having the polypeptide sequence of SEQ ID NO:162, and a light chain variable region having the polypeptide sequence of SEQ ID NO:165.

Also provided are isolated nucleic acids encoding the monoclonal antibodies or antigen-binding fragments thereof of the invention.

Also provided are vectors comprising the isolated nucleic acids encoding the monoclonal antibodies or antigen-binding fragments thereof of the invention.

Also provided are host cells comprising the vectors comprising the isolated nucleic acids encoding the monoclonal antibodies or antigen-binding fragments thereof of the invention.

In certain embodiments, provided is a pharmaceutical composition comprising an isolated monoclonal antibody or antigen-binding fragment thereof of the invention and a pharmaceutically acceptable carrier.

Also provided are methods of specifically targeting CLDN18.2, but not CLDN18.1, on a cancer cell surface in a subject in need thereof, comprising administering to the subject a pharmaceutical composition of the invention.

Also provided are methods of treating cancer in a subject in need thereof, comprising administering to the subject the pharmaceutical compositions of the invention. The cancer can be any liquid or solid cancer, for example, it can be selected from, but not limited to, a lung cancer, a gastric cancer, an esophageal cancer, a bile duct cancer, a cholangiocarcinoma, a colon cancer, a hepatocellular carcinoma, a renal cell carcinoma, a bladder urothelial carcinoma, a metastatic melanoma, a breast cancer, an ovarian cancer, a cervical cancer, a head and neck cancer, a pancreatic cancer, a glioma, a glioblastoma, and other solid tumors, and a non-Hodgkin's lymphoma (NHL), an acute lymphocytic leukemia (ALL), a chronic lymphocytic leukemia (CLL), a chronic myelogenous leukemia (CIVIL), a multiple myeloma (MM), an acute myeloid leukemia (AML), and other liquid tumors.

Also provided are methods of treating an inflammatory disease in a subject in need thereof, comprising administering to the subject a pharmaceutical composition of the invention.

Also provided are methods of producing a monoclonal antibody or antigen-binding fragment thereof of the invention, comprising culturing a cell comprising a nucleic acid encoding the monoclonal antibody or antigen-binding fragment thereof under conditions to produce the monoclonal antibody or antigen-binding fragment thereof, and recovering the antibody or antigen-binding fragment thereof from the cell or culture.

Also provided are methods of producing a pharmaceutical composition comprising a monoclonal antibody or antigen-binding fragment thereof of the invention, comprising combining the monoclonal antibody or antigen-binding fragment thereof with a pharmaceutically acceptable carrier to obtain the pharmaceutical composition.

Also provided are methods of determining the level of CLDN18.2 in a subject. The methods comprise (a) obtaining a sample from the subject; (b) contacting the sample with an antibody or antigen-binding fragment thereof of the invention; and (c) determining the level of CLDN18.2 in the subject. In certain embodiments, the sample is a tissue sample. The tissue sample can, for example, be a cancer tissue sample. In certain embodiments, the sample is a blood sample.

BRIEF DESCRIPTION OF THE DRAWINGS

The foregoing summary, as well as the following detailed description of preferred embodiments of the present application, will be better understood when read in conjunction with the appended drawings. It should be understood, however, that the application is not limited to the precise embodiments shown in the drawings.

DETAILED DESCRIPTION OF THE INVENTION

Figure 1A:
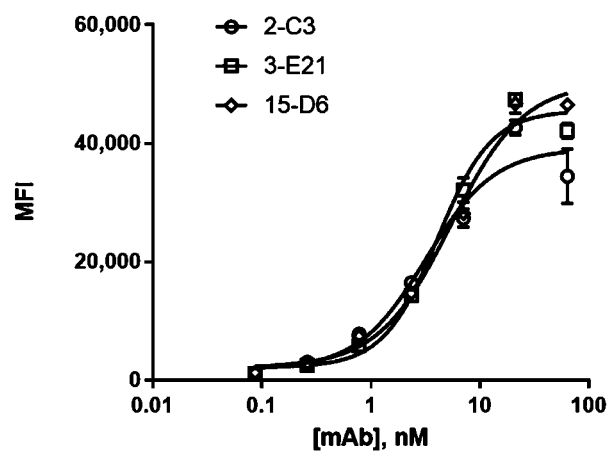
FIGS. 1A-1D show the dose-dependent binding of purified chimeric anti-CLDN18.2 mAbs (VH and VL regions of mouse mAbs fused to the constant regions of human IgG1 heavy chain and kappa light chain, respectively) to a HEK293 cell pool stably transfected with full-length human CLDN18.2 by FACS analysis.
Figure 1B:
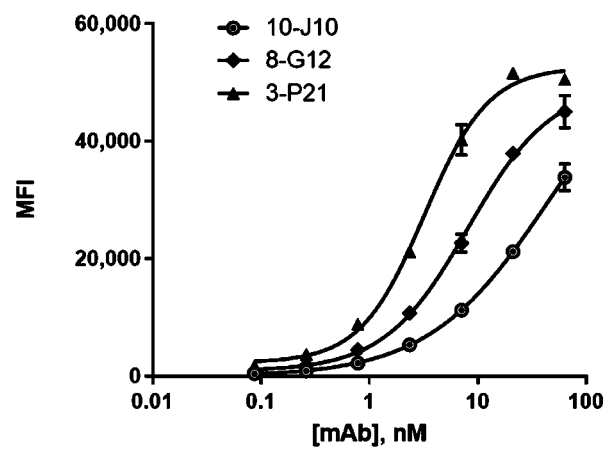
Figure 1C:
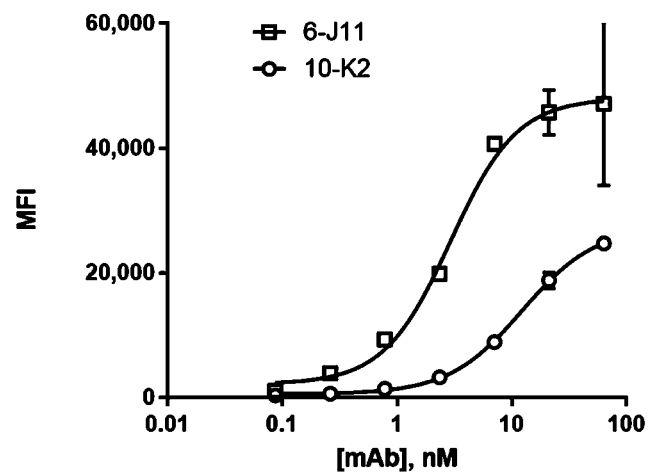
Figure 1D:
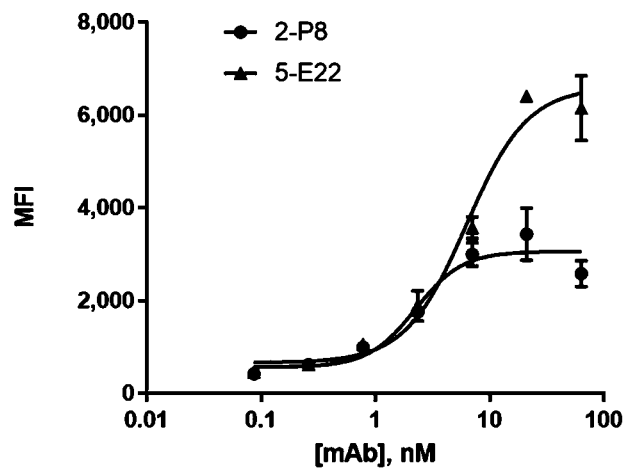
Figure 2A:
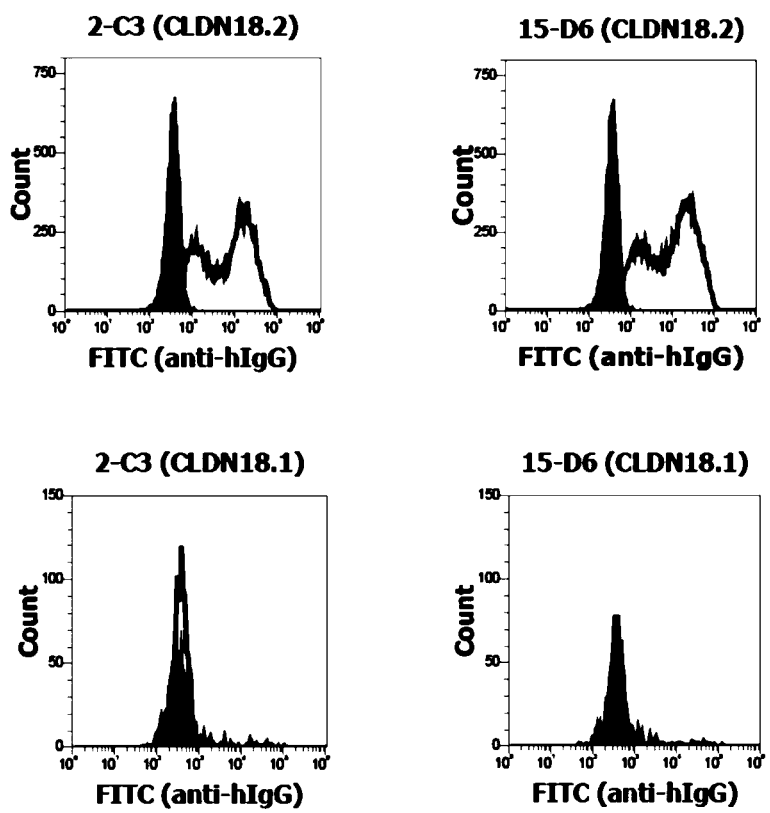
FIGS. 2A-2E show the selective binding of chimeric anti-CLDN18.2 mAbs to CLDN18.2 compared with CLDN18.1. HEK293 cell pools stably transfected with full-length human CLDN18.2 and CLDN18.1, respectively, were used in the experiment. The shaded gray peak is representative of the treatment group incubated with only the secondary antibody and the open black peak is representative of the treatment group incubated with both primary chimeric mAb and the secondary antibody.
Figure 2B:
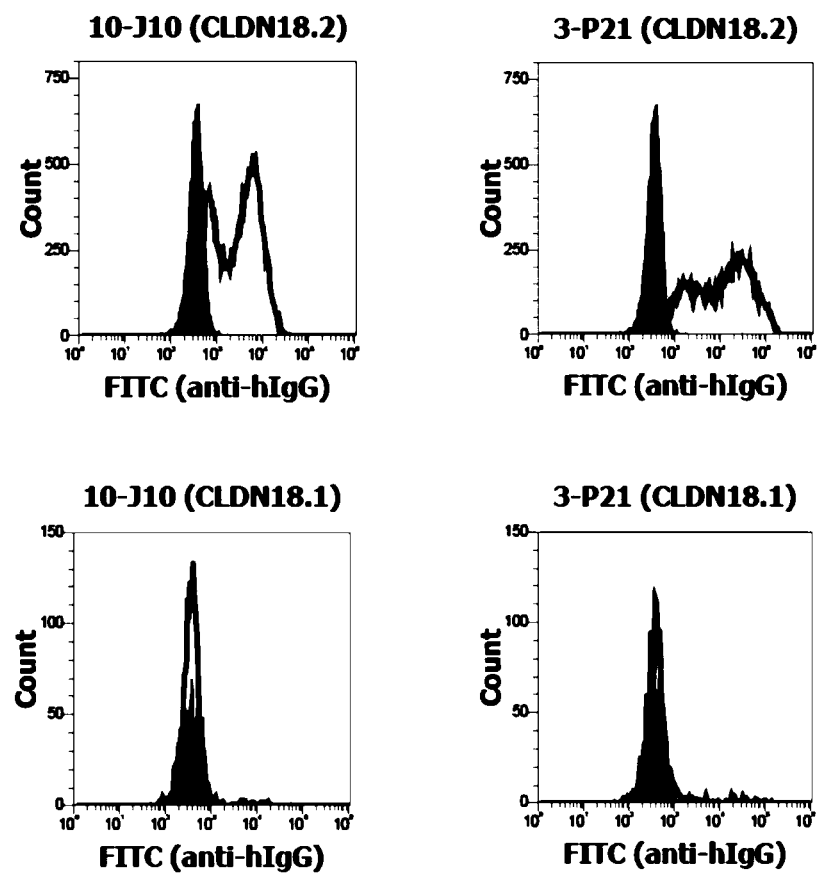
Figure 2C:
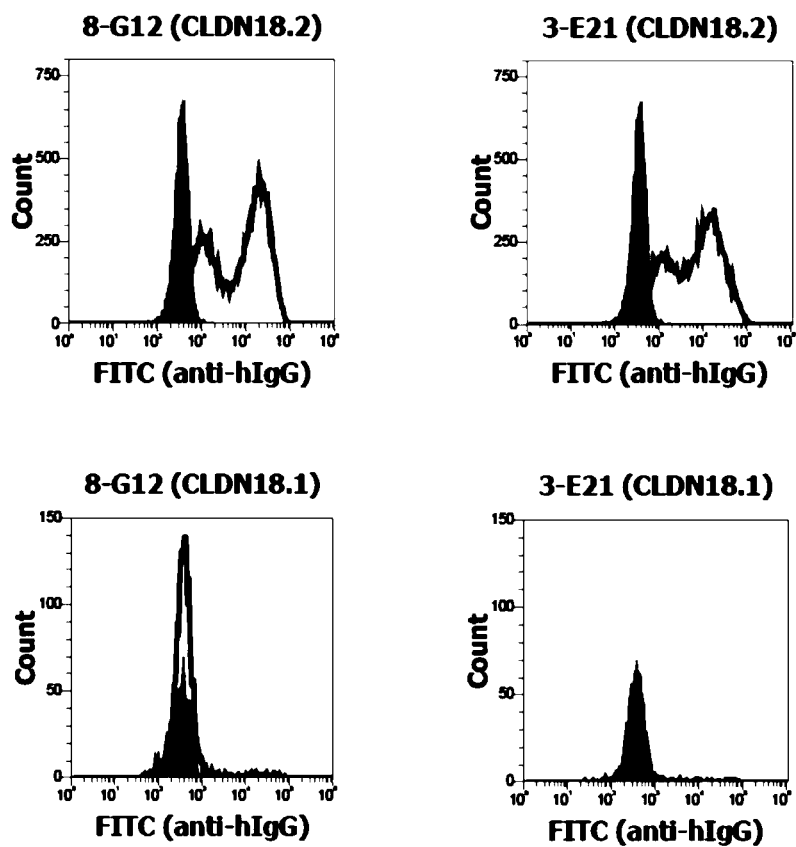
Figure 2D:
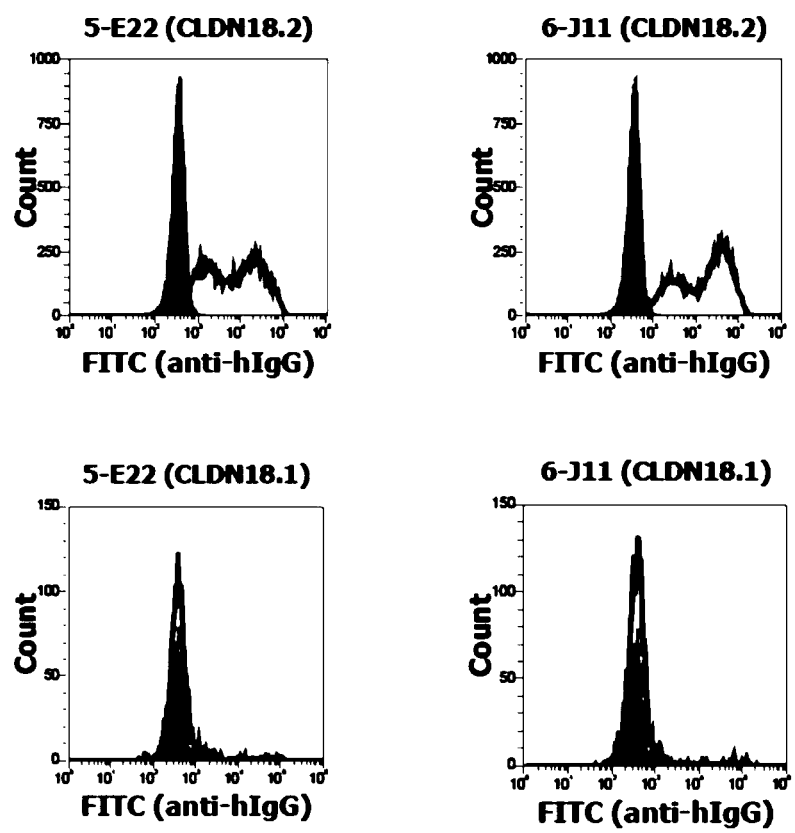
Figure 2E:
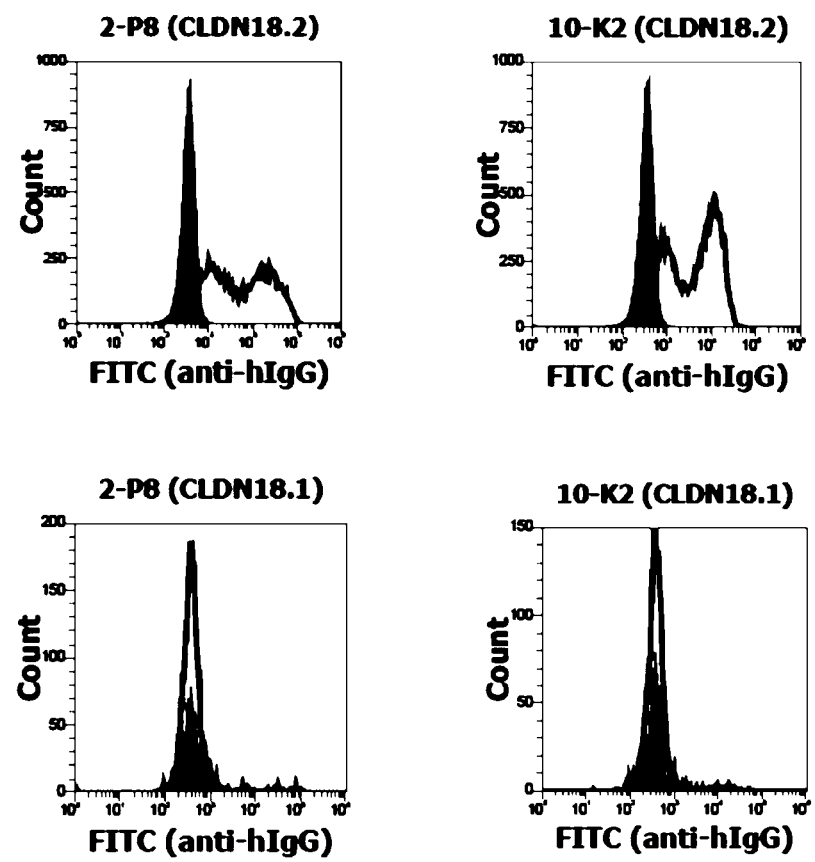

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification.

It must be noted that as used herein and in the appended claims, the singular forms "a," "an," and "the" include plural reference unless the context clearly dictates otherwise.

Unless otherwise stated, any numerical values, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

Unless otherwise indicated, the term "at least" preceding a series of elements is to be understood to refer to every element in the series. Those skilled in the art will recognize or be able to ascertain using no more than routine experimentation, many equivalents to the specific embodiments of the invention described herein. Such equivalents are intended to be encompassed by the invention.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers and are intended to be non-exclusive or open-ended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

As used herein, the term "consists of," or variations such as "consist of" or "consisting of," as used throughout the specification and claims, indicate the inclusion of any recited integer or group of integers, but that no additional integer or group of integers can be added to the specified method, structure, or composition.

As used herein, the term "consists essentially of," or variations such as "consist essentially of" or "consisting essentially of," as used throughout the specification and claims, indicate the inclusion of any recited integer or group of integers, and the optional inclusion of any recited integer or group of integers that do not materially change the basic or novel properties of the specified method, structure or composition. See M.P.E.P. § 2111.03.

As used herein, "subject" means any animal, preferably a mammal, most preferably a human. The term "mammal" as used herein, encompasses any mammal. Examples of mammals include, but are not limited to, cows, horses, sheep, pigs, cats, dogs, mice, rats, rabbits, guinea pigs, monkeys, humans, etc., more preferably a human.

The words "right," "left," "lower," and "upper" designate directions in the drawings to which reference is made.

It should also be understood that the terms "about," "approximately," "generally," "substantially," and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

The terms "identical" or percent "identity," in the context of two or more nucleic acids or polypeptide sequences (e.g., anti-CLDN18.2 antibodies and polynucleotides that encode them, CLDN18.2 polypeptides and CLDN18.2 polynucleotides that encode them), refer to two or more sequences or subsequences that are the same or have a specified percentage of amino acid residues or nucleotides that are the same, when compared and aligned for maximum correspondence, as measured using one of the following sequence comparison algorithms or by visual inspection.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) J. Mol. Biol. 215: 403-410 and Altschul et al. (1997) Nucleic Acids Res. 25: 3389-3402, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased.

Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89:10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions.

Antibodies

The invention generally relates to isolated anti-CLDN18.2 antibodies, nucleic acids and expression vectors encoding the antibodies, recombinant cells containing the vectors, and compositions comprising the antibodies. Methods of making the antibodies, and methods of using the antibodies to treat diseases including cancer and inflammatory diseases. The antibodies of the invention possess one or more desirable functional properties, including but not limited to high-affinity binding to CLDN18.2, high specificity to CLDN18.2, the ability to stimulate complement-dependent cytotoxicity (CDC), antibody-dependent phagocytosis (ADPC), and/or antibody-dependent cellular-mediated cytotoxicity (ADCC) against cells expressing CLDN18.2, and the ability to inhibit tumor growth in subjects and animal models when administered alone or in combination with other anti-cancer therapies.

In a general aspect, the invention relates to isolated monoclonal antibodies or antigen-binding fragments thereof that bind CLDN18.2.

As used herein, the term "antibody" is used in a broad sense and includes immunoglobulin or antibody molecules including human, humanized, composite and chimeric antibodies and antibody fragments that are monoclonal or polyclonal. In general, antibodies are proteins or peptide chains that exhibit binding specificity to a specific antigen. Antibody structures are well known. Immunoglobulins can be assigned to five major classes (i.e., IgA, IgD, IgE, IgG and IgM), depending on the heavy chain constant domain amino acid sequence. IgA and IgG are further sub-classified as the isotypes IgA1, IgA2, IgG1, IgG2, IgG3 and IgG4. Accordingly, the antibodies of the invention can be of any of the five major classes or corresponding sub-classes. Preferably, the antibodies of the invention are IgG1, IgG2, IgG3 or IgG4. Antibody light chains of vertebrate species can be assigned to one of two clearly distinct types, namely kappa and lambda, based on the amino acid sequences of their constant domains. Accordingly, the antibodies of the invention can contain a kappa or lambda light chain constant domain. According to particular embodiments, the antibodies of the invention include heavy and/or light chain constant regions from rat or human antibodies. In addition to the heavy and light constant domains, antibodies contain an antigen-binding region that is made up of a light chain variable region and a heavy chain variable region, each of which contains three domains (i.e., complementarity determining regions 1-3; CDR1, CDR2, and CDR3). The light chain variable region domains are alternatively referred to as LCDR1, LCDR2, and LCDR3, and the heavy chain variable region domains are alternatively referred to as HCDR1, HCDR2, and HCDR3.

As used herein, the term an "isolated antibody" refers to an antibody which is substantially free of other antibodies having different antigenic specificities (e.g., an isolated antibody that specifically binds to CLDN18.2 is substantially free of antibodies that do not bind to CLDN18.2). In addition, an isolated antibody is substantially free of other cellular material and/or chemicals.

As used herein, the term "monoclonal antibody" refers to an antibody obtained from a population of substantially homogeneous antibodies, i.e., the individual antibodies comprising the population are identical except for possible naturally occurring mutations that may be present in minor amounts. The monoclonal antibodies of the invention can be made by the hybridoma method, phage display technology, single lymphocyte gene cloning technology, or by recombinant DNA methods. For example, the monoclonal antibodies can be produced by a hybridoma which includes a B cell obtained from a transgenic nonhuman animal, such as a transgenic mouse or rat, having a genome comprising a human heavy chain transgene and a light chain transgene.

As used herein, the term "antigen-binding fragment" refers to an antibody fragment such as, for example, a diabody, a Fab, a Fab', a F(ab')2, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), a single domain antibody (sdab) an scFv dimer (bivalent diabody), a multi-specific antibody formed from a portion of an antibody comprising one or more CDRs, a camelized single domain antibody, a nanobody, a domain antibody, a bivalent domain antibody, or any other antibody fragment that binds to an antigen but does not comprise a complete antibody structure. An antigen-binding fragment is capable of binding to the same antigen to which the parent antibody or a parent antibody fragment binds. According to particular embodiments, the antigen-binding fragment comprises a light chain variable region, a light chain constant region, and an Fd segment of the heavy chain. According to other particular embodiments, the antigen-binding fragment comprises Fab and F(ab').

As used herein, the term "single-chain antibody" refers to a conventional single-chain antibody in the field, which comprises a heavy chain variable region and a light chain variable region connected by a short peptide of about 15 to about 20 amino acids. As used herein, the term "single domain antibody" refers to a conventional single domain antibody in the field, which comprises a heavy chain variable region and a heavy chain constant region or which comprises only a heavy chain variable region.

As used herein, the term "human antibody" refers to an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide.

As used herein, the term "humanized antibody" refers to a non-human antibody that is modified to increase the sequence homology to that of a human antibody, such that the antigen-binding properties of the antibody are retained, but its antigenicity in the human body is reduced.

As used herein, the term "chimeric antibody" refers to an antibody wherein the amino acid sequence of the immunoglobulin molecule is derived from two or more species. The variable region of both the light and heavy chains often corresponds to the variable region of an antibody derived from one species of mammal (e.g., mouse, rat, rabbit, etc.) having the desired specificity, affinity, and capability, while the constant regions correspond to the sequences of an antibody derived from another species of mammal (e.g., human) to avoid eliciting an immune response in that species.

As used herein, the term "multispecific antibody" refers to an antibody that comprises a plurality of immunoglobulin variable domain sequences, wherein a first immunoglobulin variable domain sequence of the plurality has binding specificity for a first epitope and a second immunoglobulin variable domain sequence of the plurality has binding specificity for a second epitope. In an embodiment, the first and second epitopes are on the same antigen, e.g., the same protein (or subunit of a multimeric protein). In an embodiment, the first and second epitopes overlap or substantially overlap. In an embodiment, the first and second epitopes do not overlap or do not substantially overlap. In an embodiment, the first and second epitopes are on different antigens, e.g., different proteins (or different subunits of a multimeric protein). In an embodiment, a multispecific antibody comprises a third, fourth, or fifth immunoglobulin variable domain. In an embodiment, a multispecific antibody is a bispecific antibody molecule, a trispecific antibody molecule, or a tetraspecific antibody molecule.

As used herein, the term "bispecific antibody" refers to a multispecific antibody that binds no more than two epitopes or two antigens. A bispecific antibody is characterized by a first immunoglobulin variable domain sequence which has binding specificity for a first epitope and a second immunoglobulin variable domain sequence that has binding specificity for a second epitope. In an embodiment, the first and second epitopes are on the same antigen, e.g., the same protein (or subunit of a multimeric protein). In an embodiment, the first and second epitopes overlap or substantially overlap. In an embodiment, the first and second epitopes are on different antigens, e.g., different proteins (or different subunits of a multimeric protein). In an embodiment, a bispecific antibody comprises a heavy chain variable domain sequence and a light chain variable domain sequence which have binding specificity for a first epitope and a heavy chain variable domain sequence and a light chain variable domain sequence which have binding specificity for a second epitope. In an embodiment, a bispecific antibody comprises a half antibody, or fragment thereof, having binding specificity for a first epitope and a half antibody, or fragment thereof, having binding specificity for a second epitope. In an embodiment, a bispecific antibody comprises a scFv, or fragment thereof, having binding specificity for a first epitope, and a scFv, or fragment thereof, having binding specificity for a second epitope. In an embodiment, the first epitope is located on CLDN18.2 and the second epitope is located on PD-1, PD-L1, TIM-3, LAG-3, CTLA-4, EGFR, HER-2, CD19, CD20, CD33, CD3, CD73, CD47, TIP-1, apelin, DLL3, folate receptor alpha, and/or other tumor associated immune suppressors or surface antigens.

As used herein, the term "CLDN18.2" refers to claudin 18 variant 2, claudin-18.2 or claudin-18a2.1, which belongs to the claudin family of transmembrane proteins. CLDN18.2 is specifically expressed on the surface of epithelial cells in stomach (Niimi et al., Mol Cell Biol. 2001; 21:7380-7390) and becomes one of the major structural components of the tight junction between the epithelial cells (Sahin et al., Physiol Rev. 2013; 93:525-569). The term "human CLDN18.2" refers to a CLDN18.2 originated from a human. An exemplary amino acid sequence of a human CLDN18.2 is represented in GenBank Accession No. AAL15637.1 (SEQ ID NO:141).

As used herein, an antibody that "specifically binds to CLDN18.2" refers to an antibody that binds to a CLDN18.2, preferably a human CLDN18.2, with a KD of $1 \times 10^{-7}$ M or less, preferably $1 \times 10^{-8}$ M or less, more preferably $5 \times 10^{-9}$ M or less, $1 \times 10^{-9}$ M or less, $5 \times 10^{-10}$ M or less, or $1 \times 10^{-10}$ M or less. The term "KD" refers to the dissociation constant, which is obtained from the ratio of Kd to Ka (i.e., Kd/Ka) and is expressed as a molar concentration (M). KD values for antibodies can be determined using methods in the art in view of the present disclosure. For example, the KD of an antibody can be determined by using surface plasmon resonance, such as by using a biosensor system, e.g., a Biacore® system, or by using bio-layer interferometry technology, such as an Octet RED96 system.

The smaller the value of the KD of an antibody, the higher affinity that the antibody binds to a target antigen.

According to a particular aspect, the invention relates to an isolated monoclonal antibody or antigen-binding fragment thereof comprising a heavy chain complementarity determining region 1 (HCDR1), a HCDR2, a HCDR3, a light chain complementarity determining region 1 (LCDR1), a LCDR2, and a LCDR3, having the polypeptide sequences of:

(1) SEQ ID NOs: 33, 34, 35, 63, 64 and 65, respectively;
(2) SEQ ID NOs: 21, 22, 23, 51, 52 and 53, respectively;
(3) SEQ ID NOs: 24, 25, 26, 54, 55 and 56, respectively;
(4) SEQ ID NOs: 27, 28, 29, 57, 58 and 59, respectively;
(5) SEQ ID NOs: 30, 31, 32, 60, 61 and 62, respectively;
(6) SEQ ID NOs: 36, 37, 38, 66, 67 and 68, respectively;
(7) SEQ ID NOs: 39, 40, 41, 69, 70 and 71, respectively;

(8) SEQ ID NOs: 42, 43, 44, 72, 73 and 74, respectively;
(9) SEQ ID NOs: 45, 46, 47, 75, 76 and 77, respectively; or
(10) SEQ ID NOs: 48, 49, 50, 78, 79 and 80, respectively;
wherein the antibody or antigen-binding fragment thereof specifically binds CLDN18.2, preferably human CLDN18.2.

According to a particular aspect, the invention relates to an isolated monoclonal antibody or antigen-binding fragment thereof comprising a heavy chain complementarity determining region 1 (HCDR1), a HCDR2, a HCDR3, a light chain complementarity determining region 1 (LCDR1), a LCDR2, and a LCDR3, having the polypeptide sequences of:
  (1) SEQ ID NOs: 93, 94, 95, 123, 124 and 125, respectively;
  (2) SEQ ID NOs: 81, 82, 83, 111, 112 and 113, respectively;
  (3) SEQ ID NOs: 84, 85, 86, 114, 115 and 116, respectively;
  (4) SEQ ID NOs: 87, 88, 89, 117, 118 and 119, respectively;
  (5) SEQ ID NOs: 90, 91, 92, 120, 121 and 122, respectively;
  (6) SEQ ID NOs: 96, 97, 98, 126, 127 and 128, respectively;
  (7) SEQ ID NOs: 99, 100, 101, 129, 130 and 131, respectively;
  (8) SEQ ID NOs: 102, 103, 104, 132, 133 and 134, respectively;
  (9) SEQ ID NOs: 105, 106, 107, 135, 136 and 137, respectively; or
  (10) SEQ ID NOs: 108, 109, 110, 138, 139 and 140, respectively;
wherein the antibody or antigen-binding fragment thereof specifically binds CLDN18.2, preferably human CLDN18.2.

According to another particular aspect, the invention relates to an isolated monoclonal antibody or antigen-binding fragment thereof comprising a heavy chain variable region having a polypeptide sequence at least 85%, preferably 90%, more preferably 95% or more, such as 95%, 96%, 97%, 98%, or 99% identical to one of SEQ ID NOs: 9, 1, 3, 5, 7, 11, 13, 15, 17 or 19, or a light chain variable region having a polypeptide sequence at least 85%, preferably 90%, more preferably 95% or more, such as 95%, 96%, 97%, 98%, or 99% identical to one of SEQ ID NOs: 10, 2, 4, 6, 8, 12, 14, 16, 18 or 20. According to one preferred embodiment, the isolated monoclonal antibody or antigen-binding fragment thereof of the invention comprises a heavy chain variable region having the polypeptide sequence at least 85%, preferably 90%, more preferably 95% or more, such as 95%, 96%, 97%, 98%, or 99% identical to SEQ ID NO: 9, 1, 3, 5, 7, 11, 13, 15, 17 or 19, and a light chain variable region having a polypeptide sequence at least 85%, preferably 90%, more preferably 95% or more, such as 95%, 96%, 97%, 98%, or 99% identical to SEQ ID NO: 10, 2, 4, 6, 8, 12, 14, 16, 18 or 20, respectively.

According to another particular aspect, the invention relates to an isolated monoclonal antibody or antigen-binding fragment thereof of the invention, comprising:
  a. a heavy chain variable region having the polypeptide sequence of SEQ ID NO:9, and a light chain variable region having the polypeptide sequence of SEQ ID NO:10;
  b. a heavy chain variable region having the polypeptide sequence of SEQ ID NO:1, and a light chain variable region having the polypeptide sequence of SEQ ID NO:2;
  c. a heavy chain variable region having the polypeptide sequence of SEQ ID NO:3, and a light chain variable region having the polypeptide sequence of SEQ ID NO:4;
  d. a heavy chain variable region having the polypeptide sequence of SEQ ID NO:5, and a light chain variable region having the polypeptide sequence of SEQ ID NO:6;
  e. a heavy chain variable region having the polypeptide sequence of SEQ ID NO:7, and a light chain variable region having the polypeptide sequence of SEQ ID NO:8;
  f. a heavy chain variable region having the polypeptide sequence of SEQ ID NO:11, and a light chain variable region having the polypeptide sequence of SEQ ID NO:12;
  g. a heavy chain variable region having the polypeptide sequence of SEQ ID NO:13, and a light chain variable region having the polypeptide sequence of SEQ ID NO:14;
  h. a heavy chain variable region having the polypeptide sequence of SEQ ID NO:15, and a light chain variable region having the polypeptide sequence of SEQ ID NO:16;
  i. a heavy chain variable region having the polypeptide sequence of SEQ ID NO:17, and a light chain variable region having the polypeptide sequence of SEQ ID NO:18;
  j. a heavy chain variable region having the polypeptide sequence of SEQ ID NO:19, and a light chain variable region having the polypeptide sequence of SEQ ID NO:20.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 21, 22, 23, 51, 52 and 53, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:1, and a light chain variable region having a polypeptide sequence at least 85%, preferably 90%, more preferably 95% or more, such as 95%, 96%, 97%, 98%, or 99% identical to SEQ ID NO:2. Preferably, the isolated monoclonal antibody or antigen-binding fragment thereof comprises a heavy chain variable region having the polypeptide sequence of SEQ ID NO:1; and a light chain variable region having the polypeptide sequence of SEQ ID NO:2.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 24, 25, 26, 54, 55 and 56, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:3, and a light chain variable region having a polypeptide sequence at least 85%, preferably 90%, more preferably 95% or more, such as 95%, 96%, 97%, 98%, or 99% identical to SEQ ID NO:4. Preferably, the isolated monoclonal antibody or antigen-binding fragment thereof comprises a heavy chain variable region having the polypeptide sequence of SEQ ID NO:3; and a light chain variable region having the polypeptide sequence of SEQ ID NO:4.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 27, 28, 29, 57, 58 and 59, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:5, and a light chain variable region having a polypeptide sequence at least 85%, preferably 90%, more preferably 95% or more, such as 95%, 96%, 97%, 98%, or 99% identical to SEQ ID NO:6. Preferably, the isolated monoclonal antibody or antigen-binding fragment thereof comprises a heavy chain variable region having the polypeptide sequence of SEQ ID NO:5; and a light chain variable region having the polypeptide sequence of SEQ ID NO:6.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 30, 31, 32, 60, 61 and 62, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:7, and a light chain variable region having a polypeptide sequence at least 85%, preferably 90%, more preferably 95% or more, such as 95%, 96%, 97%, 98%, or 99% identical to SEQ ID NO:8. Preferably, the isolated monoclonal antibody or antigen-binding fragment thereof comprises a heavy chain variable region having the polypeptide sequence of SEQ ID NO:7; and a light chain variable region having the polypeptide sequence of SEQ ID NO:8.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 33, 34, 35, 63, 64 and 65, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:9, and a light chain variable region having a polypeptide sequence at least 85%, preferably 90%, more preferably 95% or more, such as 95%, 96%, 97%, 98%, or 99% identical to SEQ ID NO:10. Preferably, the isolated monoclonal antibody or antigen-binding fragment thereof comprises a heavy chain variable region having the polypeptide sequence of SEQ ID NO:9; and a light chain variable region having the polypeptide sequence of SEQ ID NO:10.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 36, 37, 38, 66, 67 and 68, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:11, and a light chain variable region having a polypeptide sequence at least 85%, preferably 90%, more preferably 95% or more, such as 95%, 96%, 97%, 98%, or 99% identical to SEQ ID NO:12. Preferably, the isolated monoclonal antibody or antigen-binding fragment thereof comprises a heavy chain variable region having the polypeptide sequence of SEQ ID NO:11; and a light chain variable region having the polypeptide sequence of SEQ ID NO:12.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 39, 40, 41, 69, 70 and 71, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:13, and a light chain variable region having a polypeptide sequence at least 85%, preferably 90%, more preferably 95% or more, such as 95%, 96%, 97%, 98%, or 99% identical to SEQ ID NO:14. Preferably, the isolated monoclonal antibody or antigen-binding fragment thereof comprises a heavy chain variable region having the polypeptide sequence of SEQ ID NO:13; and a light chain variable region having the polypeptide sequence of SEQ ID NO:14.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 42, 43, 44, 72, 73 and 74, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:15, and a light chain variable region having a polypeptide sequence at least 85%, preferably 90%, more preferably 95% or more, such as 95%, 96%, 97%, 98%, or 99% identical to SEQ ID NO:16. Preferably, the isolated monoclonal antibody or antigen-binding fragment thereof comprises a heavy chain variable region having the polypeptide sequence of SEQ ID NO:15; and a light chain variable region having the polypeptide sequence of SEQ ID NO:16.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 45, 46, 47, 75, 76 and 77, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:17, and a light chain variable region having a polypeptide sequence at least 85%, preferably 90%, more preferably 95% or more, such as 95%, 96%, 97%, 98%, or 99% identical to SEQ ID NO:18. Preferably, the isolated monoclonal antibody or antigen-binding fragment thereof comprises a heavy chain variable region having the polypeptide sequence of SEQ ID NO:17; and a light chain variable region having the polypeptide sequence of SEQ ID NO:18.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 48, 49, 50, 78, 79 and 80, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:19, and a light chain variable region having a polypeptide sequence at least 85%, preferably 90%, more preferably 95% or more, such as 95%, 96%, 97%, 98%, or 99% identical to SEQ ID NO:20. Preferably, the isolated monoclonal antibody or antigen-binding fragment thereof comprises a heavy chain variable region having the polypeptide sequence of SEQ ID NO:19; and a light chain variable region having the polypeptide sequence of SEQ ID NO:20.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 81, 82, 83, 111, 112 and 113, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:1, and a light chain variable region having a polypeptide sequence at least 85%, preferably 90%, more preferably 95% or more, such as 95%, 96%, 97%, 98%, or 99% identical to SEQ ID NO:2. Preferably, the isolated monoclonal antibody or antigen-binding fragment thereof comprises a heavy chain variable region having the polypeptide sequence of SEQ ID NO:1; and a light chain variable region having the polypeptide sequence of SEQ ID NO:2.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 84, 85, 86, 114, 115 and 116, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:3, and a light chain variable region having a polypeptide sequence at least 85%, preferably 90%, more preferably 95% or more, such as 95%, 96%, 97%, 98%, or 99% identical to SEQ ID NO:4. Preferably, the isolated monoclonal antibody or antigen-binding fragment thereof comprises a heavy chain variable region having the polypeptide sequence of SEQ ID NO:3; and a light chain variable region having the polypeptide sequence of SEQ ID NO:4.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 87, 88, 89, 117, 118 and 119, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:5, and a light chain variable region having a polypeptide sequence at least 85%, preferably 90%, more preferably 95% or more, such as 95%, 96%, 97%, 98%, or 99% identical to SEQ ID NO:6. Preferably, the isolated monoclonal antibody or antigen-binding fragment thereof comprises a heavy chain variable region having the polypeptide sequence of SEQ ID NO:5; and a light chain variable region having the polypeptide sequence of SEQ ID NO:6.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 90, 91, 92, 120, 121 and 122, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:7, and a light chain variable region having a polypeptide sequence at least 85%, preferably 90%, more preferably 95% or more, such as 95%, 96%, 97%, 98%, or 99% identical to SEQ ID NO:8. Preferably, the isolated monoclonal antibody or antigen-binding fragment thereof comprises a heavy chain variable region having the polypeptide sequence of SEQ ID NO:7; and a light chain variable region having the polypeptide sequence of SEQ ID NO:8.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 93, 94, 95, 123, 124 and 125, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:9, and a light chain variable region having a polypeptide sequence at least 85%, preferably 90%, more preferably 95% or more, such as 95%, 96%, 97%, 98%, or 99% identical to SEQ ID NO:10. Preferably, the isolated monoclonal antibody or antigen-binding fragment thereof comprises a heavy chain variable region having the polypeptide sequence of SEQ ID NO:9; and a light chain variable region having the polypeptide sequence of SEQ ID NO:10.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 96, 97, 98, 126, 127 and 128, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:11, and a light chain variable region having a polypeptide sequence at least 85%, preferably 90%, more preferably 95% or more, such as 95%, 96%, 97%, 98%, or 99% identical to SEQ ID NO:12. Preferably, the isolated monoclonal antibody or antigen-binding fragment thereof comprises a heavy chain variable region having the polypeptide sequence of SEQ ID NO:11; and a light chain variable region having the polypeptide sequence of SEQ ID NO:12.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 99, 100, 101, 129, 130 and 131, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:13, and a light chain variable region having a polypeptide sequence at least 85%, preferably 90%, more preferably 95% or more, such as 95%, 96%, 97%, 98%, or 99% identical to SEQ ID NO:14. Preferably, the isolated monoclonal antibody or antigen-binding fragment thereof comprises a heavy chain variable region having the polypeptide sequence of SEQ ID NO:13; and a light chain variable region having the polypeptide sequence of SEQ ID NO:14.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 102, 103, 104, 132, 133 and 134, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:15, and a light chain variable region having a polypeptide sequence at least 85%, preferably 90%, more preferably 95% or more, such as 95%, 96%, 97%, 98%, or 99% identical to SEQ ID NO:16. Preferably, the isolated monoclonal antibody or antigen-binding fragment thereof comprises a heavy chain variable region having the polypeptide sequence of SEQ ID NO:15; and a light chain variable region having the polypeptide sequence of SEQ ID NO:16.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 105, 106, 107, 135, 136 and 137, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:17, and a light chain variable region having a polypeptide sequence at least 85%, preferably 90%, more preferably 95% or more, such as 95%, 96%, 97%, 98%, or 99% identical to SEQ ID NO:18. Preferably, the isolated monoclonal antibody or antigen-binding fragment thereof comprises a heavy chain variable region having the polypeptide sequence of SEQ ID NO:17; and a light chain variable region having the polypeptide sequence of SEQ ID NO:18.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 108, 109, 110, 138, 139 and 140, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:19, and a light chain variable region having a polypeptide sequence at least 85%, preferably 90%, more preferably 95% or more, such as 95%, 96%, 97%, 98%, or 99% identical to SEQ ID NO:20. Preferably, the isolated monoclonal antibody or antigen-binding fragment thereof comprises a heavy chain variable region having the polypeptide sequence of SEQ ID NO:19; and a light chain variable region having the polypeptide sequence of SEQ ID NO:20.

According to another particular aspect, the invention relates to an isolated monoclonal antibody or antigen-binding fragment thereof of the invention, wherein the antibody or antigen-binding fragment thereof is chimeric.

According to another particular aspect, the invention relates to an isolated monoclonal antibody or antigen-binding fragment thereof of the invention, wherein the antibody or antigen-binding fragment thereof is human or humanized.

According to another particular aspect, the invention relates to an isolated humanized monoclonal antibody or antigen-binding fragment thereof, wherein the isolated humanized antibody or antigen-binding fragment thereof comprises:

a. a heavy chain variable region having the polypeptide sequence of SEQ ID NO:142, and a light chain variable region having the polypeptide sequence of SEQ ID NO:144;

b. a heavy chain variable region having the polypeptide sequence of SEQ ID NO:142, and a light chain variable region having the polypeptide sequence of SEQ ID NO:145;

c. a heavy chain variable region having the polypeptide sequence of SEQ ID NO:143, and a light chain variable region having the polypeptide sequence of SEQ ID NO:144;

d. a heavy chain variable region having the polypeptide sequence of SEQ ID NO:143, and a light chain variable region having the polypeptide sequence of SEQ ID NO:145;

e. a heavy chain variable region having the polypeptide sequence of SEQ ID NO:146, and a light chain variable region having the polypeptide sequence of SEQ ID NO:148;

f. a heavy chain variable region having the polypeptide sequence of SEQ ID NO:146, and a light chain variable region having the polypeptide sequence of SEQ ID NO:149;

g. a heavy chain variable region having the polypeptide sequence of SEQ ID NO:146, and a light chain variable region having the polypeptide sequence of SEQ ID NO:150;

h. a heavy chain variable region having the polypeptide sequence of SEQ ID NO:147, and a light chain variable region having the polypeptide sequence of SEQ ID NO:148;

i. a heavy chain variable region having the polypeptide sequence of SEQ ID NO:147, and a light chain variable region having the polypeptide sequence of SEQ ID NO:149;

j. a heavy chain variable region having the polypeptide sequence of SEQ ID NO:147, and a light chain variable region having the polypeptide sequence of SEQ ID NO:150;

k. a heavy chain variable region having the polypeptide sequence of SEQ ID NO:151, and a light chain variable region having the polypeptide sequence of SEQ ID NO:153;

l. a heavy chain variable region having the polypeptide sequence of SEQ ID NO:152, and a light chain variable region having the polypeptide sequence of SEQ ID NO:153;

m. a heavy chain variable region having the polypeptide sequence of SEQ ID NO:154, and a light chain variable region having the polypeptide sequence of SEQ ID NO:157;

n. a heavy chain variable region having the polypeptide sequence of SEQ ID NO:155, and a light chain variable region having the polypeptide sequence of SEQ ID NO:157;

o. a heavy chain variable region having the polypeptide sequence of SEQ ID NO:156, and a light chain variable region having the polypeptide sequence of SEQ ID NO:158;

p. a heavy chain variable region having the polypeptide sequence of SEQ ID NO:159, and a light chain variable region having the polypeptide sequence of SEQ ID NO:163;
q. a heavy chain variable region having the polypeptide sequence of SEQ ID NO:159, and a light chain variable region having the polypeptide sequence of SEQ ID NO:164;
r. a heavy chain variable region having the polypeptide sequence of SEQ ID NO:160, and a light chain variable region having the polypeptide sequence of SEQ ID NO:163;
s. a heavy chain variable region having the polypeptide sequence of SEQ ID NO:160, and a light chain variable region having the polypeptide sequence of SEQ ID NO:164;
t. a heavy chain variable region having the polypeptide sequence of SEQ ID NO:161, and a light chain variable region having the polypeptide sequence of SEQ ID NO:165; or
u. a heavy chain variable region having the polypeptide sequence of SEQ ID NO:162, and a light chain variable region having the polypeptide sequence of SEQ ID NO:165.

In another general aspect, the invention relates to an isolated nucleic acid encoding a monoclonal antibody or antigen-binding fragment thereof of the invention. It will be appreciated by those skilled in the art that the coding sequence of a protein can be changed (e.g., replaced, deleted, inserted, etc.) without changing the amino acid sequence of the protein. Accordingly, it will be understood by those skilled in the art that nucleic acid sequences encoding monoclonal antibodies or antigen-binding fragments thereof of the invention can be altered without changing the amino acid sequences of the proteins.

In another general aspect, the invention relates to a vector comprising an isolated nucleic acid encoding a monoclonal antibody or antigen-binding fragment thereof of the invention. Any vector known to those skilled in the art in view of the present disclosure can be used, such as a plasmid, a cosmid, a phage vector or a viral vector. In some embodiments, the vector is a recombinant expression vector such as a plasmid. The vector can include any element to establish a conventional function of an expression vector, for example, a promoter, ribosome binding element, terminator, enhancer, selection marker, and origin of replication. The promoter can be a constitutive, inducible, or repressible promoter. A number of expression vectors capable of delivering nucleic acids to a cell are known in the art and can be used herein for production of an antibody or antigen-binding fragment thereof in the cell. Conventional cloning techniques or artificial gene synthesis can be used to generate a recombinant expression vector according to embodiments of the invention.

In another general aspect, the invention relates to a host cell comprising an isolated nucleic acid encoding a monoclonal antibody or antigen-binding fragment thereof of the invention. Any host cell known to those skilled in the art in view of the present disclosure can be used for recombinant expression of antibodies or antigen-binding fragments thereof of the invention. In some embodiments, the host cells are *E. coli* TG1 or BL21 cells (for expression of, e.g., an scFv or Fab antibody), CHO-DG44 or CHO-K1 cells or HEK293 cells (for expression of, e.g., a full-length IgG antibody). According to particular embodiments, the recombinant expression vector is transformed into host cells by conventional methods such as chemical transfection, heat shock, or electroporation, where it is stably integrated into the host cell genome such that the recombinant nucleic acid is effectively expressed.

In another general aspect, the invention relates to a method of producing a monoclonal antibody or antigen-binding fragment thereof of the invention, comprising culturing a cell comprising a nucleic acid encoding the monoclonal antibody or antigen-binding fragment thereof under conditions to produce a monoclonal antibody or antigen-binding fragment thereof of the invention, and recovering the antibody or antigen-binding fragment thereof from the cell or cell culture (e.g., from the supernatant). Expressed antibodies or antigen-binding fragments thereof can be harvested from the cells and purified according to conventional techniques known in the art and as described herein.

Pharmaceutical Compositions

In another general aspect, the invention relates to a pharmaceutical composition, comprising an isolated monoclonal antibody or antigen-binding fragment thereof of the invention and a pharmaceutically acceptable carrier. The term "pharmaceutical composition" as used herein means a product comprising an antibody of the invention together with a pharmaceutically acceptable carrier. Antibodies of the invention and compositions comprising them are also useful in the manufacture of a medicament for therapeutic applications mentioned herein.

As used herein, the term "carrier" refers to any excipient, diluent, filler, salt, buffer, stabilizer, solubilizer, oil, lipid, lipid containing vesicle, microsphere, liposomal encapsulation, or other material well known in the art for use in pharmaceutical formulations. It will be understood that the characteristics of the carrier, excipient or diluent will depend on the route of administration for a particular application. As used herein, the term "pharmaceutically acceptable carrier" refers to a non-toxic material that does not interfere with the effectiveness of a composition according to the invention or the biological activity of a composition according to the invention. According to particular embodiments, in view of the present disclosure, any pharmaceutically acceptable carrier suitable for use in an antibody pharmaceutical composition can be used in the invention.

The formulation of pharmaceutically active ingredients with pharmaceutically acceptable carriers is known in the art, e.g., Remington: The Science and Practice of Pharmacy (e.g. 21st edition (2005), and any later editions). Non-limiting examples of additional ingredients include: buffers, diluents, solvents, tonicity regulating agents, preservatives, stabilizers, and chelating agents. One or more pharmaceutically acceptable carrier can be used in formulating the pharmaceutical compositions of the invention.

In one embodiment of the invention, the pharmaceutical composition is a liquid formulation. A preferred example of a liquid formulation is an aqueous formulation, i.e., a formulation comprising water. The liquid formulation can comprise a solution, a suspension, an emulsion, a microemulsion, a gel, and the like. An aqueous formulation typically comprises at least 50% w/w water, or at least 60%, 70%, 75%, 80%, 85%, 90%, or at least 95% w/w of water.

In one embodiment, the pharmaceutical composition can be formulated as an injectable which can be injected, for example, via an injection device (e.g., a syringe or an infusion pump). The injection can be delivered subcutaneously, intramuscularly, intraperitoneally, intravitreally, or intravenously, for example.

In another embodiment, the pharmaceutical composition is a solid formulation, e.g., a freeze-dried or spray-dried composition, which can be used as is, or whereto the physician or the patient adds solvents, and/or diluents prior to use. Solid dosage forms can include tablets, such as compressed tablets, and/or coated tablets, and capsules (e.g., hard or soft gelatin capsules). The pharmaceutical composition can also be in the form of sachets, dragees, powders, granules, lozenges, or powders for reconstitution, for example.

The dosage forms may be immediate release, in which case they can comprise a water-soluble or dispersible carrier, or they can be delayed release, sustained release, or modified release, in which case they can comprise water-insoluble polymers that regulate the rate of dissolution of the dosage form in the gastrointestinal tract or under the skin.

In other embodiments, the pharmaceutical composition can be delivered intranasally, intrabuccally, or sublingually.

The pH in an aqueous formulation can be between pH 3 and pH 10. In one embodiment of the invention, the pH of the formulation is from about 7.0 to about 9.5. In another embodiment of the invention, the pH of the formulation is from about 3.0 to about 7.0.

In another embodiment of the invention, the pharmaceutical composition comprises a buffer. Non-limiting examples of buffers include: arginine, aspartic acid, bicine, citrate, disodium hydrogen phosphate, fumaric acid, glycine, glycylglycine, histidine, lysine, maleic acid, malic acid, sodium acetate, sodium carbonate, sodium dihydrogen phosphate, sodium phosphate, succinate, tartaric acid, tricine, and tris(hydroxymethyl)-aminomethane, and mixtures thereof. The buffer can be present individually or in the aggregate, in a concentration from about 0.01 mg/ml to about 50 mg/ml, for example from about 0.1 mg/ml to about 20 mg/ml. Pharmaceutical compositions comprising each one of these specific buffers constitute alternative embodiments of the invention.

In another embodiment of the invention, the pharmaceutical composition comprises a preservative. Non-limiting examples of preservatives include: benzethonium chloride, benzoic acid, benzyl alcohol, bronopol, butyl 4-hydroxybenzoate, chlorobutanol, chlorocresol, chlorohexidine, chlorphenesin, o-cresol, m-cresol, p-cresol, ethyl 4-hydroxybenzoate, imidurea, methyl 4-hydroxybenzoate, phenol, 2-phenoxyethanol, 2-phenylethanol, propyl 4-hydroxybenzoate, sodium dehydroacetate, thiomersal, and mixtures thereof. The preservative can be present individually or in the aggregate, in a concentration from about 0.01 mg/ml to about 50 mg/ml, for example from about 0.1 mg/ml to about 20 mg/ml. Pharmaceutical compositions comprising each one of these specific preservatives constitute alternative embodiments of the invention.

In another embodiment of the invention, the pharmaceutical composition comprises an isotonic agent. Non-limiting examples of the embodiment include a salt (such as sodium chloride), an amino acid (such as glycine, histidine, arginine, lysine, isoleucine, aspartic acid, tryptophan, and threonine), an alditol (such as glycerol, 1,2-propanediol propyleneglycol), 1,3-propanediol, and 1,3-butanediol), polyethyleneglycol (e.g. PEG400), and mixtures thereof. Another example of an isotonic agent includes a sugar. Non-limiting examples of sugars may be mono-, di-, or polysaccharides, or water-soluble glucans, including for example fructose, glucose, mannose, sorbose, xylose, maltose, lactose, sucrose, trehalose, dextran, pullulan, dextrin, cyclodextrin, alpha and beta-HPCD, soluble starch, hydroxyethyl starch, and sodium carboxymethylcellulose. Another example of an isotonic agent is a sugar alcohol, wherein the term "sugar alcohol" is defined as a C(4-8) hydrocarbon having at least one —OH group. Non-limiting examples of sugar alcohols include mannitol, sorbitol, inositol, galactitol, dulcitol, xylitol, and arabitol. The isotonic agent can be present individually or in the aggregate, in a concentration from about 0.01 mg/ml to about 50 mg/ml, for example from about 0.1 mg/ml to about 20 mg/ml. Pharmaceutical compositions comprising each one of these specific isotonic agents constitute alternative embodiments of the invention.

In another embodiment of the invention, the pharmaceutical composition comprises a chelating agent. Non-limiting examples of chelating agents include citric acid, aspartic acid, salts of ethylenediaminetetraacetic acid (EDTA), and mixtures thereof. The chelating agent can be present individually or in the aggregate, in a concentration from about 0.01 mg/ml to about 50 mg/ml, for example from about 0.1 mg/ml to about 20 mg/ml. Pharmaceutical compositions comprising each one of these specific chelating agents constitute alternative embodiments of the invention.

In another embodiment of the invention, the pharmaceutical composition comprises a stabilizer. Non-limiting examples of stabilizers include one or more aggregation inhibitors, one or more oxidation inhibitors, one or more surfactants, and/or one or more protease inhibitors.

In another embodiment of the invention, the pharmaceutical composition comprises a stabilizer, wherein said stabilizer is carboxy-/hydroxycellulose and derivates thereof (such as HPC, HPC-SL, HPC-L and HPMC), cyclodextrins, 2-methylthioethanol, polyethylene glycol (such as PEG 3350), polyvinyl alcohol (PVA), polyvinyl pyrrolidone, salts (such as sodium chloride), sulphur-containing substances such as monothioglycerol), or thioglycolic acid. The stabilizer can be present individually or in the aggregate, in a concentration from about 0.01 mg/ml to about 50 mg/ml, for example from about 0.1 mg/ml to about 20 mg/ml. Pharmaceutical compositions comprising each one of these specific stabilizers constitute alternative embodiments of the invention.

In further embodiments of the invention, the pharmaceutical composition comprises one or more surfactants, preferably a surfactant, at least one surfactant, or two different surfactants. The term "surfactant" refers to any molecules or ions that are comprised of a water-soluble (hydrophilic) part, and a fat-soluble (lipophilic) part. The surfactant can, for example, be selected from the group consisting of anionic surfactants, cationic surfactants, nonionic surfactants, and/or zwitterionic surfactants. The surfactant can be present individually or in the aggregate, in a concentration from about 0.1 mg/ml to about 20 mg/ml. Pharmaceutical compositions comprising each one of these specific surfactants constitute alternative embodiments of the invention.

In a further embodiment of the invention, the pharmaceutical composition comprises one or more protease inhibitors, such as, e.g., EDTA, and/or benzamidine hydrochloric acid (HCl). The protease inhibitor can be present individually or in the aggregate, in a concentration from about 0.1 mg/ml to about 20 mg/ml. Pharmaceutical compositions comprising each one of these specific protease inhibitors constitute alternative embodiments of the invention.

In another general aspect, the invention relates to a method of producing a pharmaceutical composition comprising a monoclonal antibody or antigen-binding fragment thereof of the invention, comprising combining a monoclonal antibody or antigen-binding fragment thereof with a pharmaceutically acceptable carrier to obtain the pharmaceutical composition.

Methods of Use

In another general aspect, the invention relates to a method of targeting CLDN18.2 on a cancer cell surface in a subject to achieve cell killing, the method comprising administering to the subject an isolated monoclonal antibody or antigen binding fragment thereof that specifically binds CLDN18.2 or a pharmaceutical composition comprising the isolated monoclonal antibody or antigen binding fragment thereof of the invention. Binding of the CLDN18.2 monoclonal antibody or antigen-binding fragment to CLDN18.2 can mediate complement-dependent cytotoxicity (CDC), antibody-dependent phagocytosis (ADPC), and/or antibody-dependent cellular cytotoxicity (ADCC) or other effects that result in the death of the targeted cancer cell. The monoclonal antibody or antigen binding fragment thereof can, for example, serve to recruit conjugated drugs, and/or can form a bispecific antibody with another monoclonal antibody to mediate the death of the targeted cancer cell.

The functional activity of antibodies and antigen-binding fragments thereof that bind CLDN18.2 can be characterized by methods known in the art and as described herein. Methods for characterizing antibodies and antigen-binding fragments thereof that bind CLDN18.2 include, but are not limited to, affinity and specificity assays including Biacore, ELISA, and OctetRed analysis, and detection of the binding of antibodies and antigen-binding fragments to CLDN18.2 on cells (either cells transfected with CLDN18.2 or cells that naturally express CLDN18.2) by FACS. According to particular embodiments, the methods for characterizing antibodies and antigen-binding fragments thereof that bind CLDN18.2 include those described below.

In another general aspect, the invention relates to a method of treating a cancer in a subject in need thereof, comprising administering to the subject an isolated monoclonal antibody or antigen binding fragment thereof that specifically binds CLDN18.2 or a pharmaceutical composition of the invention. The cancer can, for example, be selected from but not limited to, a lung cancer, a gastric cancer, an esophageal cancer, a bile duct cancer, a cholangiocarcinoma, a colon cancer, a hepatocellular carcinoma, a renal cell carcinoma, a bladder urothelial carcinoma, a metastatic melanoma, a breast cancer, an ovarian cancer, a cervical cancer, a head and neck cancer, a pancreatic cancer, a glioma, a glioblastoma, and other solid tumors, and a non-Hodgkin's lymphoma (NHL), an acute lymphocytic leukemia (ALL), a chronic lymphocytic leukemia (CLL), a chronic myelogenous leukemia (CML), a multiple myeloma (MM), an acute myeloid leukemia (AML), and other liquid tumors.

In another general aspect, the invention relates to a method of treating an inflammatory disease in a subject in need thereof, comprising administering to the subject an isolated monoclonal antibody or antigen binding fragment thereof that specifically binds CLDN18.2 or a pharmaceutical composition of the invention.

According to embodiments of the invention, the pharmaceutical composition comprises a therapeutically effective amount of an anti-CLDN18.2 antibody or antigen-binding fragment thereof. As used herein, the term "therapeutically effective amount" refers to an amount of an active ingredient or component that elicits the desired biological or medicinal response in a subject. A therapeutically effective amount can be determined empirically and in a routine manner, in relation to the stated purpose.

As used herein with reference to anti-CLDN18.2 antibodies or antigen-binding fragments thereof, a therapeutically effective amount means an amount of the anti-CLDN18.2 antibody or antigen-binding fragment thereof that modulates an immune response in a subject in need thereof. Also, as used herein with reference to anti-CLDN18.2 antibodies or antigen-binding fragments thereof, a therapeutically effective amount means an amount of the anti-CLDN18.2 antibody or antigen-binding fragment thereof that results in treatment of a disease, disorder, or condition; prevents or slows the progression of the disease, disorder, or condition; or reduces or completely alleviates symptoms associated with the disease, disorder, or condition.

According to particular embodiments, the disease, disorder or condition to be treated is cancer, preferably a cancer selected from the group consisting of a lung cancer, a gastric cancer, an esophageal cancer, a bile duct cancer, a cholangiocarcinoma, a colon cancer, a hepatocellular carcinoma, a renal cell carcinoma, a bladder urothelial carcinoma, a metastatic melanoma, a breast cancer, an ovarian cancer, a cervical cancer, a head and neck cancer, a pancreatic cancer, a glioma, a glioblastoma, and other solid tumors, and a non-Hodgkin's lymphoma (NHL), an acute lymphocytic leukemia (ALL), a chronic lymphocytic leukemia (CLL), a chronic myelogenous leukemia (CML), a multiple myeloma (MM), an acute myeloid leukemia (AML), and other liquid tumors. According to other particular embodiments, the disease, disorder or condition to be treated is an inflammatory disease.

According to particular embodiments, a therapeutically effective amount refers to the amount of therapy which is sufficient to achieve one, two, three, four, or more of the following effects: (i) reduce or ameliorate the severity of the disease, disorder or condition to be treated or a symptom associated therewith; (ii) reduce the duration of the disease, disorder or condition to be treated, or a symptom associated therewith; (iii) prevent the progression of the disease, disorder or condition to be treated, or a symptom associated therewith; (iv) cause regression of the disease, disorder or condition to be treated, or a symptom associated therewith; (v) prevent the development or onset of the disease, disorder or condition to be treated, or a symptom associated therewith; (vi) prevent the recurrence of the disease, disorder or condition to be treated, or a symptom associated therewith; (vii) reduce hospitalization of a subject having the disease, disorder or condition to be treated, or a symptom associated therewith; (viii) reduce hospitalization length of a subject having the disease, disorder or condition to be treated, or a symptom associated therewith; (ix) increase the survival of a subject with the disease, disorder or condition to be treated, or a symptom associated therewith; (xi) inhibit or reduce the disease, disorder or condition to be treated, or a symptom associated therewith in a subject; and/or (xii) enhance or improve the prophylactic or therapeutic effect(s) of another therapy.

The therapeutically effective amount or dosage can vary according to various factors, such as the disease, disorder or condition to be treated, the means of administration, the target site, the physiological state of the subject (including, e.g., age, body weight, health), whether the subject is a human or an animal, other medications administered, and whether the treatment is prophylactic or therapeutic. Treatment dosages are optimally titrated to optimize safety and efficacy.

According to particular embodiments, the compositions described herein are formulated to be suitable for the intended route of administration to a subject. For example, the compositions described herein can be formulated to be suitable for intravenous, subcutaneous, or intramuscular administration.

As used herein, the terms "treat," "treating," and "treatment" are all intended to refer to an amelioration or reversal of at least one measurable physical parameter related to a cancer and/or an inflammatory disease, disorder or condition, which is not necessarily discernible in the subject, but can be discernible in the subject. The terms "treat," "treating," and "treatment," can also refer to causing regression, preventing the progression, or at least slowing down the progression of the disease, disorder, or condition. In a particular embodiment, "treat," "treating," and "treatment" refer to an alleviation, prevention of the development or onset, or reduction in the duration of one or more symptoms associated with the disease, disorder, or condition, such as a tumor or more preferably a cancer. In a particular embodiment, "treat," "treating," and "treatment" refer to prevention of the recurrence of the disease, disorder, or condition. In a particular embodiment, "treat," "treating," and "treatment" refer to an increase in the survival of a subject having the disease, disorder, or condition. In a particular embodiment, "treat," "treating," and "treatment" refer to elimination of the disease, disorder, or condition in the subject.

According to particular embodiments, provided are compositions used in the treatment of a cancer and/or an inflammatory disease, disorder or condition. For cancer therapy, the provided compositions can be used in combination with another treatment including, but not limited to, a chemotherapy, an anti-CD20 mAb, an anti-TIM-3 mAb, an anti-LAG-3 mAb, an anti-EGFR mAb, an anti-HER-2 mAb, an anti-CD19 mAb, an anti-CD33 mAb, an anti-CD47 mAb, an anti-CD73 mAb, an anti-DLL-3 mAb, an anti-apelin mAb, an anti-TIP-1 mAb, an anti-FOLR1 mAb, an anti-CTLA-4 mAb, an anti-PD-L1 mAb, an anti-PD-1 mAb, other immuno-oncology drugs, an antiangiogenic agent, a radiation therapy, an antibody-drug conjugate (ADC), a targeted therapy, or other anticancer drugs. Anti-CLDN18.2 antibodies can be used to construct bispecific antibodies with partner mAbs against PD-1, PD-L1, LAG3, TIM-3, CTLA-4, EGFR, HER-2, CD19, CD20, CD33, CD73, CD47, CD3, apelin, DLL-3, TIP-1, folate receptor alpha (FOLR1), and/or other tumor surface antigens to treat cancers/tumors that express both CLDN18.2 and the specific tumor associated antigen.

As used herein, the term "in combination," in the context of the administration of two or more therapies to a subject, refers to the use of more than one therapy. The use of the term "in combination" does not restrict the order in which therapies are administered to a subject. For example, a first therapy (e.g., a composition described herein) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

In another general aspect, the invention relates to a method of determining a level of CLDN18.2 in a subject. The methods comprise (a) obtaining a sample from the subject; (b) contacting the sample with a monoclonal antibody or antigen-binding fragment thereof of the invention; and (c) determining a level of CLDN18.2 in the subject.

As used herein, "sample" refers to a biological sample isolated from a subject and can include, but is not limited to, whole blood, serum, plasma, blood cells, endothelial cells, tissue biopsies (e.g., a cancer tissue), lymphatic fluid, ascites fluid, interstitial fluid, bone marrow, cerebrospinal fluid, saliva, mucous, sputum, sweat, urine, or any other secretion, excretion, or other bodily fluids. A "blood sample" refers to whole blood or any fraction thereof, including blood cells, serum, and plasma.

In certain embodiments, the level of CLDN18.2 in the subject can be determined utilizing assays selected from, but not limited to, a Western blot assay, immunohistochemistry (IHC) and an ELISA assay. Relative protein levels can be determined by utilizing Western blot analysis and IHC, and absolute protein levels can be determined by utilizing an ELISA assay. When determining the relative levels of CLDN18.2, the levels of CLDN18.2 can be determined between at least two samples, e.g., between samples from the same subject at different time points, between samples from different tissues in the same subject, and/or between samples from different subjects. Alternatively, when determining absolute levels of CLDN18.2, such as by an ELISA assay, the absolute level of CLDN18.2 in the sample can be determined by creating a standard for the ELISA assay prior to testing the sample. A person skilled in the art would understand which analytical techniques to utilize to determine the level of CLDN18.2 in a sample from the subject utilizing the antibodies or antigen-binding fragments thereof of the invention.

Utilizing methods of determining a level of CLDN18.2 in a sample from a subject can lead to the diagnosis of abnormal (elevated, reduced, or insufficient) CLDN18.2 levels in a disease and making appropriate therapeutic decisions. Such a disease can be selected from, but not limited to, a cancer and an inflammatory disease. Additionally, by monitoring the levels of CLDN18.2 in a subject, the risk of developing a disease as indicated above can be determined based on the knowledge of the level of CLDN18.2 in a particular disease and/or during the progression of the particular disease.

EMBODIMENTS

The invention provides also the following non-limiting embodiments.

Embodiment 1 is an isolated monoclonal antibody or antigen-binding fragment thereof comprising a heavy chain complementarity determining region 1 (HCDR1), HCDR2, HCDR3, a light chain complementarity determining region 1 (LCDR1), LCDR2, and LCDR3, having the polypeptide sequences of
 (1) SEQ ID NOs: 33, 34, 35, 63, 64 and 65, respectively;
 (2) SEQ ID NOs: 21, 22, 23, 51, 52 and 53, respectively;
 (3) SEQ ID NOs: 24, 25, 26, 54, 55 and 56, respectively;
 (4) SEQ ID NOs: 27, 28, 29, 57, 58 and 59, respectively;
 (5) SEQ ID NOs: 30, 31, 32, 60, 61 and 62, respectively;
 (6) SEQ ID NOs: 36, 37, 38, 66, 67 and 68, respectively;
 (7) SEQ ID NOs: 39, 40, 41, 69, 70 and 71, respectively;
 (8) SEQ ID NOs: 42, 43, 44, 72, 73 and 74, respectively;
 (9) SEQ ID NOs: 45, 46, 47, 75, 76 and 77, respectively; or
 (10) SEQ ID NOs: 48, 49, 50, 78, 79 and 80, respectively;
wherein the antibody or antigen-binding fragment thereof specifically binds claudin 18.2 (CLDN18.2), preferably specifically binds human CLDN18.2.

Embodiment 2 is an isolated monoclonal antibody or antigen-binding fragment thereof comprising a heavy chain complementarity determining region 1 (HCDR1), HCDR2, HCDR3, a light chain complementarity determining region 1 (LCDR1), LCDR2, and LCDR3, having the polypeptide sequences of
 (1) SEQ ID NOs: 93, 94, 95, 123, 124 and 125, respectively;

(2) SEQ ID NOs: 81, 82, 83, 111, 112 and 113, respectively;
(3) SEQ ID NOs: 84, 85, 86, 114, 115 and 116, respectively;
(4) SEQ ID NOs: 87, 88, 89, 117, 118 and 119, respectively;
(5) SEQ ID NOs: 90, 91, 92, 120, 121 and 122, respectively;
(6) SEQ ID NOs: 96, 97, 98, 126, 127 and 128, respectively;
(7) SEQ ID NOs: 99, 100, 101, 129, 130 and 131, respectively;
(8) SEQ ID NOs: 102, 103, 104, 132, 133 and 134, respectively;
(9) SEQ ID NOs: 105, 106, 107, 135, 136 and 137, respectively; or
(10) SEQ ID NOs: 108, 109, 110, 138, 139 and 140, respectively;

wherein the antibody or antigen-binding fragment thereof specifically binds claudin 18.2 (CLDN18.2), preferably specifically binds human CLDN18.2.

Embodiment 3 is the isolated monoclonal antibody or antigen-binding fragment of embodiment 1 or 2, comprising a heavy chain variable region having a polypeptide sequence at least 95% identical to SEQ ID NO: 9, 1, 3, 5, 7, 11, 13, 15, 17 or 19, or a light chain variable region having a polypeptide sequence at least 95% identical to SEQ ID NO: 10, 2, 4, 6, 8, 12, 14, 16, 18 or 20.

Embodiment 4 is the isolated monoclonal antibody or antigen-binding fragment of embodiment 1 or 2, comprising
(a) a heavy chain variable region having the polypeptide sequence of SEQ ID NO:9, and a light chain variable region having the polypeptide sequence of SEQ ID NO:10;
(b) a heavy chain variable region having the polypeptide sequence of SEQ ID NO:1, and a light chain variable region having the polypeptide sequence of SEQ ID NO:2;
(c) a heavy chain variable region having the polypeptide sequence of SEQ ID NO:3, and a light chain variable region having the polypeptide sequence of SEQ ID NO:4;
(d) a heavy chain variable region having the polypeptide sequence of SEQ ID NO:5, and a light chain variable region having the polypeptide sequence of SEQ ID NO:6;
(e) a heavy chain variable region having the polypeptide sequence of SEQ ID NO:7, and a light chain variable region having the polypeptide sequence of SEQ ID NO:8;
(f) a heavy chain variable region having the polypeptide sequence of SEQ ID NO:11, and a light chain variable region having the polypeptide sequence of SEQ ID NO:12;
(g) a heavy chain variable region having the polypeptide sequence of SEQ ID NO:13, and a light chain variable region having the polypeptide sequence of SEQ ID NO:14;
(h) a heavy chain variable region having the polypeptide sequence of SEQ ID NO:15, and a light chain variable region having the polypeptide sequence of SEQ ID NO:16;
(i) a heavy chain variable region having the polypeptide sequence of SEQ ID NO:17, and a light chain variable region having the polypeptide sequence of SEQ ID NO:18;
(j) a heavy chain variable region having the polypeptide sequence of SEQ ID NO:19, and a light chain variable region having the polypeptide sequence of SEQ ID NO:20.

Embodiment 5 is the isolated monoclonal antibody or antigen-binding fragment thereof of any one of embodiments 1-4, wherein the monoclonal antibody or antigen-binding fragment thereof is capable of inducing effector-mediated tumor cell lysis.

Embodiment 6 is the isolated monoclonal antibody or antigen-binding fragment of any one of embodiments 1-5, wherein the antibody or antigen-binding fragment thereof is chimeric.

Embodiment 7 is the isolated monoclonal antibody or antigen-binding fragment of any one of embodiments 1-6, wherein the antibody or antigen-binding fragment thereof is human or humanized.

Embodiment 8 is the isolated monoclonal antibody or antigen-binding fragment of embodiment 7, wherein the isolated humanized antibody or antigen-binding fragment thereof comprises:
a. a heavy chain variable region having the polypeptide sequence of SEQ ID NO:142, and a light chain variable region having the polypeptide sequence of SEQ ID NO:144;
b. a heavy chain variable region having the polypeptide sequence of SEQ ID NO:142, and a light chain variable region having the polypeptide sequence of SEQ ID NO:145;
c. a heavy chain variable region having the polypeptide sequence of SEQ ID NO:143, and a light chain variable region having the polypeptide sequence of SEQ ID NO:144;
d. a heavy chain variable region having the polypeptide sequence of SEQ ID NO:143, and a light chain variable region having the polypeptide sequence of SEQ ID NO:145;
e. a heavy chain variable region having the polypeptide sequence of SEQ ID NO:146, and a light chain variable region having the polypeptide sequence of SEQ ID NO:148;
f. a heavy chain variable region having the polypeptide sequence of SEQ ID NO:146, and a light chain variable region having the polypeptide sequence of SEQ ID NO:149;
g. a heavy chain variable region having the polypeptide sequence of SEQ ID NO:146, and a light chain variable region having the polypeptide sequence of SEQ ID NO:150;
h. a heavy chain variable region having the polypeptide sequence of SEQ ID NO:147, and a light chain variable region having the polypeptide sequence of SEQ ID NO:148;
i. a heavy chain variable region having the polypeptide sequence of SEQ ID NO:147, and a light chain variable region having the polypeptide sequence of SEQ ID NO:149;
j. a heavy chain variable region having the polypeptide sequence of SEQ ID NO:147, and a light chain variable region having the polypeptide sequence of SEQ ID NO:150;
k. a heavy chain variable region having the polypeptide sequence of SEQ ID NO:151, and a light chain variable region having the polypeptide sequence of SEQ ID NO:153;

l. a heavy chain variable region having the polypeptide sequence of SEQ ID NO:152, and a light chain variable region having the polypeptide sequence of SEQ ID NO:153;

m. a heavy chain variable region having the polypeptide sequence of SEQ ID NO:154, and a light chain variable region having the polypeptide sequence of SEQ ID NO:157;

n. a heavy chain variable region having the polypeptide sequence of SEQ ID NO:155, and a light chain variable region having the polypeptide sequence of SEQ ID NO:157;

o. a heavy chain variable region having the polypeptide sequence of SEQ ID NO:156, and a light chain variable region having the polypeptide sequence of SEQ ID NO:158;

p. a heavy chain variable region having the polypeptide sequence of SEQ ID NO:159, and a light chain variable region having the polypeptide sequence of SEQ ID NO:163;

q. a heavy chain variable region having the polypeptide sequence of SEQ ID NO:159, and a light chain variable region having the polypeptide sequence of SEQ ID NO:164;

r. a heavy chain variable region having the polypeptide sequence of SEQ ID NO:160, and a light chain variable region having the polypeptide sequence of SEQ ID NO:163;

s. a heavy chain variable region having the polypeptide sequence of SEQ ID NO:160, and a light chain variable region having the polypeptide sequence of SEQ ID NO:164;

t. a heavy chain variable region having the polypeptide sequence of SEQ ID NO:161, and a light chain variable region having the polypeptide sequence of SEQ ID NO:165; or u. a heavy chain variable region having the polypeptide sequence of SEQ ID NO:162, and a light chain variable region having the polypeptide sequence of SEQ ID NO:165.

Embodiment 9 is the isolated monoclonal antibody or antigen-binding fragment of any one of embodiments 1-8, wherein the isolated humanized antibody or antigen-binding fragment thereof is capable of inducing effector-mediated tumor cell lysis through antibody-dependent cellular cytotoxicity (ADCC), antibody-dependent phagocytosis (ADPC), and/or complement-dependent cytotoxicity (CDC), and/or mediating the recruitment of conjugated drugs, and/or forming a bispecific antibody with another mAb or antigen-binding fragment thereof with cancer-killing effect.

Embodiment 10 is an isolated nucleic acid encoding the monoclonal antibody or antigen-binding fragment of any one of embodiments 1-9.

Embodiment 11 is a vector comprising the isolated nucleic acid of embodiment 10.

Embodiment 12 is a host cell comprising the vector of embodiment 11.

Embodiment 13 is a pharmaceutical composition, comprising the isolated monoclonal antibody or antigen-binding fragment of any one of embodiments 1-9 and a pharmaceutically acceptable carrier.

Embodiment 14 is a method of targeting CLDN18.2 on a cancer cell surface in a subject in need thereof, comprising administering to the subject the pharmaceutical composition of embodiment 13.

Embodiment 15 is a method of treating cancer in a subject in need thereof, comprising administering to the subject the pharmaceutical composition of embodiment 13.

Embodiment 16 is the method of embodiment 15, wherein the cancer is selected from the group consisting of a lung cancer, a gastric cancer, an esophageal cancer, a bile duct cancer, a cholangiocarcinoma, a colon cancer, a hepatocellular carcinoma, a renal cell carcinoma, a bladder urothelial carcinoma, a metastatic melanoma, a breast cancer, an ovarian cancer, a cervical cancer, a head and neck cancer, a pancreatic cancer, a glioma, a glioblastoma, and other solid tumors, and a hon-Hodgkin's lymphoma (NHL), an acute lymphocytic leukemia (ALL), a chronic lymphocytic leukemia (CLL), a chronic myelogenous leukemia (CML), a multiple myeloma (MM), an acute myeloid leukemia (AML), and other liquid tumors.

Embodiment 17 is a method of treating an inflammatory disease in a subject in need thereof, comprising administering to the subject the pharmaceutical composition of embodiment 13.

Embodiment 18 is a method of producing the monoclonal antibody or antigen-binding fragment of any one of embodiments 1-9, comprising culturing a cell comprising a nucleic acid encoding the monoclonal antibody or antigen-binding fragment thereof under conditions to produce the monoclonal antibody or antigen-binding fragment thereof and recovering the antibody or antigen-binding fragment thereof from the cell or culture.

Embodiment 19 is a method of producing a pharmaceutical composition comprising the monoclonal antibody or antigen-binding fragment thereof of any one of embodiments 1-9, comprising combining the monoclonal antibody or antigen-binding fragment thereof with a pharmaceutically acceptable carrier to obtain the pharmaceutical composition.

Embodiment 20 is a method of determining a level of CLDN18.2 in a subject, the method comprising:
  a. obtaining a sample from the subject;
  b. contacting the sample with the isolated monoclonal antibody or antigen-binding fragment thereof of any one of embodiments 1-9; and
  c. determining a level of CLDN18.2 in the subject.

Embodiment 21 is the method of embodiment 20, wherein the sample is a tissue sample.

Embodiment 22 is the method of embodiment 21, wherein the tissue sample is a cancer tissue sample.

Embodiment 23 is the method of embodiment 20, wherein the sample is a blood sample.

EXAMPLES

Example 1: Identification of Anti-CLDN18.2 Monoclonal Antibodies

Mice were immunized with cells expressing exogenous human CLDN18.2 and plasma titer was determined by fluorescence-activated cell sorting (FACS). Splenocytes were harvested and fused with a myeloma cell line to produce hybridomas. Hybridomas were plated into 384 well plates and supernatants from individual wells were screened by FACS using HEK293 cells expressing CLDN18.2. Positive clones were counter-screened against human CLDN18.1 expressed on HEK293 cells by FACS. Top positive clones were isolated and sequenced.

Sequences of heavy and light chain variable regions for anti-CLDN18.2 monoclonal antibodies are provided in Tables 1 and 2, and the CDR regions for the anti-CLDN18.2 monoclonal antibodies are provided in Tables 3-6.

TABLE 1

Sequences of heavy chain variable regions for anti-CLDN18.2 mAbs

| mAb clones | VH | SEQ ID NO: |
|---|---|---|
| 2-C3 | EVQLVESGGDLVKPGGSLKLSCAASGFTFSSYGMSWVRQT PDKRLEWVATISGGGSYTYYLDSVKGRFTISRDIAKNTLY LQMSSLKSEDTAMYFCARQSRGNAMDYWGQGTSVTVSS | 1 |
| 2-P8 | EVQLQQSGPELVKPGASVKMSCKASGYSFTGYNMHWVKQS HGKSLEWIGYIDPYNGVTNYNQKFKGKATLTVDKSSSTAY VQLNSLTSEDSAVYYCARWGGNYVDYWGQGTTLKVSS | 3 |
| 3-E21 | EVQLVESGGALVKPGGSLKLSCAASGFTFSKYAMSWVRQT PEKRLEWVAFISNGGSYTYCLDSVKGRFTISRDNAKNTLY LQMSSLRSEDTALYYCARHDKGNALDYWGQGNSVTVSS | 5 |
| 3-P21 | EIQLQQSGAELVKPGASVKISCKASGYSFTGYNMKWVKQS HGKSLEWIGNINPYFGSTNYNQKFKGKATLTVDKSSSTAY MQLNSLTSEDSAVYYCARGAYYGNAMDYWGQGTSVTVSS | 7 |
| 5-E22 | KVQLQQSGPDLVEPGASVKISCKASGYTITDNYMHWVKQK PGQGLEWIGEIYPGSGNTYYNERFKGKATLTADKSSSTAY MQLSSLTSEDSAVYFCARGFPYYAMDYWGPGTSVTVSS | 9 |
| 6-J11 | DVQLVESGGGLVQPGGSRKLSCAASGFIFSSFGMHWVRQA PEKGLEWVAYISSGRSTMYYADTVKGRFTISRDNPKNTLF LQMTSLRSEDTAMYYCARGGFYGNSLDYWGQGTSVTVSS | 11 |
| 8-G12 | QVQLQQSGPELVKPGASVKISCKASGYAFSDYWMNWVKQR PGKGLEWIGQIYPGYGDTKYNENFKGTATLTADKSSSTAY MQLSSLTSEDSAVYFCARWGYYGNAMDYWGQGTSVTVSS | 13 |
| 10-J10 | QVQLQQPGAELVKPGASVKLSCKASGYTFTRYRMNWVKQR PGQGLEWIGNIDPSDSETHYNQKFKDKATLTVDKSSSTAY MQLSSLTSEDSAVFYCARLNYGNCFDYWGQGTTLTVSS | 15 |
| 10-K2 | EVQLQQSGPELVKPGASVKMSCKASGYAFTSYVMHWVKQK PGQGLEWIGYINPYSDGTRYNEKFKGKATLTSDKSSSTAY MELSSLTSEDSAVYYCTRIYYGNAMDYWGQGTSVTVSS | 17 |
| 15-D6 | QVQLQQPGADLVKPGASVKLSCKASGYTFTSYWINWVKQR PGQGLEWIGNIYPGRSSTNYNEKFKSKATLTVDTSSSTAY MQLSSLASDDSAVYYCSRLSRGNAMDYWGQGTSVTVSS | 19 |

VH: heavy chain variable region

TABLE 2

Sequences of light chain variable regions for anti-CLDN18.2 mAbs

| mAb clones | VL | SEQ ID NO: |
|---|---|---|
| 2-C3 | DIVMTQSPSSLTVTAGEKVTMSCKSSQSLLNSGNQKNYLT WYQQKPGQPPKLLIYWASTRESGVPDRFTGSGSGTDFTLT ISSVQAEDLAVYYCQNDYSYPLTFGAGTKLELK | 2 |
| 2-P8 | DIKMTQSPSSMYASLGERVTITCKASQDINRYLSWFQQKP GKSPKTLIYRANRLVDGVPSRFSGSFSGQDYSLTISSLEY EDMGIYYCLQYDEFPLTFGAGTKLELK | 4 |
| 3-E21 | DIVMTQSPSSLTVTAGEKVTMSCKSSQSLLNSGNQKNYLT WYQQKPGQPPKLLIYWASTRESGVPDRFTGSGSGTDFTLT ISSVQAEDLSVYYCQNDYFYPLTFGAGTKLELK | 6 |
| 3-P21 | DIVMTQSPSSLTVTAGGKVTMSCKSSQSLLNSGNQKNYLT WYQQKPGQPPKLLIYWASTRESGVPDRFSGSGSGTDFTLT ISSVQAEDLAVYYCQNDYFYPLTFGAGTKLELK | 8 |
| 5-E22 | DIQMNQSPSSLSASLGDTITITCHARQNINVWLSWYQQKS GNIPKLLIYKASNLHTGVPSRFSGSGSGTRFTLTISSLQP EDMATYYCQQGQNYPLTFGGGTKLEIK | 10 |

TABLE 2-continued

Sequences of light chain variable regions for anti-CLDN18.2 mAbs

| mAb clones | VL | SEQ ID NO: |
|---|---|---|
| 6-J11 | DIVMTQSPSSLTVTAGEKVTMSCKSSLSLLNSGNQKNYLT WYQQKPGQPPKLLIYWASTRESGVPDRFTGSGSGTDFTLT ISSMQAEDLAVYSCQNAYSYPLTFGAGTKLELK | 12 |
| 8-G12 | DIVMTQSPSSLTVTAGEKVTMSCKSSQSLLNSGNQKNYLT WYQQKPGQPPKLLIYWASTRESGVPDRFTGSGSGTDFTLT ISSVQTEDLAIYYCQNAYIYPLTFGAGTKLELK | 14 |
| 10-J10 | DIVMTQSPSSLTVTAGEKVTMSCKSSQTLLNSGNQKNYLT WYQQKPGQPPKLLIYWASTRESGVPDRFTGSGSGTDFTLT ISSVQAEDLAVFYCQNDYFYPFTFGSGTKLEIK | 16 |
| 10-K2 | DIVMTQSPSSLTVTAGEKVTMSCKSSQSLLNSGNQKNYLT WYQQKPGQPPKLLIYWASTRESGVPDRFTGSGSGTDFTLT ISSVQAEDLAVYYCQNDYSYPFTFGSGTKLEIK | 18 |
| 15-D6 | DIVMTQSPSSLTVTAGEKVTMSCRSSQSLLNSGNQKSYLT WYQQKPGQPPKLLIYWASTRESGVPDRFTGSGSGTDFTLT ISSVQAEDLAVYYCQNDYYYPFTFGSGTKLEIK | 20 |

VL: light chain variable region

TABLE 3

CDR regions 1-3 of heavy chain for anti-CLDN18.2 mAbs

| mAb clones | HC CDR1 | NO | HC CDR2 | NO | HC CDR3 | NO |
|---|---|---|---|---|---|---|
| 2-C3 | GFTFSSYG | 21 | ISGGGSYT | 22 | ARQSRGNAMDY | 23 |
| 2-P8 | GYSFTGYN | 24 | IDPYNGVT | 25 | ARWGGNYVDY | 26 |
| 3-E21 | GFTFSKYA | 27 | ISNGGSYT | 28 | ARHDKGNALDY | 29 |
| 3-P21 | GYSFTGYN | 30 | INPYFGST | 31 | ARGAYYGNAMDY | 32 |
| 5-E22 | GYTITDNY | 33 | IYPGSGNT | 34 | ARGFPYYAMDY | 35 |
| 6-J11 | GFIFSSFG | 36 | ISSGRSTM | 37 | ARGGFYGNSLDY | 38 |
| 8-G12 | GYAFSDYW | 39 | IYPGYGDT | 40 | ARWGYYGNAMDY | 41 |
| 10-J10 | GYTFTRYR | 42 | IDPSDSET | 43 | ARLNYGNCFDY | 44 |
| 10-K2 | GYAFTSYV | 45 | INPYSDGT | 46 | TRIYYGNAMDY | 47 |
| 15-D6 | GYTFTSYW | 48 | IYPGRSST | 49 | SRLSRGNAMDY | 50 |

HC: heavy chain; CDR: complementarity determining region; ID: SEQ ID NO
The HC CDRs for the anti-CLDN18.2 mAbs were determined utilizing the IMGT method (Lefranc, M.-P. et al., Nucleic Acids Res. 1999; 27: 209-212).

TABLE 4

CDR regions 1-3 of light chain for anti-CLDN18.2 mAbs

| mAb clones | LC CDR1 | NO | LC CDR2 | NO | LC CDR3 | NO |
|---|---|---|---|---|---|---|
| 2-C3 | QSLLNSGNQKNY | 51 | WAS | 52 | QNDYSYPLT | 53 |
| 2-P8 | QDINRY | 54 | RAN | 55 | LQYDEFPLT | 56 |
| 3-E21 | QSLLNSGNQKNY | 57 | WAS | 58 | QNDYFYPLT | 59 |
| 3-P21 | QSLLNSGNQKNY | 60 | WAS | 61 | QNDYFYPLT | 62 |

TABLE 4-continued

CDR regions 1-3 of light chain for anti-CLDN18.2 mAbs

| mAb clones | LC CDR1 | NO | LC CDR2 | NO | LC CDR3 | NO |
|---|---|---|---|---|---|---|
| 5-E22 | QNINVW | 63 | KAS | 64 | QQGQNYPLT | 65 |
| 6-J11 | LSLLNSGNQKNY | 66 | WAS | 67 | QNAYSYPLT | 68 |
| 8-G12 | QSLLNSGNQKNY | 69 | WAS | 70 | QNAYIYPLT | 71 |
| 10-J10 | QTLLNSGNQKNY | 72 | WAS | 73 | QNDYFYPFT | 74 |
| 10-K2 | QSLLNSGNQKNY | 75 | WAS | 76 | QNDYSYPFT | 77 |
| 15-D6 | QSLLNSGNQKSY | 78 | WAS | 79 | QNDYYYPFT | 80 |

LC: light chain; CDR: complementarity determining region; NO: SEQ ID NO
The LC CDRs for the anti-CLDN18.2 mAbs were determined utilizing the IMGT method (Lefranc, M.-P. et al., Nucleic Acids Res. 1999; 27: 209-212).

TABLE 5

CDR regions 1-3 of heavy chain for anti-CLDN18.2 mAbs

| mAb clones | HC CDR1 | NO | HC CDR2 | NO | HC CDR3 | NO |
|---|---|---|---|---|---|---|
| 2-C3 | GFTFSSYGMS | 81 | TISGGGSYTYYLDSVKG | 82 | ARQSRGNAMDY | 83 |
| 2-P8 | GYSFTGYNMH | 84 | YIDPYNGVTNYNQKFKG | 85 | ARWGGNYVDY | 86 |
| 3-E21 | GFTFSKYAMS | 87 | FISNGGSYTYCLDSVKG | 88 | ARHDKGNALDY | 89 |
| 3-P21 | GYSFTGYNMK | 90 | NINPYFGSINYNQKFKG | 91 | ARGAYYGNAMDY | 92 |
| 5-E22 | GYTITDNYMH | 93 | EIYPGSGNTYYENRFKG | 94 | ARGFPYYAMDY | 95 |
| 6-J11 | GFIFSSFGMH | 96 | YISSGRSTMYYDATVKG | 97 | ARGGFYGNSLDY | 98 |
| 8-G12 | GYAFSDYWMN | 99 | QIYPGYGDTKYNKENFG | 100 | ARWGYYGNAMDY | 101 |
| 10-J10 | GYTFTRYRMN | 102 | NIDPSDSETHYNQKFKD | 103 | ARLNYGNCFDY | 104 |
| 10-K2 | GYAFTSYVMH | 105 | YINPYSDGTRYNEKFKG | 106 | TRIYYGNAMDY | 107 |
| 15-D6 | GYTFTSYWIN | 108 | NIYPGRSSTNYNEKFKS | 109 | SRLSRGNAMDY | 110 |

HC: heavy chain; CDR: complementarity determining region; NO: SEQ ID NO
The HC CDRs for the anti-CLDN18.2 mAbs were determined utilizing a combination of IMGT (Lefranc, M.-P. et al., Nucleic Acids Res. 1999; 27: 209-212) and Kabat (Elvin A. Kabat et al, Sequences of Proteins of Immunological Interest 5th ed. (1991)) methods.

TABLE 6

CDR regions 1-3 of light chain for anti-CLDN18.2 mAbs

| mAb clones | LC CDR1 | NO | LC CDR2 | NO | LC CDR3 | NO |
|---|---|---|---|---|---|---|
| 2-C3 | KSSQSLLNSGNQKNYLT | 111 | WASTRES | 112 | QNDYSYPLT | 113 |
| 2-P8 | KASQDINRYLS | 114 | RANRLVD | 115 | LQYDEFPLT | 116 |
| 3-E21 | KSSQSLLNSGNQKNYLT | 117 | WASTRES | 118 | QNDYFYPLT | 119 |
| 3-P21 | KSSQSLLNSGNQKNYLT | 120 | WASTRES | 121 | QNDYFYPLT | 122 |
| 5-E22 | HARQNINVWLS | 123 | KASNLHT | 124 | QQGQNYPLT | 125 |
| 6-J11 | KSSLSLLNSGNQKNYLT | 126 | WASTRES | 127 | QNAYSYPLT | 128 |
| 8-G12 | KSSQSLLNSGNQKNYLT | 129 | WASTRES | 130 | QNAYIYPLT | 131 |
| 10-J10 | KSSQTLLNSGNQKNYLT | 132 | WASTRES | 133 | QNDYFYPFT | 134 |
| 10-K2 | KSSQSLLNSGNQKNYLT | 135 | WASTRES | 136 | QNDYSYPFT | 137 |
| 15-D6 | RSSQSLLNSGNQKSYLT | 138 | WASTRES | 139 | QNDYYYPFT | 140 |

LC: light chain; CDR: complementarity determining region; NO: SEQ ID NO
The LC CDRs for the anti-CLDN18.2 mAbs were determined utilizing a combination of IMGT (Lefranc, M.-P. et al., Nucleic Acids Res. 1999; 27: 209-212) and Kabat (Elvin A. Kabat et al, Sequences of Proteins of Immunological Interest 5th ed. (1991)) methods.

Example 2: Production and Purification of mAbs from Culture Media of Transfected 293E Cells To obtain recombinant anti-CLDN18.2 chimeric mAbs, the expression vectors containing the mouse variable regions (VH and VL) fused to the constant regions of human IgG1 heavy chain and kappa light chain, respectively, were transiently transfected into 293E cells. The recombinant antibodies produced in the suspension of the 293E cells were purified using Protein A affinity chromatography.

Example 3: FACS Binding Analysis of Purified Anti-CLDN18.2 Antibodies

HEK293 cells stably transfected with full-length human CLDN18.2 were transferred to a 96-well plate. Around 50,000 cells were incubated with purified chimeric anti-CLDN18.2 mAbs (variable regions of mouse mAbs fused to the constant regions of human IgG1 heavy chain and kappa light chain, respectively) at various concentrations for 15 minutes on ice. In some instances, 100,000 cells per well were used. Cells were then centrifuged for 5 minutes and washed once with FACS buffer (HBSS supplemented with 0.1% BSA and 0.05% sodium azide). The cells were then incubated with FITC-conjugated goat anti-human IgG polyclonal antibodies (Thermo Fisher, Cat #: H10301) and incubated on ice for another 15 minutes. Cells were then washed with FACS buffer once and resuspended in FACS buffer. Cells were then run through the Attune NxT and the data were analyzed by the Attune NxT software. The FACS data are expressed as mean fluorescence intensity (MFI).

The binding of the chimeric anti-CLDN18.2 mAbs to HEK293 cells stably transfected with full-length human CLDN18.2 (stable cell pool) was analyzed by FACS. Results for the dose-dependent binding are provided in FIGS. 1A-1D. The binding of the chimeric anti-CLDN18.2 mAbs to HEK293 cells stably transfected with full-length human CLDN18.2 and CLDN18.1 (stable cell pools), respectively, was assessed using 10 nM mAbs using FACS. Results of the FACS binding analysis are provided in FIGS. 2A-2E. The data indicate that these mAbs specifically bind to CLDN18.2 and do not bind to CLDN18.1.

Figure 3A:
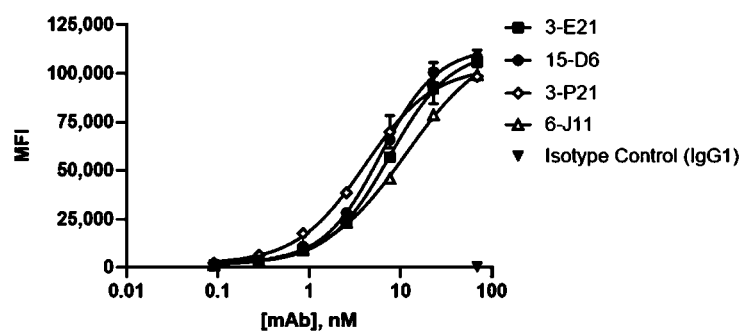
FIGS. 3A-3C show the results of dose-dependent binding of the chimeric anti-CLDN18.2 mAbs to a HEK293-CLDN18.2 stable cell line by FACS analysis.
Figure 3B:
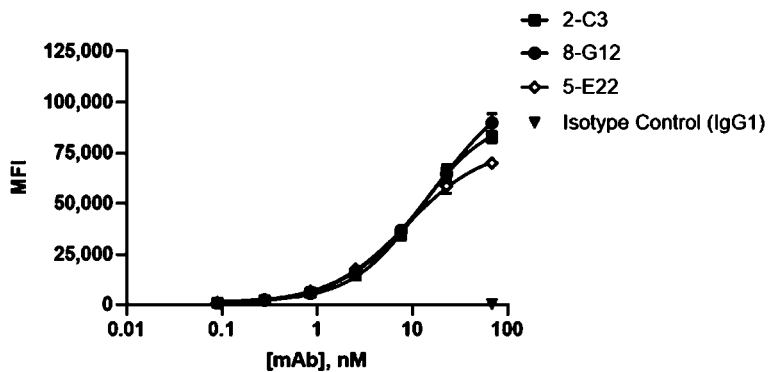
Figure 3C:
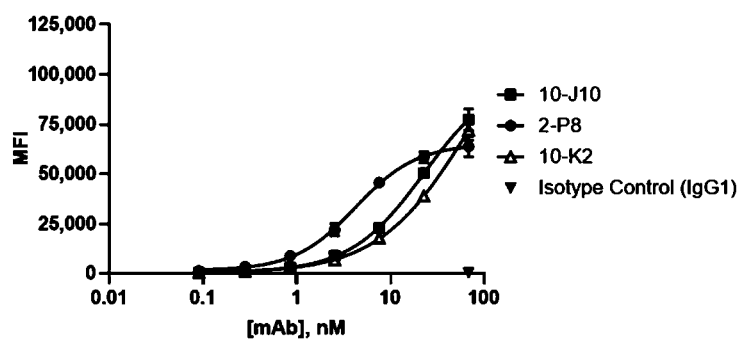
Figure 4A:
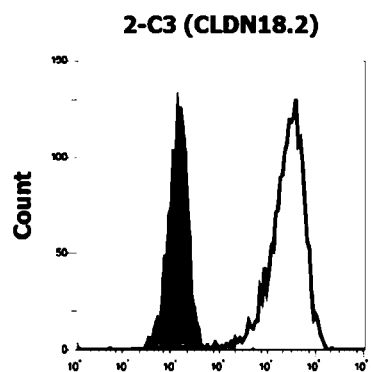
FIGS. 4A-4J show the histograms for the binding of the chimeric anti-CLDN18.2 mAbs to a HEK293-CLDN18.2 stable cell line. The shaded gray peak is representative of the treatment group incubated with only the secondary antibody and the open black peak is representative of the treatment group incubated with both primary chimeric mAb and the secondary antibody.
Figure 4B:
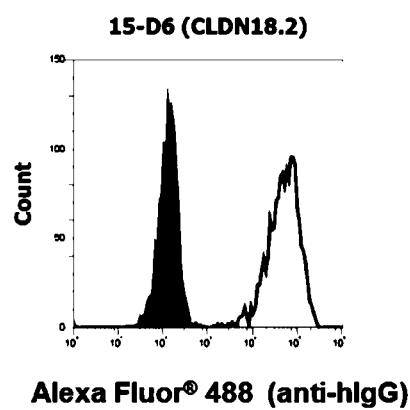
Figure 4C:
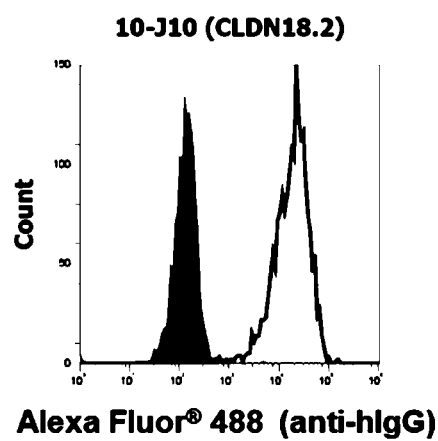
Figure 4D:
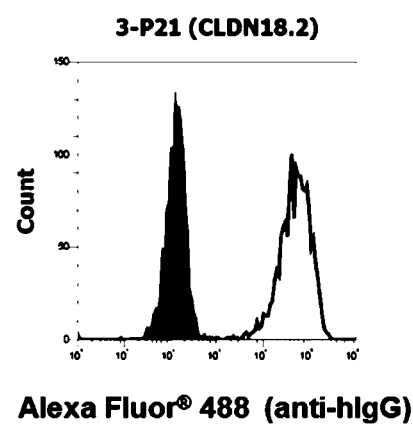
Figure 4E:
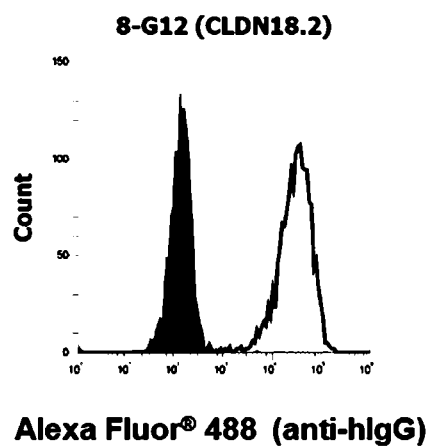
Figure 4F:
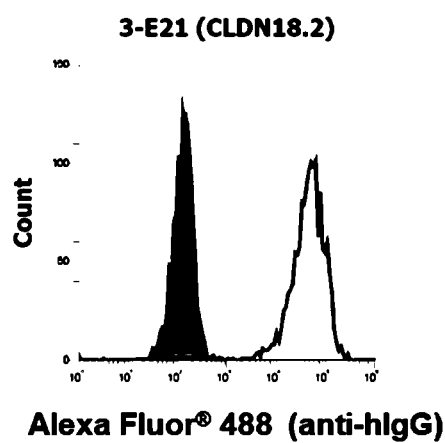
Figure 4G:
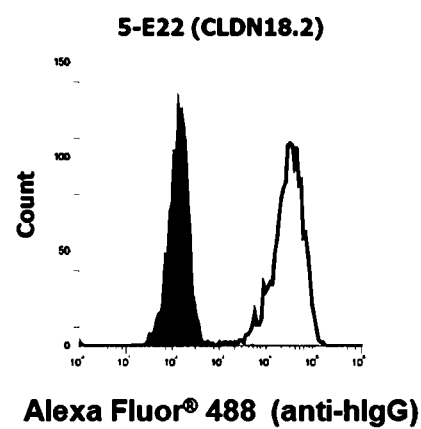
Figure 4H:
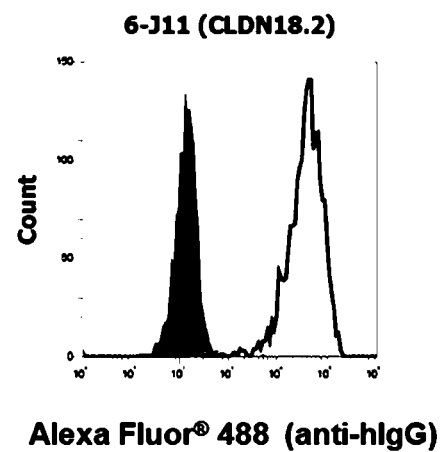
Figure 4I:
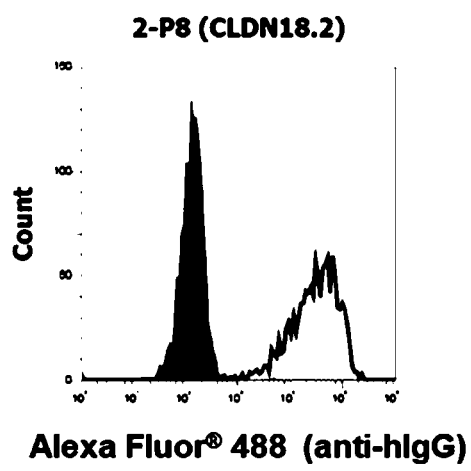
Figure 4J:
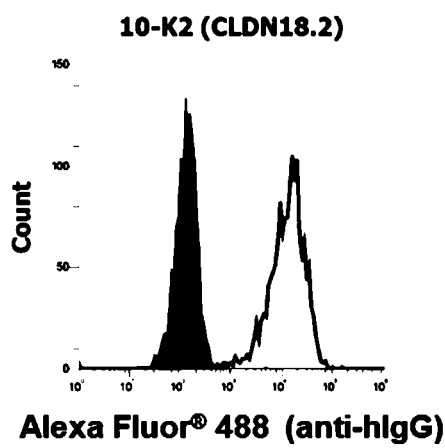
Figure 5A:
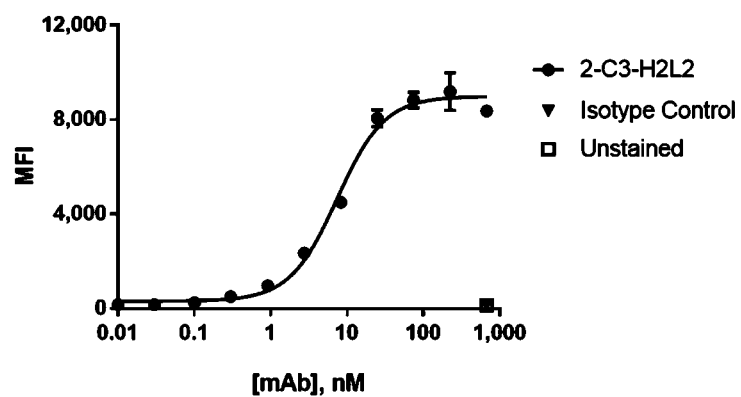
FIGS. 5A-5G show the results of dose-dependent binding of the humanized anti-CLDN18.2 mAbs to HEK293-CLDN18.2 stable pools by FACS analysis.
Figure 5B:
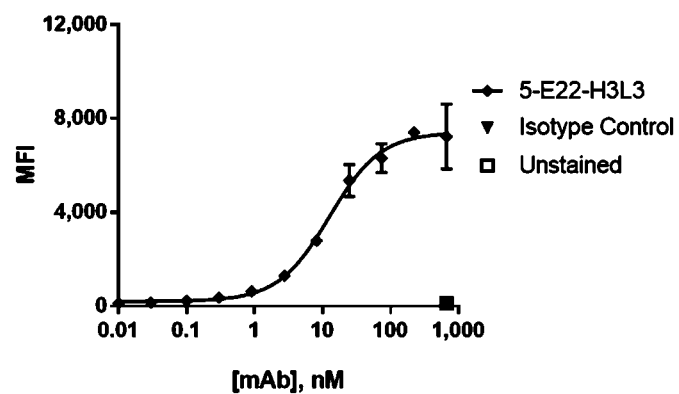
Figure 5C:
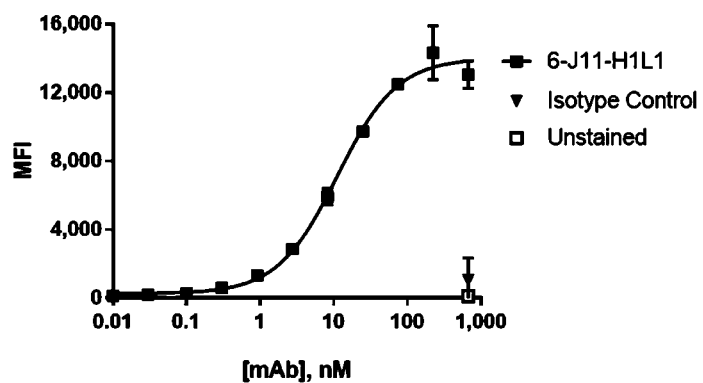
Figure 5D:
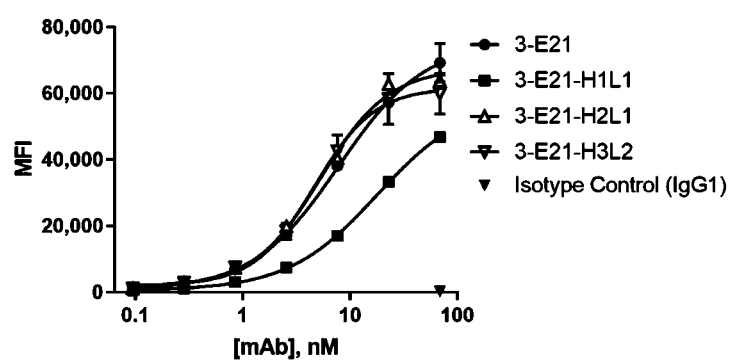
Figure 5E:
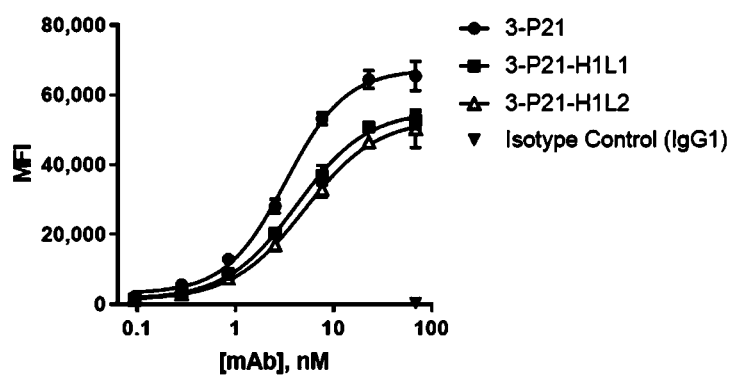
Figure 5F:
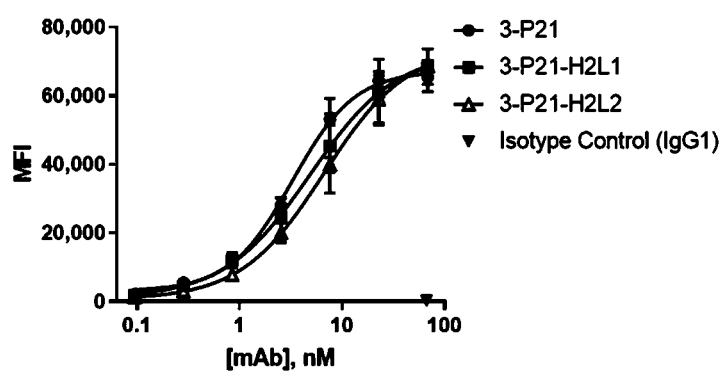
Figure 5G:
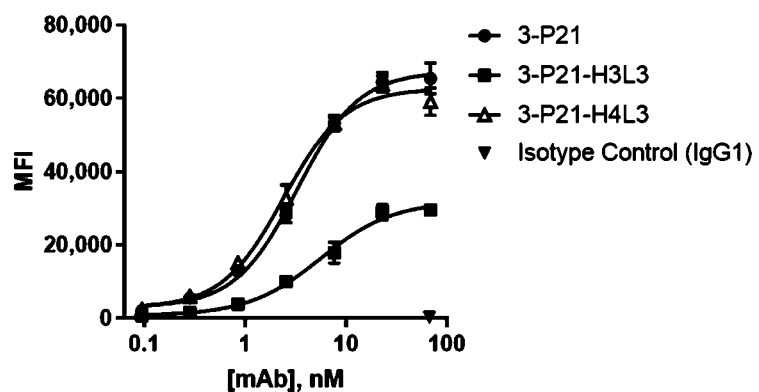
Figure 6A:
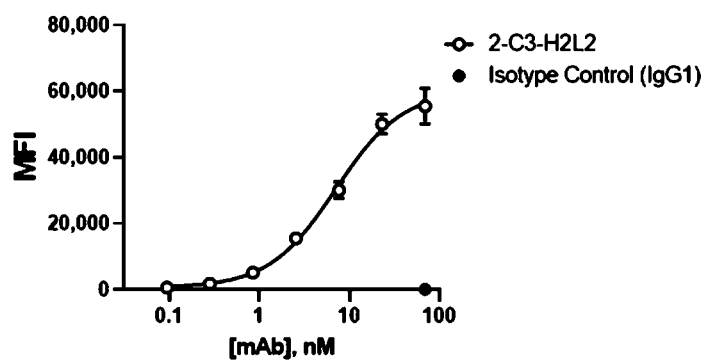
FIGS. 6A-6E show the results of dose-dependent binding of the humanized anti-CLDN18.2 mAbs to a HEK293-CLDN18.2 stable cell line by FACS analysis.
Figure 6B:
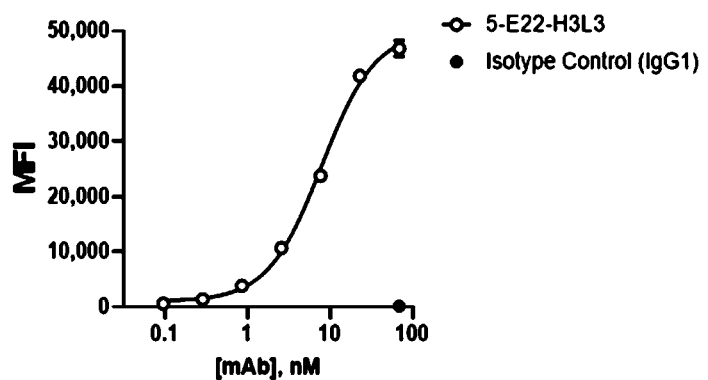
Figure 6C:
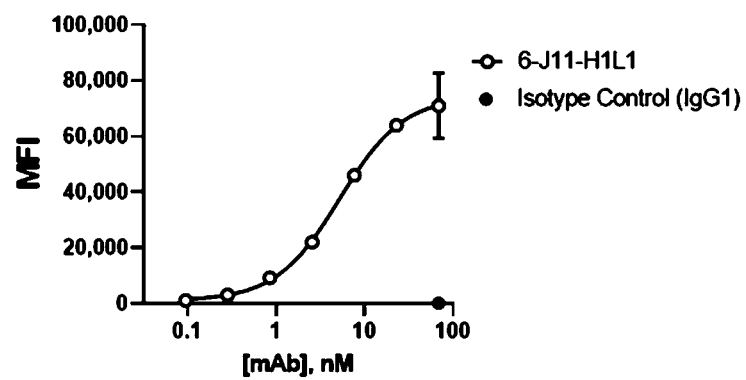
Figure 6D:
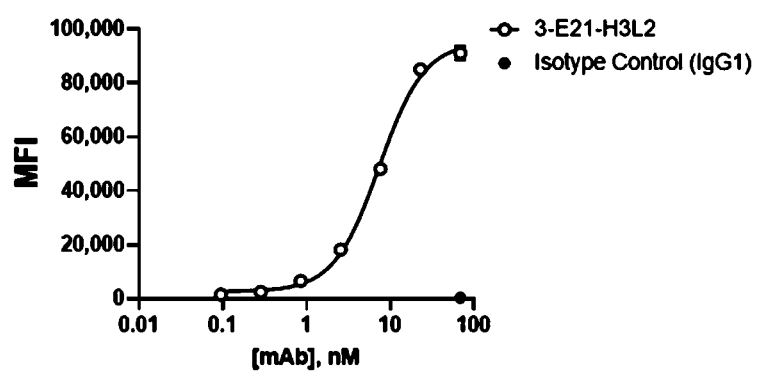
Figure 6E:
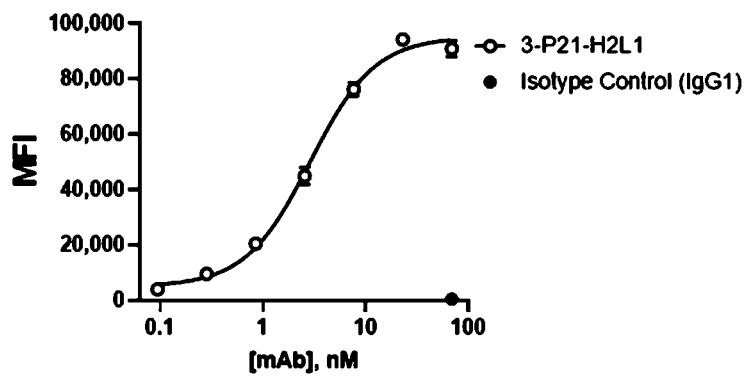

The chimeric anti-CLDN18.2 mAbs were also analyzed with a HEK293 stable cell line expressing the full-length human CLDN18.2 (HEK293-CLDN18.2) using FACS as described above except that the final detection step was carried out using F(ab')2-Goat anti-Human IgG Fc conjugated to Alexa Fluor® 488 (Invitrogen, Cat #: H10120). Results for the FACS analysis of dose-dependent binding of the chimeric anti-CLDN18.2 mAbs to the HEK293-CLDN18.2 stable cell line are provided in FIGS. 3A-3C. The histogram for the binding of each chimeric mAb at 7.6 nM to the HEK293-CLDN18.2 stable cell line is shown in FIGS. 4A-4J. These data indicate that the chimeric mAbs specifically bind to the HEK293-CLDN18.2 stable cell line.

Example 4: Humanization of Anti-CLDN18.2 mAbs

The mouse anti-CLDN18.2 mAbs 2-C3, 5-E22, 6411, 3-E21 and 3-P21 were humanized to reduce the potential of immunogenicity when used in human patients. The sequences of the variable regions of the heavy and light chains (VH and VL) were compared with the human antibody sequences in the Protein Data Bank (PDB) database and homology models were built. The CDRs in both the heavy and light chains of the mouse mAbs were grafted into human frameworks that have the highest possibility of maintaining the proper structure likely required for antigen binding. Backmutations from human residues to mouse residue or other mutations were designed when necessary. The sequences of the humanized VH and VL regions are shown in Table 7.

The humanized VH and VL regions were fused to the constant regions of human IgG1 heavy chain and kappa light chain, respectively. Constructs corresponding to the mAb sequences were used for transient transfection in 293E or CHO cells and purified mAbs were analyzed for their ability to bind to HEK293 cells stably transfected with full-length human CLDN18.2 using FACS. The $EC_{50}$ values of humanized mAbs for CLDN18.2 binding using a HEK293-CLDN18.2 stable pool are summarized in Table 8.

Results for the dose-dependent binding of humanized mAbs to the HEK293-CLDN18.2 stable pool are shown in FIGS. 5A-5G. FITC-based detection was used in the FACS experiments in Table 8 and FIGS. 5A-5C; Alexa Fluor® 488-based detection was used in the FACS experiments in FIGS. 5D-5G.

Figure 7:
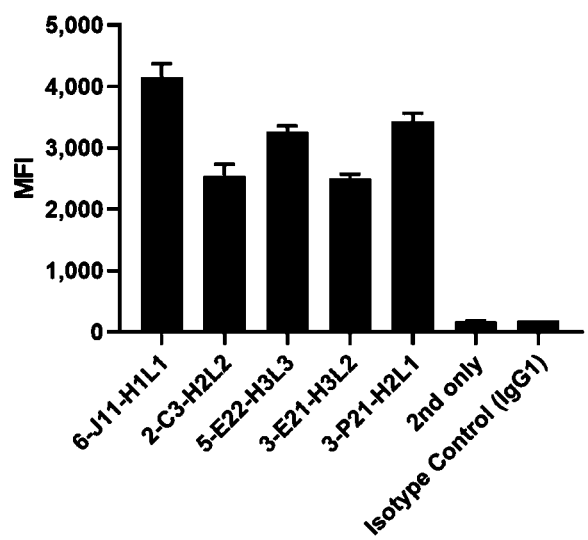
FIG. 7 shows the binding of the humanized anti-CLDN18.2 mAbs to the cancer cell line NUGC-4 at mAb concentration of 685 nM by FACS analysis.

Results for dose-dependent binding of humanized anti-CLDN18.2 mAbs to a HEK293-CLDN18.2 stable cell line by FACS analysis are shown in FIGS. 6A-6E. The binding of humanized anti-CLDN18.2 mAbs to the cancer cell line NUGC-4 at mAb concentration of 685 nM was also analyzed by FACS. The results for NUGC-4 binding by the humanized mAbs are shown in FIG. 7. Alexa Fluor® 488-based detection was used in the experiments in FIGS. 6A-6E and 7.

Figure 8A:
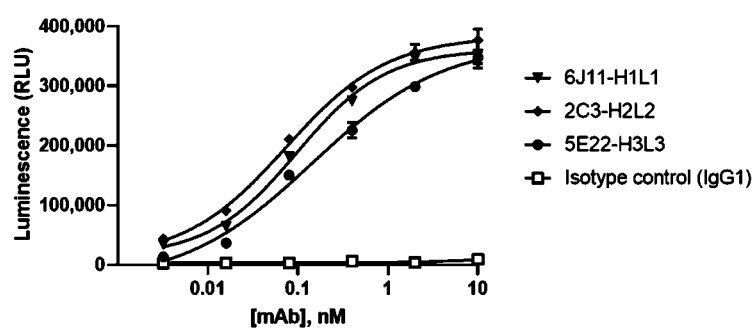
FIGS. 8A-8B show the results for the antibody-dependent cellular cytotoxicity (ADCC) activity of five humanized anti-CLDN18.2 mAbs and one chimeric anti-CLDN18.2 mAb.
Figure 8B:
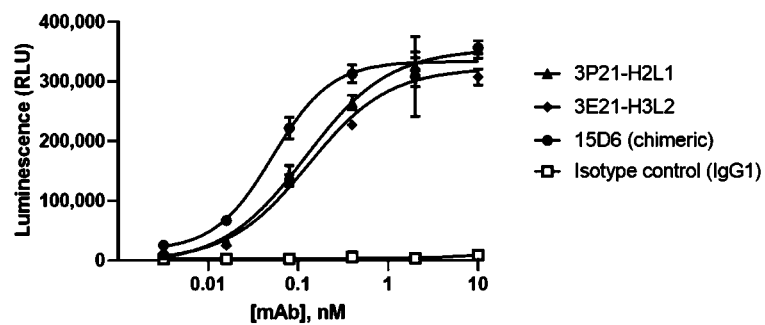

Antibody-dependent cellular cytotoxicity (ADCC) of mAbs was measured using the ADCC Reporter Bioassay Core Kit (Promega, cat. #G7010) according to the protocol provided by the manufacturer. Briefly, about 12,500 HEK293-CLDN18.2 cells per well were mixed with various concentrations of testing antibodies in ADCC Assay Buffer in a half-area 96-well microplate (Corning-Costar, cat. #3696). Then, about 37,500 per well of ADCC Bioassay Effector cells were added to a final volume of 37.5 μL and mixed. The plate was incubated at 37° C. for 6 hours without shaking. To measure the luciferase activity, 12.5 μL of assay mix was removed from each well and 25 μL of the Bio-Glo Luciferase Assay Reagent was added. The plates were incubated at room temperature for 10 minutes with shaking. 30 μL per well of the mixture was transferred to a white plate (BRAND, cat. #781621) to measure luminescence on an EnVision 2102 multimode plate reader. The results for the ADCC activity of the five humanized mAbs and one chimeric mAb are shown in FIG. 8A-8B. RLU, relative light unit.

TABLE 7

Sequences of heavy chain and light chain variable regions of humanized anti-CLDN1 8.2 mAbs

| VH/VL | SEQUENCE | SEQ ID NO: |
|---|---|---|
| 2-C3-H1 | QVTLRESGPALVKPTQTLTLTCTASGFTFSSYGMSWVRQ PPGKALEWVATISGGGSYTYYNPSLKDRFTISRDISANQ LVLKVTNMDPADTATYFCARQSRGNAMDYWGQGTTVTVSS | 142 |
| 2-C3-H2 | QVTLRESGPALVKPTQTLTLTCTFSGFTFSSYGMSWIRQ PPGKALEWLATISGGGSYTYYLDSLKDRFTISRDISKNQ VVLTVTNMDPADTATYFCARQSRGNAMDYWGQGTTVTVSS | 143 |
| 2-C3-L1 | DIQMTQSPSTLSASVGDRVTITCKSSQSLLNSGNQKNYL TWYQQKPGKAPKLLIYWASTRESGVPSRFSGSGSGTAFT LTISSLQPDDFATYYCQNDYSYPLTFGGGTKVEIK | 144 |
| 2-C3-L2 | DIQMTQSPSTLSASVGDRVTITCKSSQSLLNSGNQKNYL TWYQQKPGKAPKLLIYWASTRESGVPSRFSGSGSGTEFT LTISSLQPDDFATYYCQNDYSYPLTFGGGTKVEIK | 145 |
| 5-E22-H1 | QVQLVQSGVEVKKPGASVKVSCKASGYTITDNYMHWVRQ APGQGLEWIGEIYPGSGNTYFNEKFKNRATLTADKSTTT AYMELKSLQFDDTAVYFCARGFPYYAMDYWGQGTTVTVSS | 146 |
| 5-E22-H3 | QVQLVQSGAEVKKPGASVKVSCKASGYTITDNYMHWVRQ APGQGLEWIGEIYPGSGNTYYAEKFKNRATLTADKSIST AYMELSRLRSDDTAVYFCARGFPYYAMDYWGQGTLVTVSS | 147 |
| 5-E22-L1 | EIVMTQSPATLSLSPGERATLSCHARQNINVWLSWYQQK PGQAPRLLIYKASNLHTGVPARFSGSGSGTDFTLTISSL EPEDFAVYYCQQGQNYPLTFGGGTKVEIK | 148 |
| 5-E22-L2 | EIVLTQSPATLSLSPGERATLSCHARQNINVWLSWYQQK PGQAPRLLIYKASNLHTGIPARFSGSGSGTDFTLTISSL EPEDFAVYYCQQGQNYPLTFGGGTKVEIK | 149 |
| 5-E22-L3 | DIVMTQSPLSLPVTPGEPASISCHARQNINVWLSWYLQK PGQSPQLLIYKASNLHTGVPDRFSGSGSGTDFTLKISRV EAEDVGVYYCQQGQNYPLTFGQGTKVEIK | 150 |
| 6J11-H1 | EVQLVESGGGLVQPGGSLRLSCAASGFIFSSFGMHWVRQ APGKGLEWVAYISSGRSTMYYADSVKGRFTISRDNSKNT LYLQMNSLTAEDTAVYYCARGGFYGNSLDYWGQGTLVTVS S | 151 |
| 6J11-H2 | EVQLVESGGGLVQPGGSLRLSCAASGFIFSSFGMHWVRQ APGKGLEWVAYISSGRSTMYYADSVKGRFTISRDNSKNT LYLQMNSLRSEDTAVYYCARGGFYGNSLDYWGQGTLVTVS S | 152 |

TABLE 7-continued

Sequences of heavy chain and light chain variable regions of humanized anti-CLDN1 8.2 mAbs

| VH/VL | SEQUENCE | SEQ ID NO: |
|---|---|---|
| 6-J11-L1 | DIQMTQSPSSLSASVGDRVTITCKSSLSLLNSGNQKNYLTWYQQKPGKAPKLLIYWASTRESGVPSRFSGSGSGTDFTLTISSLQPEDFATYSCQNAYSYPLTFGQGTKVEIK | 153 |
| 3-E21-H1 | QVQLQESGPGLVRPSQTLSLTCTASGFTFSKYAMNWVRQPPGRGLEWVAFISNGGSYTEYNPSVKGRFTILRDNSKNQLSLRLSSVTAADTAVYYCARHDKGNALDYWGQGSLVTVSS | 154 |
| 3-E21-H2 | QVQLQESGPGLVRPSQTLSLTCTASGFTFSKYAMsWVRQPPGRGLEWVAFISNGGSYTEYNPSVKGRFTILRDNSKNQLSLkLSSVTAADTAVYYCARHDKGNALDYWGQGSLVTVSS | 155 |
| 3-E21-H3 | EVQLLESGGGLVQPGGSLRLSCAASGFTFSKYAMSWVRQAPGKGLEWVAAISNGGSYTYYADSVKGRFTISRDNSKNTLYLQMNSLRAEDTAVYYCARHDKGNALDYWGQGTLVTVSS | 156 |
| 3-E21-L1 | DIQMTQSPSSLSASVGDRVTITCKSSQSLLNSGNQKNYLTWYQQKPGKAPKLLIYWASNLQTGVPSRFSGSGSGTDFFTISSLQPEDIATYYCQNDYFYPLTFGQGTKVEIK | 157 |
| 3-E21-L2 | DIVMTQSPDSLAVSLGERATINCKSSQSLLNSGNQKNYLTWYQQKPGQPPKLLIYWASTRESGVPDRFSGSGSGTDFTLTISSLQAEDVAVYYCQNDYFYPLTFGQGTRLEIK | 158 |
| 3-P21-H1 | EIQLVESGGGLVQPGGSLRLSCAASGYSFTGYNIHWVRQAPGKGLEWIGYINPYFGSTDYADSVKGRATLSVDKSKNTAYLQMNSLRAEDTAVYYCARGAYYGNAMDYWGQGTLVTVSS | 159 |
| 3-P21-H2 | EIQLVESGGGLVQPGGSLRLSCAASGYSFTGYNmkWVRQAPGKGLEWIGnINPYFGSTnYADSVKGRATLSVDKSKNTAYLQMNSLRAEDTAVYYCARGAYYGNAMDYWGQGTLVTVSS | 160 |
| 3-P21-H3 | EIQLVQSGAEVKKPGESLKISCKASGYSFTGYNIGWVRQMPGKGLEWIGIINPYFGSTRYSPSFQGQATLSVDKSISTAYLQWSSLKASDTAMYYCARGAYYGNAMDYWGQGTLVTVSS | 161 |
| 3-P21-H4 | EIQLVQSGAEVKKPGESLKISCKASGYSFTGYNmkWVRQMPGKGLEWIGIINPYFGSTnYSPSFQGQATLSVDKSISTAYLQWSSLKASDTAMYYCARGAYYGNAMDYWGQGTLVTVSS | 162 |
| 3-P21-L1 | DIQMTQSPSSLSASVGDRVTITCRSSQSLLNSGNQKNYVTWYQQKPGKAPKLLIYWASFLYSGVPSRFSGSGSGTDFTLTISSLQPEDFATYYCQNDYFYPLTFGQGTKVEIK | 163 |
| 3-P21-L2 | DIQMTQSPSSLSASVGDRVTITCRSSQSLLNSGNQKNYVTWYQQKPGKAPKLLIYWAStreSGVPSRFSGSGSGTDFTLTISSLQPEDFATYYCQNDYFYPLTFGQGTKVEIK | 164 |
| 3-P21-L3 | DIVMTQSPDSLAVSLGERATINCKSSQSLLNSGNQKNYLTWYQQKPGQPPKLLIYWASTRESGVPDRFSGSGSGTDFTLTISSLQAEDVAVYYCQNDYFYPLTFGQGTKVEIK | 165 |

TABLE 8

$EC_{50}$ values of humanized mAbs for CLDN18.2 binding using a HEK293-CLDN18.2 stable pool

| Name | $EC_{50}$ (nM) |
|---|---|
| 2-C3-H1L1 | 9.8 |
| 2-C3-H1L2 | 9.1 |
| 2-C3-H2L1 | 8.8 |
| 2-C3-H2L2 | 8.0 |
| 5-E22-H1L1 | 59.0 |
| 5-E22-H1L2 | 258.6 |
| 5-E22-H1L3 | 61.0 |
| 5-E22-H3L1 | 12.1 |
| 5-E22-H3L2 | 19.4 |
| 5-E22-H3L3 | 14.7 |
| 6-J11-H1L1 | 11.2 |
| 6-J11-H2L1 | 11.4 |

2-C3-H1L1 refers to the mAb with the 2-C3-H1 heavy chain variable region and the 2-C3-L1 light chain variable region; all the other humanized mAbs in the table and the text adopt the same naming rule.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

It is claimed:

1. An isolated monoclonal antibody or antigen-binding fragment thereof comprising a heavy chain complementarity determining region 1 (HCDR1), HCDR2, HCDR3, a light chain complementarity determining region 1 (LCDR1), LCDR2, and LCDR3, having the polypeptide sequences of:
   (a) SEQ ID NOs: 21, 22, 23, 51, 52, and 53, respectively; or
   (b) SEQ ID NOs: 36, 37, 38, 66, 67, and 68, respectively;
wherein the antibody or antigen-binding fragment thereof specifically binds claudin 18.2 (CLDN18.2).

2. The isolated monoclonal antibody or antigen-binding fragment thereof of claim 1, comprising a heavy chain variable region having a polypeptide sequence at least 95% identical to SEQ ID NO: 1 or 11, or a light chain variable region having a polypeptide sequence at least 95% identical to SEQ ID NO: 2 or 12.

3. The isolated monoclonal antibody or antigen-binding fragment thereof of claim 1, comprising
   (a) a heavy chain variable region having the polypeptide sequence of SEQ ID NO:1, and a light chain variable region having the polypeptide sequence of SEQ ID NO:2; or
   (b) a heavy chain variable region having the polypeptide sequence of SEQ ID NO:11, and a light chain variable region having the polypeptide sequence of SEQ ID NO:12.

4. The isolated monoclonal antibody or antigen-binding fragment thereof of claim 1, wherein the antibody or antigen-binding fragment thereof is chimeric or human or humanized.

5. The isolated monoclonal antibody or antigen-binding fragment thereof of claim 4, wherein the isolated humanized antibody or antigen-binding fragment thereof comprises:
   (a) a heavy chain variable region having the polypeptide sequence of SEQ ID NO:142, and a light chain variable region having the polypeptide sequence of SEQ ID NO:144;
   (b) a heavy chain variable region having the polypeptide sequence of SEQ ID NO:142, and a light chain variable region having the polypeptide sequence of SEQ ID NO:145;
   (c) a heavy chain variable region having the polypeptide sequence of SEQ ID NO:143, and a light chain variable region having the polypeptide sequence of SEQ ID NO:144;
   (d) a heavy chain variable region having the polypeptide sequence of SEQ ID NO:143, and a light chain variable region having the polypeptide sequence of SEQ ID NO:145;
   (e) a heavy chain variable region having the polypeptide sequence of SEQ ID NO:151, and a light chain variable region having the polypeptide sequence of SEQ ID NO:153; or (f) a heavy chain variable region having the polypeptide sequence of SEQ ID NO:152, and a light chain variable region having the polypeptide sequence of SEQ ID NO:153.

6. An isolated nucleic acid encoding the monoclonal antibody or antigen-binding fragment thereof of claim 1.

7. A vector comprising the isolated nucleic acid of claim 6.

8. A host cell comprising the vector of claim 7.

9. A pharmaceutical composition, comprising the isolated monoclonal antibody or antigen-binding fragment thereof of claim 1 and a pharmaceutically acceptable carrier.

10. A method of treating a claudin 18.2 (CLDN18.2) positive cancer in a subject in need thereof, comprising administering to the subject the pharmaceutical composition of claim 9.

11. The method of claim 10, wherein the cancer is selected from the group consisting of a gastric cancer, an esophageal cancer, a colon cancer, a pancreatic cancer, a bile duct cancer, and a cholangiocarcinoma.

12. A method of producing the monoclonal antibody or antigen-binding fragment thereof of claim 1, comprising culturing a cell comprising a nucleic acid encoding the monoclonal antibody or antigen-binding fragment thereof under conditions to produce the monoclonal antibody or antigen-binding fragment thereof and recovering the antibody or antigen-binding fragment thereof from the cell or culture.

13. A method of producing a pharmaceutical composition comprising the monoclonal antibody or antigen-binding fragment of claim 1, comprising combining the monoclonal antibody or antigen-binding fragment thereof with a pharmaceutically acceptable carrier to obtain the pharmaceutical composition.

14. A method of determining a level of CLDN18.2 in a subject, the method comprising:
  a. obtaining a sample from the subject;
  b. contacting the sample with an isolated monoclonal antibody or antigen-binding fragment thereof of claim 1; and
  c. determining a level of CLDN18.2 in the subject.

15. The method of claim 14, wherein the sample is a tissue sample or a blood sample.

16. The method of claim 15, wherein the tissue sample is a cancer tissue sample.

\* \* \* \* \*